United States Patent
Alcaraz et al.

(10) Patent No.: US 9,365,577 B2
(45) Date of Patent: Jun. 14, 2016

(54) PYRIMIDINONE COMPOUNDS AS HUMAN NEUTROPHIL ELASTASE INHIBITORS

(71) Applicant: CHIESI FARMACEUTICI S.p.A., Parma (IT)

(72) Inventors: Lilian Alcaraz, Harlow (GB); Robert Andrew Heald, Harlow (GB); Jonathan Mark Sutton, Harlow (GB); Elisabetta Armani, Parma (IT); Carmelida Capaldi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 14/108,904

(22) Filed: Dec. 17, 2013

(65) Prior Publication Data
US 2014/0171414 A1     Jun. 19, 2014

(30) Foreign Application Priority Data

Dec. 18, 2012  (EP) .................................. 12197767
Mar. 12, 2013  (EP) .................................. 13158757

(51) Int. Cl.
| C07D 487/04 | (2006.01) |
| A61K 31/519 | (2006.01) |
| C07C 309/20 | (2006.01) |
| C07C 309/29 | (2006.01) |
| C07D 453/02 | (2006.01) |
| C07D 487/08 | (2006.01) |

(52) U.S. Cl.
CPC ............ *C07D 487/04* (2013.01); *C07C 309/20* (2013.01); *C07C 309/29* (2013.01); *C07D 453/02* (2013.01); *C07D 487/08* (2013.01)

(58) Field of Classification Search
CPC ............................. C07D 487/04; A61K 31/519
USPC ........................................ 514/262.1; 544/262
See application file for complete search history.

(56) References Cited

U.S. PATENT DOCUMENTS

| 2012/0004203 A1* | 1/2012 | Von Nussbaum .... C07D 487/04 514/171 |
| 2013/0123278 A1* | 5/2013 | Edwards et al. ......... 514/259.31 |
| 2013/0150380 A1* | 6/2013 | Edwards et al. ......... 514/259.31 |

FOREIGN PATENT DOCUMENTS

| WO | 2011/110858 | 9/2011 |
| WO | 2011/110859 | 9/2011 |

OTHER PUBLICATIONS

European Search Report in Application No. 12197767.2 issued Feb. 28, 2013.
U.S. Appl. No. 14/571,755, filed Dec. 16, 2014, Alcaraz et al.
U.S. Appl. No. 14/731,786, filed Jun. 5, 2015, Armani et al.

* cited by examiner

*Primary Examiner* — Sreeni Padmanabhan
*Assistant Examiner* — Irina Neagu
(74) *Attorney, Agent, or Firm* — Oblon, McClelland, Maier & Neustadt, L.L.P.

(57) ABSTRACT

Pyrimidinone compounds defined herein exhibit human neutrophil elastase inhibitory properties and are useful for treating diseases and conditions in which HINE is implicated.

16 Claims, No Drawings

PYRIMIDINONE COMPOUNDS AS HUMAN NEUTROPHIL ELASTASE INHIBITORS

CROSS REFERENCES TO RELATED APPLICATIONS

This claims priority to European Patent Applications No. 12197767.2, filed on Dec. 18, 2012, and European Patent Applications No. 13158757.8, filed on Mar. 12, 2013, both of which are incorporated herein by reference in their entireties.

BACKGROUND OF THE INVENTION

1. Field of the Invention

The present invention relates to heterocyclic compounds, which are pyrimidinone derivatives having human neutrophil elastase inhibitory properties. The present invention also relates to therapeutic uses of such a compound.

2. Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. In *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (see Wright, J. L. et al. *Am. J. Respir. Crit. Care Med.* 2002, 166, 954-960; and Churg, A. et al. *Am. J. Respir. Crit. Care Med.* 2003, 168, 199-207, both of which are incorporated herein by references in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodelling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the "elastase:anti-elastase hypothesis"), in which an imbalance of HNE and endogenous antiproteases such as α1-antitrypsin ($\alpha_1$-AT), secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far. In particular, International Patent Application No. WO2011/110858 and No. WO2011/110859 (both of which are incorporated herein by reference in their entireties) describe some pyrimidine derivatives having human neutrophil elastase inhibitory properties and their use in therapy.

Although several HNE inhibitors have been disclosed so far as above reported, there is still a need for further HNE inhibitors. Particularly, there is still a need for further HNE inhibitors endowed with a high potency for HNE enzyme inhibition. Particularly advantageous would also be the identification of further HNE inhibitors endowed with a high potency for HNE enzyme inhibition and which would show an appropriate developability profile as an inhalation treatment.

SUMMARY OF THE INVENTION

Accordingly, it is one object of the present invention to provide novel HNE inhibitors.

It is another object of the present invention to provide novel NE inhibitors which exhibit a high potency for HNE enzyme inhibition.

It is another object of the present invention to provide novel HNE inhibitors which exhibit an appropriate developability profile for inhalation treatment.

It is another object of the present invention to provide novel therapeutic uses of such an HNE inhibitor.

These and other objects, which will become apparent during the following detailed description, have been achieved by the inventors' discovery that compounds of formula (I) described below are inhibitors of HNE, and are useful in the treatment of diseases or conditions in which HNE activity plays a part.

DETAILED DESCRIPTION OF THE PREFERRED EMBODIMENTS

Thus, in one aspect the present invention provides compound of formula (I) and pharmaceutically acceptable salts thereof:

(I)

[Chemical structure of formula (I) showing a bicyclic system with substituents $R_1$, $R_2$, $R_3$, NC, A, B, D, and a trifluoromethyl-phenyl group]

wherein
A is CH or N;
B is CH or N;
D is CH or N;
$R_1$ is selected from the group consisting of:
hydrogen;
$(C_1$-$C_6)$alkyl;
$NR_7R_8(C_1$-$C_6)$alkyl;
$(C_1$-$C_4)$alkenyl;
phenyl$(C_1$-$C_6)$alkyl wherein such phenyl ring is optionally substituted by a group $NR_{15}R_{16}(C_1$-$C_6)$alkyl or by $N^+R_{15}R_{16}R_{17}(C_1$-$C_6)$alkyl;
a group —$CH_2(CH_2)_n$OH;
a group —$(CH_2)_n$CONR$_5$R$_6$;
a group —$(CH_2)_n$SO$_2$NR$_5$R$_6$;
a group —$CH_2$—$(CH_2)_n$NR$_5$SO$_2$R$_6$;
a group —$(CH_2)_t$—$(C_6H_4)$—SO$_2(C_1$-$C_4)$alkyl;
a group —$(CH_2)_r$SO$_2(C_1$-$C_4)$alkyl wherein such $(C_1$-$C_4)$ alkyl is optionally substituted by a group —$NR_{15}R_{16}$ or —$N^+R_{15}R_{16}R_{17}$;
a group —$SO_2$-phenyl wherein such phenyl ring is optionally substituted by $NR_7R_8(C_1$-$C_6)$alkyl; and
a group —$(CH_2)_n$—W wherein W is a 5-6-membered heteroaryl ring which is optionally substituted by a group —$SO_2(C_1$-$C_4)$alkyl;
n is 1, 2 or 3;
t is zero, 1, 2 or 3;
r is zero, 1, 2, 3 or 4;
$R_5$ is selected from the group consisting of: hydrogen, $(C_1$-$C_6)$alkyl, $NR_{16}R_{15}(C_1$-$C_6)$alkyl and $N^+R_{17}R_{15}R_{16}(C_1$-$C_6)$alkyl;
$R_6$ is hydrogen or $(C_1$-$C_6)$alkyl;
$R_7$ is selected from the group consisting of hydrogen, $(C_1$-$C_6)$alkyl, $(C_1$-$C_6)$alkylcarbonyl, —$SO_2(C_1$-$C_4)$alkyl, and $NR_{16}R_{15}(C_1$-$C_6)$alkyl;
$R_8$ is hydrogen or $(C_1$-$C_6)$alkyl;
alternatively, $R_7$ and $R_8$ may form together with the nitrogen atom to which they are attached a $(C_5$-$C_7)$heterocycloalkyl ring system which is optionally substituted by one or more $(C_1$-$C_6)$ alkyl groups and oxo;
$R_{16}$ is hydrogen or $(C_1$-$C_6)$alkyl;
$R_{15}$ is hydrogen or $(C_1$-$C_6)$alkyl;
$R_{17}$ is hydrogen or $(C_1$-$C_6)$alkyl;
$R_3$ is a cyano group or a group —C(O)—XR$_4$;
X is a divalent group selected from —O—, —$(CH_2)$— and —NH—;
$R_4$ is a group selected from the group consisting of:
hydrogen;
$(C_1$-$C_6)$alkyl;
a group of formula -[Alk$^1$]-Z wherein Alk$^1$ represents a $(C_1$-$C_4)$alkylene radical and Z is:
(i) —$NR_9R_{10}$ wherein $R_9$ and $R_{10}$ are independently hydrogen, $(C_1$-$C_6)$alkyl or $(C_3$-$C_6)$cycloalkyl group, wherein such $(C_1$-$C_6)$alkyl or $(C_3$-$C_6)$cycloalkyl group are optionally substituted by one to four $R_{35}$ groups which are at each occurrence independently selected from the group consisting of $(C_1$-$C_6)$alkyl, $(C_1$-$C_6)$alkoxyl, hydroxyl, hydroxyl-$C_1$-$C_6$-alkyl, halo, trifluoromethyl, trifluoromethoxy; or, taken together with the nitrogen to which they are attached, form a monocyclic $(C_5$-$C_7)$heterocyclic ring which may contain a further heteroatom selected from N, O, and S and which is optionally substituted by one to four $R_{35}$ groups which are at each occurrence independently selected from the group consisting of $(C_1$-$C_6)$alkyl, $(C_1$-$C_6)$alkoxyl, hydroxyl, hydroxyl-$C_1$-$C_6$-alkyl, halo, trifluoromethyl, and trifluoromethoxy; or
(ii) —$N^+R_{11}R_{12}R_{13}$ wherein $R_{11}$, $R_{12}$ and $R_{13}$ are each independently $(C_1$-$C_6)$alkyl or $(C_3$-$C_6)$cycloalkyl group, wherein such $(C_1$-$C_6)$alkyl or $(C_3$-$C_6)$cycloalkyl group are optionally substituted by one to four $R_{36}$ groups which are at each occurrence independently selected from the group consisting of $(C_1$-$C_6)$alkyl, $(C_1$-$C_6)$alkoxyl, hydroxyl, hydroxyl-$C_1$-$C_6$-alkyl, halo, trifluoromethyl, and trifluoromethoxy; or any two of $R_{11}$, $R_{12}$ and $R_{13}$ taken together with the nitrogen to which they are attached form a monocyclic $(C_5$-$C_7)$heterocyclic ring which may contain a further heteroatom selected from N, O, and S and the other of $R_{11}$, $R_{12}$ and $R_{13}$ is a $(C_1$-$C_6)$ alkyl or an optionally substituted $(C_3$-$C_6)$cycloalkyl group, wherein such monocyclic$(C_5$-$C_7)$heterocyclic, $(C_1$-$C_6)$alkyl or $(C_3$-$C_6)$cycloalkyl group are optionally substituted by one to four $R_{36}$ groups which are at each occurrence independently selected from the group consisting of $(C_1$-$C_6)$alkyl, $(C_1$-$C_6)$alkoxyl, hydroxyl, hydroxyl-$C_1$-$C_6$-alkyl, halo, trifluoromethyl, and trifluoromethoxy; and
a radical of formula —$(CH_2)_q$-[Q]-$(CH_2)_p$ Z wherein Z is as above defined, q is an integer ranging from zero to 3, p is an integer ranging from zero to 3 and Q represents a divalent group selected from —O—, phenylene, $(C_5$-$C_7)$heterocycloalkylene, $(C_3$-$C_6)$cycloalkyl and pyridinylene, wherein such phenylene, $(C_5$-$C_7)$heterocycloalkylene, $(C_3$-$C_6)$cycloalkyl and pyridinylene are optionally substituted by one to four $R_{37}$ groups which are at each occurrence independently selected from the group consisting of $(C_1$-$C_6)$ alkyl, $(C_1$-$C_6)$alkoxyl, hydroxyl, hydroxyl-$C_1$-$C_6$-alkyl, halo, trifluoromethyl, and trifluoromethoxy;
$R_2$ is selected from the group consisting of:
$R_{14}$O$(C_1$-$C_6)$alkyl;
$NR_{18}R_{19}$(C1-$C_6)$alkyl;
—CONR$_{21}$R$_{20}$;
$C_2$-$C_6$-alkenyl which $C_2$-$C_6$-alkenyl may be optionally substituted by a group —OH or —$NR_{18}R_{19}$;
$C_2$-$C_6$-alkynyl which $C_2$-$C_6$-alkynyl may be optionally substituted by a group —OH or —$NR_{18}R_{19}$; and
a group —[CH$_2$]$_y$-G-[CH$_2$]$_j$—CH$_2$—$N^+R_{22}R_{23}R_{24}$
or $R_2$ is a group:

[Chemical structures showing two groups with $R_{22}$, $R_{23}$ substituents on piperidine/piperazine rings connected via —CH$_2$—G—CH$_2$— linkers]

-continued

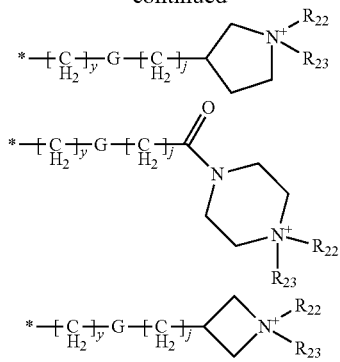

or R$_2$ is a group:

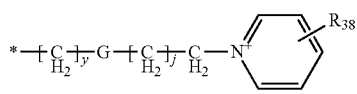

R$_{14}$ is hydrogen or (C$_1$-C$_6$)alkyl which may be optionally substituted by a group (C$_1$-C$_4$)alkoxyl;
R$_{18}$ is hydrogen or (C$_1$-C$_6$)alkyl;
R$_{19}$ is hydrogen or (C$_1$-C$_6$)alkyl;
R$_{20}$ is selected in the group consisting of: hydrogen, (C$_1$-C$_6$)alkyl, (C$_1$-C$_6$)alkylNR$_{18}$R$_{19}$;
R$_{21}$ is hydrogen or (C$_1$-C$_6$)alkyl;
j is an integer ranging from zero to 4;
y is an integer ranging from zero to 4;
G is a divalent linker selected from the group consisting of —O—, —(SO$_2$)—, NR$_{25}$, a bond, C$_2$-C$_6$-alkenylene, C$_2$-C$_6$-alkynylene, (C$_3$-C$_6$)cycloalkylene, mono or bicyclic heterocycloalkylene, —[CONR$_{25}$]— and —[NR$_{25}$CO]—;
R$_{25}$ is hydrogen or (C$_1$-C$_6$)alkyl;
R$_{22}$ is selected from the group consisting of (C$_1$-C$_6$)alkyl, which (C$_1$-C$_6$)alkyl is optionally substituted by one or more groups (C$_3$-C$_6$)cycloalkyl, phenyl, benzyl, CN, —OR$_{26}$, —SO$_2$R$_{26}$, —CO$_2$R$_{26}$, —CONR$_{26}$R$_{27}$ or —SO$_2$NR$_{26}$R$_{27}$;
(C$_3$-C$_{10}$)cycloalkyl which is optionally substituted by one or more groups —OR$_{26}$, —SO$_2$R$_{26}$, —CO$_2$R$_{26}$, —CONR$_{26}$R$_{27}$ or —SO$_2$NR$_{26}$R$_{27}$; and (C$_4$-C$_7$)heterocycloalkyl which is optionally substituted by one or more groups —OR$_{26}$, —SO$_2$R$_{26}$, —CO$_2$R$_{26}$, —CONR$_{26}$R$_{27}$ or —SO$_2$NR$_{26}$R$_{27}$;
R$_{26}$ is hydrogen or (C$_1$-C$_6$)alkyl;
R$_{27}$ is hydrogen or (C$_1$-C$_6$)alkyl;
R$_{23}$ is hydrogen or (C$_1$-C$_6$)alkyl, which (C$_1$-C$_6$)alkyl is optionally substituted by one or more groups —OR$_{29}$, —SO$_2$R$_{29}$, —CO$_2$R$_{29}$, —CONR$_{29}$R$_{30}$ or —SO$_2$NR$_{29}$R$_{30}$;
R$_{24}$ is hydrogen or (C$_1$-C$_6$)alkyl, which (C$_1$-C$_6$)alkyl is optionally substituted by one or more groups —OR$_{31}$, —SO$_2$R$_{31}$, —CO$_2$R$_{31}$, —CONR$_{31}$R$_{32}$ or —SO$_2$NR$_{31}$R$_{32}$;
alternatively, R$_{23}$ and R$_{24}$ may form together with the nitrogen atom to which they are attached a 5-11-membered saturated monocyclic or bicyclic heterocyclic ring system which is optionally substituted by one or more groups —OR$_{28}$, halo, C$_1$-C$_6$ alkyl, —SO$_2$R$_{33}$, —CO$_2$R$_{33}$, —CONR$_{33}$R$_{34}$ or —SO$_2$NR$_{33}$R$_{34}$; and which 5-11-membered saturated monocyclic or bicyclic ring optionally contains a further heteroatom which is oxygen or nitrogen or a group —SO$_2$—;
or R$_{22}$ together with R$_{23}$, R$_{24}$ and the nitrogen atom they are attached to, may form a bridged bicyclic heterocyclic ring system;
R$_{28}$ is hydrogen or (C$_1$-C$_6$)alkyl;
R$_{29}$ is hydrogen or (C$_1$-C$_6$)alkyl;
R$_{30}$ is hydrogen or (C$_1$-C$_6$)alkyl;
R$_{31}$ is hydrogen or (C$_1$-C$_6$)alkyl;
R$_{32}$ is hydrogen or (C$_1$-C$_6$)alkyl;
R$_{33}$ is hydrogen or (C$_1$-C$_6$)alkyl;
R$_{34}$ is hydrogen or (C$_1$-C$_6$)alkyl;
R$_{38}$ represents one or two optional substituents at each occurrence selected from the group consisting of (C$_1$-C$_6$)alkyl, (C$_1$-C$_6$)alkoxyl, hydroxyl, hydroxyl-C$_1$-C$_6$-alkyl, halo, trifluoromethyl, and trifluoromethoxy;
wherein only two of A, B and D may be at the same time a nitrogen atom;
wherein if one or more groups N$^+$R$_{11}$R$_{12}$R$_{13}$— or N$^+$R$_{15}$R$_{16}$R$_{17}$— are present, they form quaternary salts with a pharmaceutically acceptable counter ion;
and wherein groups R$_5$ to R$_{38}$, and n may assume the same or different meanings at each occurrence, if present in more than one group.

Compounds of formula (I) may be prepared in the form of salts, particularly pharmaceutically acceptable salts, N-oxides, hydrates, solvates, and polymorphs thereof. Any reference to a compound herein, or reference to "compounds of the invention", "compounds of formula (I)", and the like includes such compounds whether or not in salt, N-oxide, hydrate, solvate or polymorphic form.

Compounds of the present invention may be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema, and cystic fibrosis.

Hence other aspects of the present invention include (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

In one embodiment, the present invention provides a compound of formula (IB), or a pharmaceutically acceptable salt thereof:

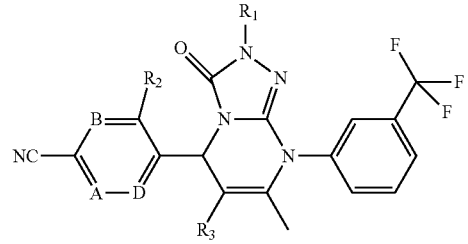

(IB)

wherein
A is CH or N;
B is CH or N;
D is CH or N;
R$_1$ is selected from the group consisting of:
hydrogen;
(C$_1$-C$_6$)alkyl;

$NR_7R_8(C_1-C_6)$alkyl;

$(C_1-C_4)$alkenyl;

phenyl$(C_1-C_6)$alkyl wherein such phenyl ring is optionally substituted by a group $NR_{15}R_{16}(C_1-C_6)$alkyl or by $N^+R_{15}R_{16}R_{17}(C_1-C_6)$alkyl;

a group —$CH_2(CH_2)_n$OH;

a group —$(CH_2)_n CONR_5R_6$;

a group —$(CH_2)_n SO_2NR_5R_6$;

a group —$CH_2$—$(CH_2)_n NR_5SO_2R_6$;

a group —$(CH_2)_t$—$(C_6H_4)$—$SO_2(C_1-C_4)$alkyl;

a group —$(CH_2)_rSO_2(C_1-C_4)$alkyl wherein such $(C_1-C_4)$alkyl is optionally substituted by a group —$NR_{15}R_{16}$ or —$N^+R_{15}R_{16}R_{17}$;

a group —$SO_2$-phenyl wherein such phenyl ring is optionally substituted by $NR_7R_8(C_1-C_6)$alkyl; and a group —$(CH_2)_n$—W wherein W is a 5-6-membered heteroaryl ring which is optionally substituted by a group —$SO_2(C_1-C_4)$alkyl;

n is 1, 2 or 3;

t is zero, 1, 2 or 3;

r is zero, 1, 2, 3 or 4;

$R_5$ is selected from the group consisting of hydrogen, $(C_1-C_6)$alkyl, $NR_{16}R_{15}(C_1-C_6)$alkyl, and $N^+R_{17}R_{15}R_{16}(C_1-C_6)$alkyl;

$R_6$ is hydrogen or $(C_1-C_6)$alkyl;

$R_7$ is selected from the group consisting of hydrogen, $(C_1-C_6)$alkyl, $(C_1-C_6)$alkylcarbonyl, —$SO_2(C_1-C_4)$alkyl, and $NR_{16}R_{15}(C_1-C_6)$alkyl;

$R_8$ is hydrogen or $(C_1-C_6)$alkyl;

alternatively, $R_7$ and $R_8$ may form together with the nitrogen atom to which they are attached a $(C_5-C_7)$heterocycloalkyl ring system which is optionally substituted by one or more groups $(C_1-C_6)$ alkyl and oxo;

$R_{16}$ is hydrogen or $(C_1-C_6)$alkyl;

$R_{15}$ is hydrogen or $(C_1-C_6)$alkyl;

$R_{17}$ is hydrogen or $(C_1-C_6)$alkyl;

$R_3$ is a group cyano or a group —C(O)—$XR_4$;

X is a divalent group selected from —O—, —$(CH_2)$— and —NH—;

$R_4$ is a group selected in the list consisting of:
hydrogen;
$(C_1-C_6)$alkyl;
a group of formula -[Alk$^1$]-Z wherein Alk$^1$ represents a $(C_1-C_4)$alkylene radical and Z is:
  (i) —$NR_9R_{10}$ wherein $R_9$ and $R_{10}$ are independently hydrogen, $(C_1-C_6)$alkyl or $(C_3-C_6)$cycloalkyl group, wherein such $(C_1-C_6)$alkyl or $(C_3-C_6)$cycloalkyl group are optionally substituted by one to four $R_{35}$ groups which are at each occurrence independently selected from the group consisting of: $(C_1-C_6)$alkyl, $(C_1-C_6)$alkoxyl, hydroxyl, hydroxyl-$C_1-C_6$-alkyl, halo, trifluoromethyl, and trifluoromethoxy; or, taken together with the nitrogen to which they are attached, form a monocyclic $(C_5-C_7)$heterocyclic ring which may contain a further heteroatom selected from N, O, and S and which is optionally substituted by one to four $R_{35}$ groups which are at each occurrence independently selected in the group consisting of: $(C_1-C_6)$alkyl, $(C_1-C_6)$alkoxyl, hydroxyl, hydroxyl-$C_1-C_6$-alkyl, halo, trifluoromethyl, and trifluoromethoxy; or
  (ii) —$N^+R_{11}R_{12}R_{13}$ wherein $R_{11}$, $R_{12}$ and $R_{13}$ are each independently $(C_1-C_6)$alkyl or $(C_3-C_6)$cycloalkyl group, wherein such $(C_1-C_6)$alkyl or $(C_3-C_6)$cycloalkyl group are optionally substituted by one to four $R_{36}$ groups which are at each occurrence independently selected from the group consisting of: $(C_1-C_6)$alkyl, $(C_1-C_6)$alkoxyl, hydroxyl, hydroxyl-$C_1-C_6$-alkyl, halo, trifluoromethyl, and trifluoromethoxy; or any two of $R_{11}$, $R_{12}$ and $R_{13}$ taken together with the nitrogen to which they are attached form a monocyclic $(C_5-C_7)$heterocyclic ring which may contain a further heteroatom selected from N, O, and S and the other of $R_{11}$, $R_{12}$ and $R_{13}$ is a $(C_1-C_6)$alkyl or an optionally substituted $(C_3-C_6)$cycloalkyl group, wherein such monocyclic $(C_5-C_7)$heterocyclic, $(C_1-C_6)$alkyl or $(C_3-C_6)$cycloalkyl group are optionally substituted by one to four $R_{36}$ groups which are at each occurrence independently selected from the group consisting of: $(C_1-C_6)$alkyl, $(C_1-C_6)$alkoxyl, hydroxyl, hydroxyl-$C_1-C_6$-alkyl, halo, trifluoromethyl, and trifluoromethoxy;

a radical of formula —$(CH_2)_q$-[Q]-$(CH_2)_p$ Z wherein Z is as above defined, q is an integer ranging from zero to 3, p is an integer ranging from zero to 3 and Q represents a divalent group selected from: —O—, phenylene, $(C_5-C_7)$heterocycloalkylene, $(C_3-C_6)$cycloalkyl and pyridinylene, wherein such phenylene, $(C_5-C_7)$heterocycloalkylene, $(C_3-C_6)$cycloalkyl and pyridinylene are optionally substituted by one to four $R_{37}$ groups which are at each occurrence independently selected from the group consisting of: $(C_1-C_6)$alkyl, $(C_1-C_6)$alkoxyl, hydroxyl, hydroxyl-$C_1-C_6$-alkyl, halo, trifluoromethyl, and trifluoromethoxy; $R_2$ is selected from a group consisting of:

$R_{14}O(C_1-C_6)$alkyl; $NR_{18}R_{19}(C_1-C_6)$alkyl; —$CONR_{21}R_{20}$; $C_2-C_6$-alkenyl which $C_2-C_6$-alkenyl may be optionally substituted by a group —OH or —$NR_{18}R_{19}$; $C_2-C_6$-alkynyl which $C_2-C_6$-alkynyl may be optionally substituted by a group —OH or —$NR_{18}R_{19}$; and a group —$[CH_2]_y$-G-$[CH_2]_j$—$CH_2$—$N^+R_{22}R_{23}R_{24}$ or $R_2$ is a group:

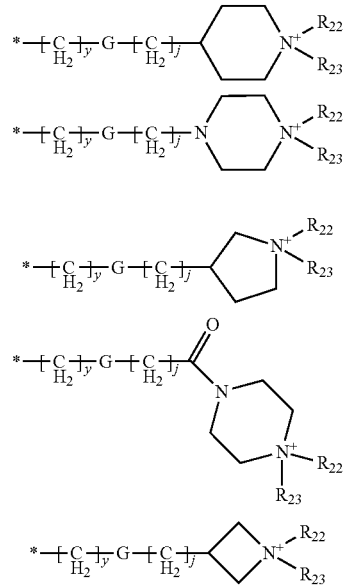

or $R_2$ is a group:

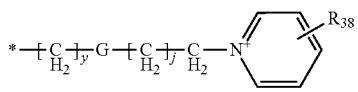

$R_{14}$ is hydrogen or $(C_1-C_6)$alkyl which may be optionally substituted by a group $(C_1-C_4)$alkoxyl;
$R_{18}$ is hydrogen or $(C_1-C_6)$alkyl;
$R_{19}$ is hydrogen or $(C_1-C_6)$alkyl;
$R_{20}$ is selected from the group consisting of hydrogen, $(C_1-C_6)$alkyl, $(C_1-C_6)$alkylN$R_{18}R_{19}$;
$R_{21}$ is hydrogen or $(C_1-C_6)$alkyl;
j is an integer ranging from zero to 4;
y is an integer ranging from zero to 4;
G is a divalent linker selected from the group consisting of —O—, —(SO$_2$)—, N$R_{25}$, a bond, $C_2-C_6$-alkenylene, $C_2-C_6$-alkynylene, $(C_3-C_6)$cycloalkylene, mono or bicyclic heterocycloalkylene, —[CONR$_{25}$]— and —[NR$_{25}$CO]—;
$R_{25}$ is hydrogen or $(C_1-C_6)$alkyl;
$R_{22}$ is selected from the group consisting of $(C_1-C_6)$alkyl, which $(C_1-C_6)$alkyl is optionally substituted by one or more groups —OR$_{26}$, —SO$_2R_{26}$, —CO$_2R_{26}$, —CONR$_{26}R_{27}$ or —SO$_2$NR$_{26}R_{27}$; $(C_3-C_6)$cycloalkyl; and $(C_4-C_7)$heterocycloalkyl;
$R_{26}$ is hydrogen or $(C_1-C_6)$alkyl;
$R_{27}$ is hydrogen or $(C_1-C_6)$alkyl;
$R_{23}$ is hydrogen or $(C_1-C_6)$alkyl, which $(C_1-C_6)$alkyl is optionally substituted by one or more groups —OR$_{29}$, —SO$_2R_{29}$, —CO$_2R_{29}$, —CONR$_{29}R_{30}$ or —SO$_2$NR$_{29}R_{30}$;
$R_{24}$ is hydrogen or $(C_1-C_6)$alkyl, which $(C_1-C_6)$alkyl is optionally substituted by one or more groups —OR$_{31}$, —SO$_2R_{31}$, —CO$_2R_{31}$, —CONR$_{31}R_{32}$ or —SO$_2$NR$_{31}R_{32}$;
alternatively, $R_{23}$ and $R_{24}$ may form together with the nitrogen atom to which they are attached a 5-11-membered saturated monocyclic or bicyclic heterocyclic ring system which is optionally substituted by one or more groups —OR$_{28}$, halo, $C_1-C_6$ alkyl, —SO$_2R_{33}$, —CO$_2R_{33}$, —CONR$_{33}R_{34}$ or —SO$_2$NR$_{33}R_{34}$; and which 5-11-membered saturated monocyclic or bicyclic ring optionally contains a further heteroatom which is oxygen or nitrogen or a group —SO$_2$—;
or $R_{22}$ together with $R_{23}$, $R_{24}$ and the Nitrogen atom they are attached to, may form a bridged bicyclic heterocyclic ring system;
$R_{28}$ is hydrogen or $(C_1-C_6)$alkyl;
$R_{29}$ is hydrogen or $(C_1-C_6)$alkyl;
$R_{30}$ is hydrogen or $(C_1-C_6)$alkyl;
$R_{31}$ is hydrogen or $(C_1-C_6)$alkyl;
$R_{32}$ is hydrogen or $(C_1-C_6)$alkyl;
$R_{33}$ is hydrogen or $(C_1-C_6)$alkyl;
$R_{34}$ is hydrogen or $(C_1-C_6)$alkyl;
$R_{38}$ represents one or two optional substituents at each occurrence selected from the group consisting of: $(C_1-C_6)$ alkyl, $(C_1-C_6)$alkoxyl, hydroxyl, hydroxyl-$C_1-C_6$-alkyl, halo, trifluoromethyl, and trifluoromethoxy;
wherein only two of A, B, and D may be at the same time a nitrogen atom; wherein if one or more groups N$^+$R$_{11}$R$_{12}$R$_{13}$— or N$^+$R$_{15}$R$_{16}$R$_{17}$— are present, they form quaternary salts with a pharmaceutically acceptable counter ion;
and wherein groups $R_5$ to $R_{37}$ and n may assume the same or different meanings at each occurrence, if present in more than one group.

Terminology:
The term "$(C_a$, —$C_b)$alkyl" wherein a and b are integers refers to a straight or branched chain alkyl radical having from a to b carbon atoms. Thus, when a is 1 and b is 6, for example, the term includes methyl, ethyl, n-propyl, isopropyl, n-butyl, isobutyl, sec-butyl, t-butyl, n-pentyl, and n-hexyl.

The term "$(C_d-C_b)$alkenyl" wherein a and b are integers refers to a straight or branched chain alkenyl moiety having from d to b carbon atoms having at least one double bond of either E or Z stereochemistry where applicable. Thus, when d is 2 and b is 6, for example, the term includes, for example, vinyl, allyl, 1- and 2-butenyl, and 2-methyl-2-propenyl.

By analogy, the expression "$(C_d-C_b)$alkenylene" refers to a divalent "$(C_d-C_b)$alkenyl" radical as above defined.

The term "$(C_d-C_b)$alkynyl" refers to straight or branched carbon chains with one or more triple bonds wherein the number atoms is in the range 2 to 6.

By analogy, the expression "$(C_d-C_b)$alkynylene" refers to a divalent "$(C_d-C_b)$alkynyl" radical as above defined.

The expressions "NR$_{15}$R$_{16}(C_a-C_b)$alkyl", "NR$_{18}$R$_{19}(C_a-C_b)$alkyl" and "NR$_7$R$_8(C_a-C_b)$alkyl", wherein a and b are as above defined, refer to the above defined "$(C_a-C_b)$alkyl" groups wherein one hydrogen atom is replaced by one a group —NR$_{15}$R$_{16}$, —NR$_{18}$R$_{19}$ or —NR$_7$R$_8$ respectively.

The expression "N$^+$R$_{15}$R$_{16}$R$_{17}(C_a-C_b)$alkyl" and "N$^+$R$_{11}$R$_{11}$R$_{13}(C_a-C_b)$alkyl" wherein a and b are as above defined, refer to the above defined "$(C_a-C_b)$alkyl" groups wherein one hydrogen atom is replaced by one a group —N$^+$R$_{15}$R$_{16}$R$_{17}$ or N$^+$R$_{11}$R$_{11}$R$_{13}$ respectively.

The expressions "mono $(C_a-C_b)$alkyl amino" and "di $(C_a-C_b)$alkyl amino," wherein a and b are integers, refer to an amino group wherein, respectively, one or both hydrogen atoms are replaced by a group $(C_a-C_b)$alkyl.

The expression "phenyl$(C_a-C_b)$alkyl" refers to the above defined "$(C_a-C_b)$alkyl" radicals wherein one hydrogen atom is replaced by a phenyl group.

The term "divalent $(C_a-C_b)$alkylene radical" wherein a and b are integers refers to a saturated hydrocarbon chain having from a to b carbon atoms as above defined and two unsatisfied valences.

The term "$(C_a-C_b)$ cycloalkyl" wherein a and b are integers refers to saturated monocyclic, bicyclic or tricyclic hydrocarbon groups containing from a to b ring carbon atoms, as appropriate. Examples include cyclopropyl, cyclobutyl, cyclopentyl, cyclohexyl, cycloheptyl, and adamantyl.

As used herein, the unqualified term "heterocyclyl" or "heterocyclic" relates to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems, such as for example a quinuclidine ring. In particular, the term "$C_a-C_b$heterocycloalkyl" refers to monocyclic $(C_a-C_b)$cycloalkyl groups, in which at least one ring carbon atom is replaced by a heteroatom (e.g. N, NH, S, or O). Examples of $(C_a-C_b)$heterocycloalkyl include pyrrolidinyl, thiazolidinyl, piperazinyl, piperidinyl, morpholinyl, and thiomorpholinyl.

By analogy, the expression "heterocycloalkylene" refers to a divalent heterocyclic radical as above defined. In particular, the expression "$(C_a-C_b)$heterocycloalkylene" refers to a divalent $(C_a-C_b)$heterocycloalkyl radical (such as for example pyrrolidinene) wherein "$(C_a-C_b)$heterocycloalkyl group is as above defined.

The expression "heteroaryl" refers to mono or bi-cyclic ring systems with 5 to 11 ring atoms, in which at least one ring is aromatic and in which at least one ring atom is a heteroatom (e.g. N, NH, S, or O).

Examples of suitable 5 and 6-membered heteroaryl monocyclic systems include, for instance thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals and the like.

The term "$(C_a-C_b)$ alkoxyl" wherein a and b are integers refers to straight-chained and branched alkoxy groups wherein the number of constituent carbon atoms is in the range from a to b. Particular alkyl groups are methoxyl, ethoxyl, n-propoxyl, isopropoxyl, and t-butoxyl.

The symbol "—$C_6H_4$—" indicates a divalent phenylene ring radical.

The expression "$(C_a-C_b)$alkylcarbonyl" refers to —CO $(C_a-C_b)$alkyl groups wherein the group "$(C_a-C_b)$alkyl" has the meaning above defined.

The expression "$(C_a-C_b)$alkylhydroxyl" refers to the above defined "$(C_a-C_b)$alkyl" radicals wherein one hydrogen atom is replaced by one a group —OH.

Unless otherwise specified, the term "substituted" as applied to any moiety herein means substituted with up to four compatible substituents, each of which independently may be, for example, $(C_1-C_6)$alkyl, $(C_1-C_6)$alkoxyl, hydroxyl, hydroxyl-$C_1$-$C_6$-alkyl, halo (including fluoro, bromo and chloro), trifluoromethyl, and trifluoromethoxy. An "optional substituent" may be one of the foregoing substituent groups.

The term "salt" includes base addition and acid addition salts.

The term "pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

Compounds of the present invention which are acidic can form salts, including pharmaceutically acceptable salts, with bases such as alkali metal hydroxides, e.g. sodium and potassium hydroxides; alkaline earth metal hydroxides, e.g. calcium, barium and magnesium hydroxides; with organic bases, e.g. N-methyl-D-glucamine, choline tris(hydroxymethyl)amino-methane, L-arginine, L-lysine, N-ethyl piperidine, dibenzylamine and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids, e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. Those compounds which have quaternary nitrogen can also form quaternary salts with a pharmaceutically acceptable counter-ion such as chloride, bromide, acetate, formate, p-toluenesulfonate, succinate, hemi-succinate, naphthalene-bis sulfonate, methanesulfonate, xinafoate, and the like.

When the compounds of the present invention have at least one stereogenic center, they may exist as enantiomers. When the compounds according to the invention possess two or more stereogenic centers, they may additionally exist as diastereoisomers. It is to be understood that all such isomers and mixtures thereof in any proportion are encompassed within the scope of the present invention.

It will be apparent that compounds of general formula (I) contain at least one stereogenic center, namely represented by the carbon atom (1) with an asterisk below, and therefore exist as optical stereoisomers:

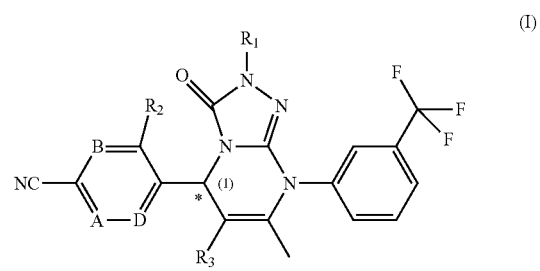

In one embodiment, the present invention is directed to compounds of formula (I)', which are compounds of formula (I) as above defined where the absolute configuration of carbon (1) is that shown here below:

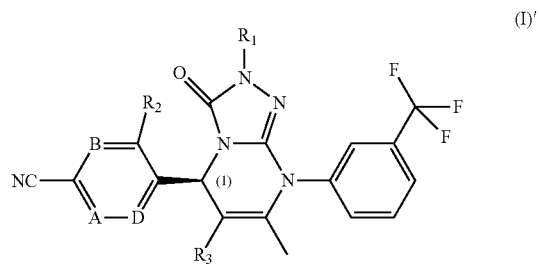

In another embodiment, the present invention is directed to compounds of formula (I)", which are compounds of formula (I) as above defined where the absolute configuration of carbon (1) is that shown herebelow:

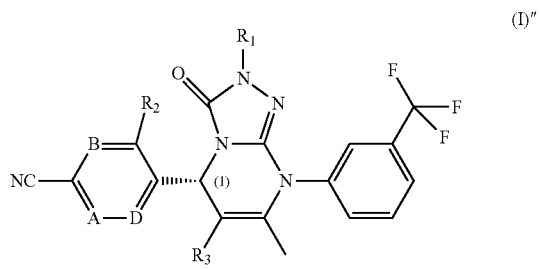

The absolute configuration for carbon (1) is assigned on the basis of Cahn-Ingold-Prelog nomenclature based on groups' priorities.

It is to be understood that all preferred groups or embodiments described here below for compounds of formula (I) may be combined among each other and apply as well to compounds of formula (I)', (I)", (IA) and (IB), mutatis mutandis.

In one embodiment, for formula (I) A is CH, B is CH, and D is CH.

In another embodiment, for formula (I) A is N, B is CH, and D is CH.

In a still another embodiment, for compounds of formula (I) A is CH, B is CH, and D is N.

In a further another embodiment, for compounds of formula (I) A is CH, B is N, and D is CH.

In a still further embodiment, for compounds of formula (I) A is N, B is N, and D is CH.

In an additional embodiment, for compounds of formula (I) A is N, B is CH, and D is N.

In one embodiment, for compounds of formula (I) when G is —(SO$_2$)—, y is 1.

In one embodiment, R$_2$ is selected from the group consisting of: NR$_{18}$R$_{19}$(C$_1$-C$_6$)alkyl and C$_2$-C$_6$-alkynyl which C$_2$-C$_6$-alkynyl is substituted by a group —OH or —NR$_{18}$R$_{19}$.

In another embodiment, R$_2$ is NR$_{18}$R$_{19}$(C$_1$-C$_6$)alkyl.

In a further embodiment, R$_2$ is a group —[CH$_2$]$_y$-G-[CH$_2$]$_j$—CH$_2$—N$^+$R$_{22}$R$_{23}$R$_{24}$.

In one embodiment, R$_3$ is a group cyano or a group —C(O)—XR$_4$. In a another embodiment, R$_3$ is a group —C(O)—XR$_4$.

In one embodiment, R$_4$ is optionally substituted (C$_1$-C$_6$) alkyl. In another embodiment, R$_4$ is (C$_1$-C$_6$)alkyl.

In one embodiment, X is a divalent group —O— or —NH—. In another embodiment, X is a divalent —O—.

In one embodiment, for compounds of formula (I), R$_1$ is hydrogen or a group —(CH$_2$)$_r$SO$_2$(C$_1$-C$_4$)alkyl. In another embodiment, R$_1$ is hydrogen.

In one embodiment, a compound of formula (IA) is provided

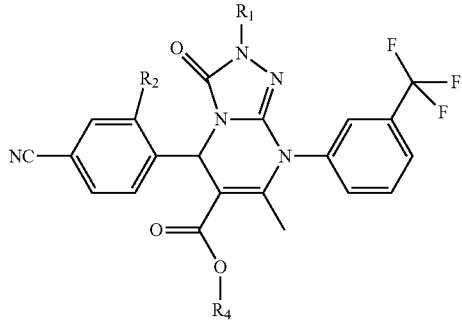

(IA)

wherein R$_3$ is —C(O)—XR$_4$ and the other groups R$_4$, R$_2$ and R$_1$ are as above defined. In one embodiment, for compounds of formula (IA) R$_1$ is hydrogen.

In another embodiment, a compound of the invention is selected from the group consisting of:

5-[4-Cyano-2-(4-hydroxy-but-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-Cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-Cyano-2-(3-dimethylamino-prop-1-ynyl)-phenyl]-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-Cyano-2-[2-(3-methanesulfonyl-propyl)-6-methoxycarbonyl-7-methyl-3-oxo-8-m-tolyl-2,3,5,8-tetrahydro-[1,2,4]triazolo[4,3-a]pyrimidin-5-yl]-phenyl}-prop-2-ynyl)-trimethyl-ammonium formate;

5-[4-Cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-Cyano-2-dimethylaminomethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

{5-Cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium bromide;

(2-{5-Cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzoylamino}-ethyl)-trimethyl-ammonium chloride;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium formate;

(R)-5-[4-Cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-prop-2-ynyl)-trimethyl-ammonium iodide;

(R)-5-[4-Cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium iodide;

and pharmaceutically acceptable salts thereof.

In a further embodiment, a compound of the invention is selected from the group consisting of:

5-[4-Cyano-2-(4-hydroxy-but-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-Cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-Cyano-2-(3-dimethylamino-prop-1-ynyl)-phenyl]-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-Cyano-2-[2-(3-methanesulfonyl-propyl)-6-methoxycarbonyl-7-methyl-3-oxo-8-m-tolyl-2,3,5,8-tetrahydro-[1,2,4]triazolo[4,3-a]pyrimidin-5-yl]-phenyl}-prop-2-ynyl)-trimethyl-ammonium formate;

5-[4-Cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-Cyano-2-dimethylaminomethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

{5-Cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium bromide;

(2-{5-Cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzoylamino}-ethyl)-trimethyl-ammonium chloride;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium formate;

(R)-5-[4-Cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-prop-2-ynyl)-trimethyl-ammonium iodide;

(R)-5-[4-Cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium iodide;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium iodide;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(3-methanesulfonyl-propyl)-dimethyl-ammonium formate;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-cyclopropylmethyl-dimethyl-ammonium formate;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(3-hydroxy-propyl)-dimethyl-ammonium formate;

(3-{5-Cyano-2-[(R)-6-methoxycarbonyl-7-methyl-3-oxo-8-(3-trifluoromethyl-phenyl)-2,3,5,8-tetrahydro[1,2,4]triazolo[4,3-a]pyrimidin-5-yl]-phenyl}-propyl)-(3-methoxy-propyl)-dimethyl-ammonium formate:

(3-{5-Cyano-2-[(R)-6-methoxycarbonyl-7-methyl-3-oxo-8-(3-trifluoromethyl-phenyl)-2,3,5,8-tetrahydro[1,2,4]triazolo[4,3-a]pyrimidin-5-yl]-phenyl}-propyl)-dimethylcarbamoylmethyl-dimethyl-ammonium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-1-azonia-bicyclo[2.2.2]octane formate;

1-(3-{5-Cyano-2-[(R)-6-methoxycarbonyl-7-methyl-3-oxo-8-(3-trifluoromethyl-phenyl)-2,3,5,8-tetrahydro[1,2,4]triazolo[4,3-a]pyrimidin-5-yl]-phenyl}-propyl)-4-aza-1-azonia-bicyclo[2.2.2]octane formate;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(4-hydroxy-cyclohexyl)-dimethyl-ammonium formate;

4-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-4-methyl-morpholin-4-ium formate;

Adamantan-1-yl-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-ammonium formate;

4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-morpholin-4-ium formate;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-hydroxy-propyl)-dimethyl-ammonium formate;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-ethyl-dimethyl-ammonium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-azonia-bicyclo[2.2.2]octane formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1,4-dimethyl-piperazin-1-ium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(4-hydroxy-cyclohexyl)-dimethyl-ammonium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-aza-1-azonia-bicyclo[2.2.2]octane formate;

1-{2-[(R)-6-carboxy-7-methyl-3-oxo-8-(3-trifluoromethyl-phenyl)-2,3,5,8-tetrahydro-[1,2,4]triazolo[4,3-a]pyrimidin-5-yl]-5-cyano-benzyl}-4-aza-1-azonia-bicyclo[2.2.2]octane formate;

Butyl-{5-cyano-2-[(R)-6-methoxy carbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-ammonium formate;

1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-hydroxy-1-methyl-piperidinium formate;

1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-methyl-pyrrolidinium formate;

1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-methyl-piperidinium formate;

1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-(2-hydroxy-ethyl)-pyrrolidinium formate;

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-dimethylcarbamoyl-propyl)-dimethyl-ammonium formate;

Benzyl-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-ammonium formate;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethylammonium bromide;

(S)-5-[4-Cyano-2-(5-hydroxypentyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethylammonium benzenesulfonate;

(5-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-pentyl)-trimethylammonium formate;

(4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-trimethyl-ammonium formate;

1-(4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-1-azoniabicyclo[2.2.2]octane formate;

1-(4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-1-azoniabicyclo[2.2.2]octane formate;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium bromide;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium bromide;

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium bromide;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium benzenesulfonate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium chloride;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium 2-hydroxy-ethanesulfonate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium methanesulfonate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-hydroxymethyl-pyridinium tosylate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-methyl-pyridinium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-2-methyl-pyridinium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-hydroxymethyl-pyridinium formate;

3-Chloro-1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium formate;

Butyl-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-ammonium formate;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclohexyl-dimethyl-ammonium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-methyl-pyrrolidinium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-methyl-piperidinium formate;

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-hydroxy-1-methyl-piperidinium formate;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-oxetan-3-yl-ammonium formate;

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-(tetrahydro-pyran-4-yl)-ammonium formate;

4-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-methyl-morpholin-4-ium formate;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethylcarbamoylmethyl-dimethyl-ammonium formate;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(3-methoxypropyl)-dimethyl-ammonium formate;

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclobutylmethyl-dimethyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-(tetrahydro-pyran-4-ylmethyl)-ammonium formate;
1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-(2-hydroxy-ethyl)-pyrrolidinium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-[2-(2-hydroxy-ethoxy)-ethyl]-dimethyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-bis-(2-hydroxy-ethyl)-methyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(2-hydroxy-ethyl)-dimethyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-ethyl-dimethyl-ammonium formate;
Benzyl-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclohexylmethyl-dimethyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(3-hydroxypropyl)-dimethyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-diethyl-methyl-ammonium formate;
(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclopropylmethyl-dimethyl-ammonium formate;
1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-azoniabicyclo[2.2.2]octane formate;
1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-hydroxymethyl-pyridinium formate;
1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-methyl-pyridinium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-cyclobutylmethyl-dimethyl-ammonium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(tetrahydro-pyran-4-ylmethyl)-ammonium formate;
{{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(2-methoxy-ethyl)-dimethyl-ammonium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-cyclopropylmethyl-dimethyl-ammonium formate;
3-Chloro-1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(2-hydroxy-ethyl)-dimethyl-ammonium formate;
1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methoxy-pyridinium formate;
1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-3-hydroxymethyl-pyridinium formate;
{1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-hydroxymethyl-1-methyl-piperidinium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-ethoxycarbonylmethyl-dimethyl-ammonium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(1,1-dioxo-hexahydro-1lambda*6*-thiopyran-4-ylmethyl)-dimethyl-ammonium formate;
1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-3,4-dihydroxy-1-methyl-pyrrolidinium formate;
4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-ethyl-morpholin-4-ium formate;
1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-dimethylcarbamoyl-1-methyl-piperazin-1-ium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethylcarbamoylmethyl-dimethyl-ammonium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(1-methanesulfonyl-piperidin-4-yl)-dimethyl-ammonium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-oxetan-3-ylmethyl-ammonium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(3-methylcarbamoyl-propyl)-ammonium formate;
{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-dimethylsulfa-
moyl-propyl)-dimethyl-ammonium formate
1-{5-Cyano-2-[(R)-6-methoxycarbonyl-7-methyl-3-oxo-
8-(3-trifluoromethyl-phenyl)-2,3,5,8-tetrahydro-[1,2,4]tria-
zolo[4,3-a]pyrimidin-5-yl]-benzyl}-4-methanesulfonyl-1-
methyl-piperazin-1-ium formate;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-bis-(2-hydroxy-
ethyl)-methyl-ammonium formate;
1-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-4,4-difluoro-1-me-
thyl-piperidinium formate;
4-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-4-methyl-[1,4]ox-
azepan-4-ium formate;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-(3-methoxy-propyl)-
dimethyl-ammonium formate;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-(3-methanesulfonyl-
propyl)-dimethyl-ammonium formate;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-dimethyl-(1-methyl-
piperidin-4-yl)-ammonium formate;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-dimethyl-piperidin-
4-yl-ammonium formate;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-dimethyl-(tetrahy-
dro-pyran-4-yl)-ammonium formate;
1-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-pyridinium bromide;
1-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-pyridinium benzene-
sulphonate;
1-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-pyridinium tosylate;
Benzyl-{5-cyano-2-[(R)-6-methoxycarbonyl-7-methyl-3-
oxo-8-(3-trifluoromethyl-phenyl)-2,3,5,8-tetrahydro-[1,2,
4]triazolo[4,3-a]pyrimidin-5-yl]-benzyl}-dimethyl-am-
monium bromide;
Benzyl-{5-cyano-2-[(R)-6-methoxycarbonyl-7-methyl-3-
oxo-8-(3-trifluoromethyl-phenyl)-2,3,5,8-tetrahydro-[1,2,
4]triazolo[4,3-a]pyrimidin-5-yl]-benzyl}-dimethyl-am-
monium benzenesulfonate;
4-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-4-methyl-morpholin-
4-ium bromide;
4-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-4-methyl-morpholin-
4-ium bromide;
4-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-4-methyl-morpholin-
4-ium bromide;
4-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-4-methyl-morpholin-
4-ium bromide;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-trimethyl-ammonium
benzenesulfonate;
1-(2-{5-Cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-phenyl}-ethyl)-pyridinium
2-hydroxy-ethanesulfonate;
1-(2-{5-Cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-phenyl}-ethyl)-pyridinium
methanesulfonate;
1-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-benzyl}-pyridinium chloride;
{5-Cyano-2-[(R)-6-methoxycarbonyl-7-methyl-3-oxo-8-(3-
trifluoromethyl-phenyl)-2,3,5,8-tetrahydro-[1,2,4]tria-
zolo[4,3-a]pyrimidin-5-yl]-benzyl}-bis-(2-hydroxy-
ethyl)-methyl-ammonium benzenesulfonate;
1-(2-{5-Cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-phenyl}-ethyl)-pyridinium
benzenesulfonate;
(2-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-phenyl}-ethyl)-trimethyl-am-
monium 2-hydroxy-ethanesulfonate;
(2-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-phenyl}-ethyl)-trimethyl-am-
monium methanesulfonate;
(2-{5-Cyano-2-[(R)-6-methoxycarbonyl-7-methyl-3-oxo-8-
(3-trifluoromethyl-phenyl)-2,3,5,8-tetrahydro-[1,2,4]tria-
zolo[4,3-a]pyrimidin-5-yl]-phenyl}-ethyl)-trimethyl-am-
monium chloride;
and pharmaceutically acceptable salts thereof.

The therapeutic utility of the present compounds is pertinent to any disease that is known to be at least partially mediated by the action of human neutrophil elastase. For example, the present compounds may be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention also provides pharmaceutical formulations comprising, as an active ingredient, a compound of the invention. Other compounds may be combined with compounds of this invention for the prevention and treatment of inflammatory diseases of the lung. Thus, the present invention also provides pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocoritisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) a expectorant/mucokinetic modulator, for example ambroxol, hypertonic solutions (e.g. saline or mannitol) or surfactant; (10) a peptide mucolytic, for example recombinant human deoxyribonoclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (12) inhibitors of Janus Kinases (JAK) such as CP-690550 or GLPG0634; (13) Spleen Tyrosine Kinase (SYK) inhibitors such as R406, R343 or PRT062607; (14) inhibitors of delta and/or gamma isoforms of Phosphatidylinositol 3-kinase (PI3K); (15) anti-retroviral agents such as ribavirin, zanamivir or laninamivir; (16) PPAR-γ agonists such as pioglitazone and rosiglitazone.

In one aspect, the present invention provides for the use of inhaled administration of compounds of the invention in combination with other anti-inflammatory drugs and bronchodilator drug combinations (i.e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, arformoterol tartrate/ciclesonide.

In another aspect, the present invention provides for the use of inhaled administration of compounds of the invention in combination with other bronchodilator drug combinations, particularly $\beta_2$ agonist/$M_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacaterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients may be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a compound of the invention, additional active ingredient(s), and pharmaceutically acceptable excipients.

The pharmaceutical compositions of the invention comprise a compound of the present invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and may include carriers and/or diluents that are known for use in such compositions. The composition may contain 0.01 to 99% by weight of active compound. Preferably, a unit dose comprises the active compound in an amount of 1 μg to 10 mg.

The most suitable dosage level may be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They may be prepared by a variety of techniques, including spray-drying, freeze-drying and micronization.

By way of example, a composition of the invention may be prepared as a suspension for delivery from a nebulizer or as an aerosol in a liquid propellant, for example for use in a pressurized metered dose inhaler (PMDI). Propellants suitable for use in a PMDI are known to the skilled person, and include CFC-12, HFA-134a, HFA-227, HCFC-22 ($CCl2F2$) and HFA-152 ($CH4F2$ and isobutane).

In a preferred embodiment of the invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, a preferred composition is:

Compound of the invention 24 mg/canister
Lecithin, NF Liq. Conc. 1.2 mg/canister
Trichlorofluoromethane, NF 4.025 g/canister
Dichlorodifluoromethane, NF 12.15 g/canister.

Compounds of the present invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the present invention is used contemporaneously with one or more other drugs, a pharmaceutical composition containing such other drugs in addition to the compound of the present invention is preferred. Accordingly, the pharmaceutical compositions of the invention include those that also contain one or more other active ingredients, in addition to a compound of the invention.

The agents of the invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

Methods of Synthesis:

In one aspect of the present invention, a process for the preparation of compounds of the invention (Ia), i.e. compounds of formula (I) wherein $R_1$ is hydrogen and $R_3$ is —$COXR_4$, and of compounds of the invention of formula (Ib), i.e. compounds of formula (I) wherein $R_1$ is not hydrogen and $R_3$ is —$COXR_4$, is provided, according to general synthetic routes reported in Scheme A here below.

Scheme A.

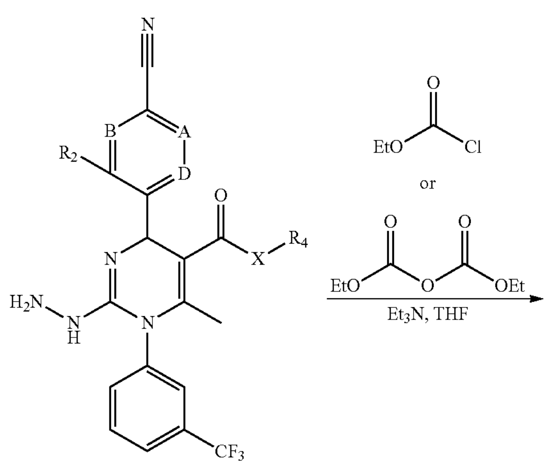

(III)

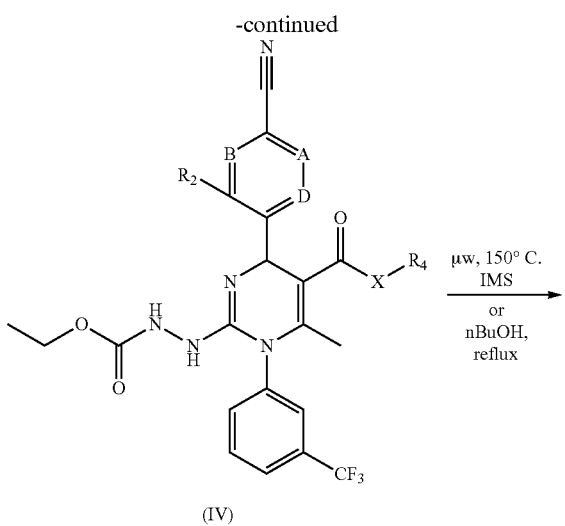

(IV)

Compounds of formula (IV) may be prepared from compounds of formula (III) by reaction with ethyl chloroformate (or ethyl pyrocarbonate) in the presence of a base such as triethylamine in a solvent such as THF at a temperature of from 0° C. to reflux. Compounds of formula (IV) may be transformed into compounds of formula (Ia) by heating in an appropriate solvent. Suitable conditions include the use of a solvent such as IMS and heating using microwave irradiation at a temperature of up to 150° C. or conventional heating in a solvent such as n-butanol at reflux. Compounds of formula (Ia), as above defined, may be converted into compounds of formula (Ib), as above defined, by reaction with an alkyl halide (VI) of formula $R_1$—X' wherein X' is an appropriate leaving group (X'=Cl, Br, I, Tosylate etc.) in a solvent such as DMF in the presence of a base such as cesium carbonate at a temperature of from room temperature to 100° C. Alternatively, the transformation may be achieved by Mitsunobu reaction with an alcohol (VII) of formula $R_1$OH. Typical reagents employed are triphenyl phosphine and DIAD in a solvent such as THF.

Compounds of formula (III) wherein $R_4$ is $(C_1$-$C_6)$alkyl, may be prepared according to Scheme B below:

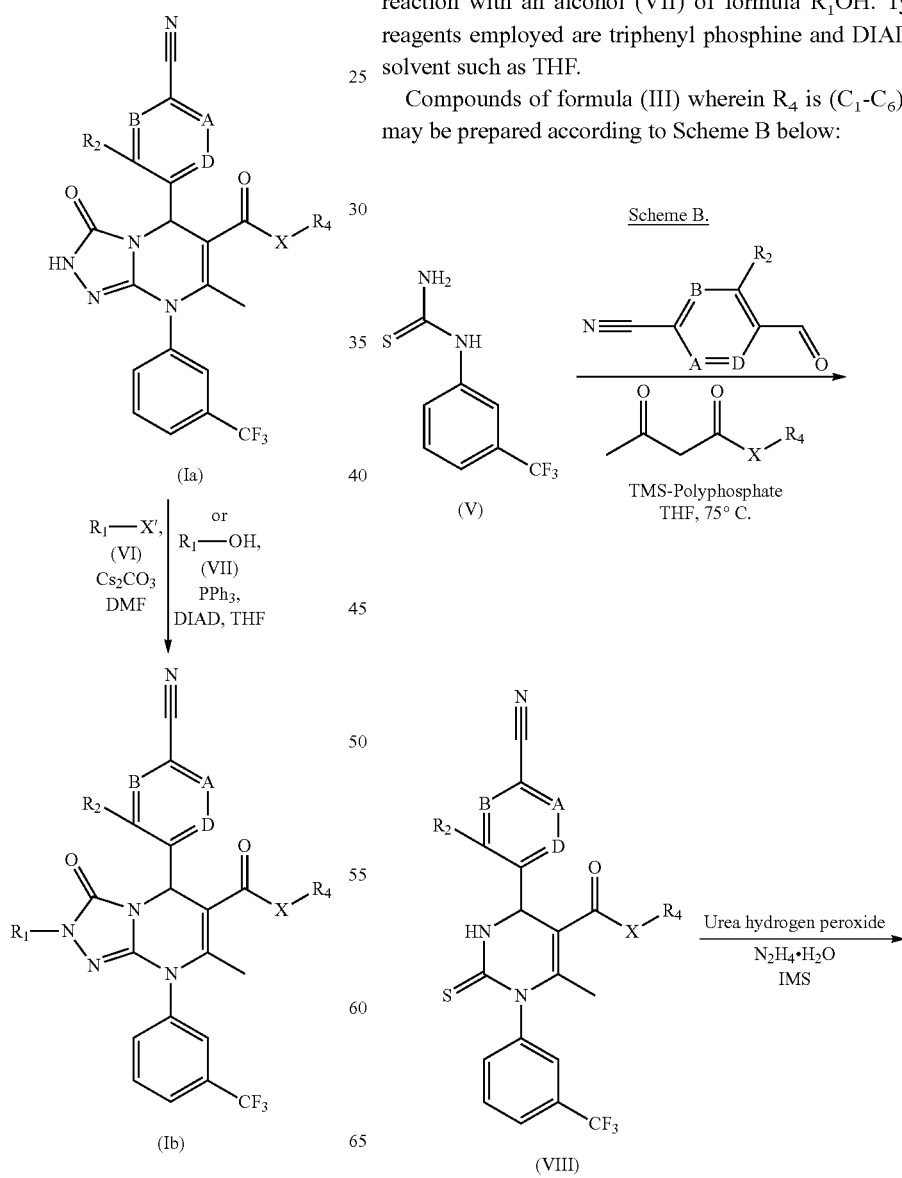

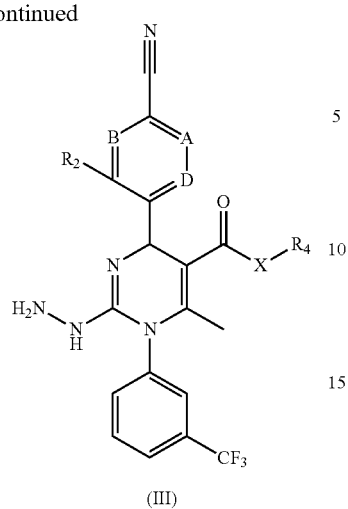

(III)

Compounds of formula (V) may be reacted with a benzaldehyde such as 3-bromo-4-formyl-benzonitrile and an acetoacetate such as ethyl acetoacetate in the presence of an acid such as TMS-polyphosphate in a solvent such as THF at a temperature of from room temperature to reflux to give compounds of formula (VIII), wherein $R_4$ is $(C_1-C_6)$alkyl and the other groups are as define for compounds of formula (I). Compounds of formula (III) may be prepared from compounds of formula (VIII) by reaction with an oxidizing agent such as urea hydrogen peroxide followed by in-situ treatment with hydrazine hydrate in IMS.

Furthermore compounds of formula (I)', which are compounds of formula (I) as above defined where the absolute configuration of carbon (1) is that shown below can be prepared according to Scheme C.

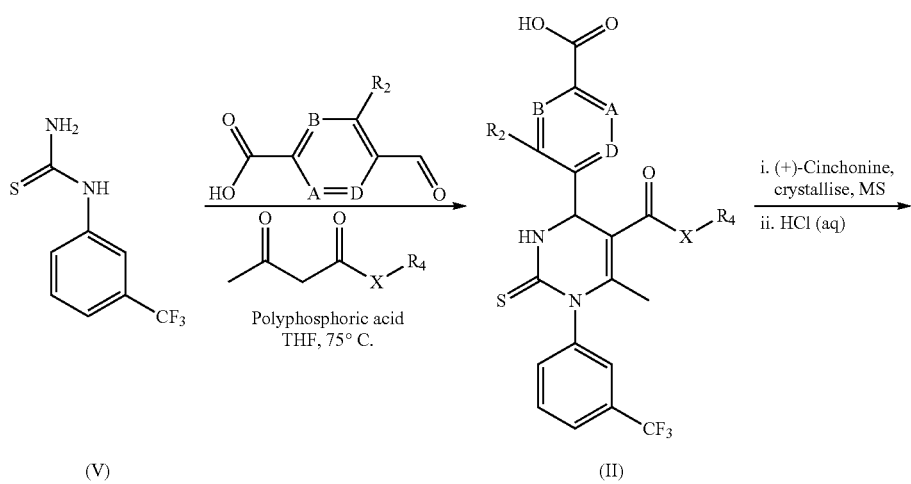

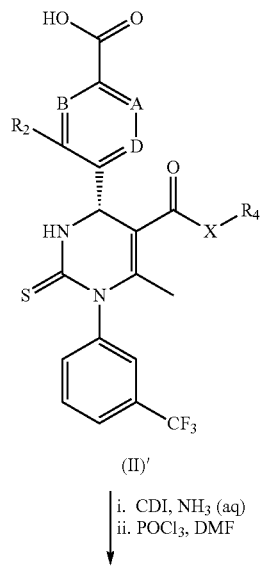

-continued

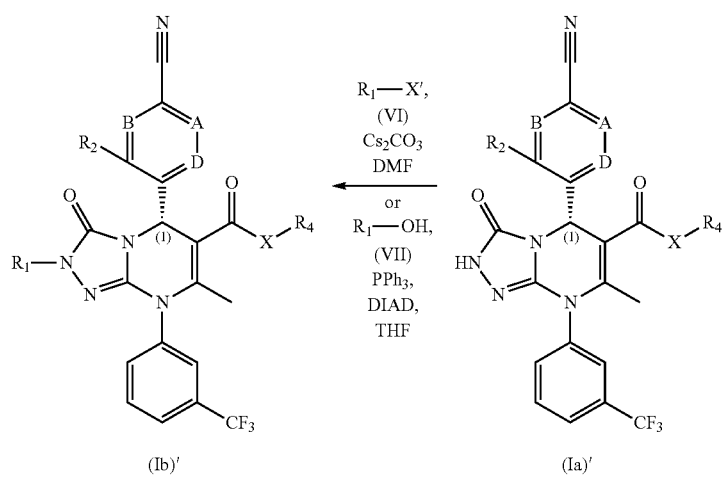

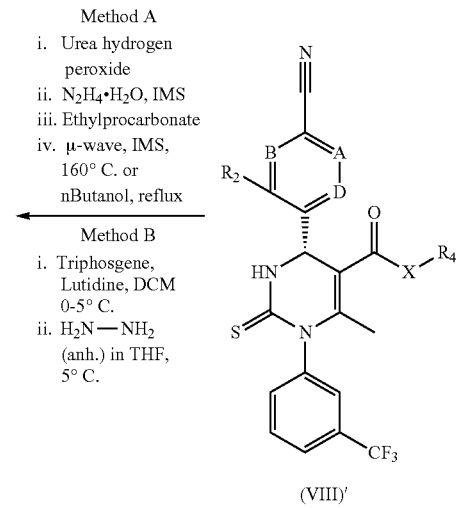

Compounds of formula (II) may be obtained from compounds of formula (V) by reacting with 3-bromo-4-formylbenzoic acid using a similar method described for the transformation of compounds of formula (V) to compounds of formula (VIII) in Scheme B. Compounds of formula (II)', which are compounds of formula (II) wherein the absolute configuration at stereogenic center (1) is as reported in Scheme C, may be obtained from compounds of formula (II) by forming a chiral diastereomeric salt with a suitable chiral amine such as (+)-Cinchonine in a suitable solvent such as dioxane, followed by treatment of the salt with an acid such as hydrochloric acid to give the enantiomerically pure compounds of formula (II)'. Compounds of formula (VIII)', which are compounds of formula (VIII) wherein the absolute configuration at stereogenic center (1) is as reported in Scheme C, may be prepared from compounds of formula (II)' by reaction with aqueous ammonia in the presence of a coupling agent such as carbonyl diimidiazole in a solvent such as THF at a temperature of from 0° C. to room temperature to give the intermediate primary amide. Conversion of the amide to compounds of formula (VIII)' may be undertaken using a dehydrating agent. Suitable conditions include the use of a solvent such as DMF and a dehydrating agent such as phosphorus oxychloride at a temperature of from 0° C. to room temperature.

Compounds of formula (Ia)' and (Ib)', which are compounds of formula (Ib) and (Ia) as above defined and wherein the absolute configuration of carbon (1) is that shown in Scheme C (Method A), may be obtained from compounds of formula (VIII)' using similar methods described for the transformation of compounds of formula (VIII) to compounds of formula of formula (Ia) and (Ib) in Schemes B and A. Alternatively, compounds of formula (Ia)' and (Ib)', which are compounds of formula (Ib) and (Ia) as above defined and wherein the absolute configuration of carbon (1) is that shown in Scheme C may be also be obtained from compounds of formula (VIII)' using method B; wherein compounds of formula (VIII)' may be reacted with a chlorocarbonyl-containing/releasing compound such as phosgene or triphosgene and anhydrous hydrazine in the presence of a base such as 2,6-lutadine in a solvent such as dichlromethane at a temperature of from −5-5° C. to give compounds of formula (Ia)' wherein $R_4$ is $(C_1-C_6)$alkyl and the other groups are as define for compounds of formula (I).

The skilled person would understand that by selecting of the appropriate chiral amine and its absolute configuration, derivatives of formula (II)", (VIII)", (Ib)" and (Ia)" [which are compounds of formula (II), (VIII), (Ib) and (Ia) respectively wherein the absolute configuration at stereogenic center (1) is opposite to that reported in Scheme C] may be obtained.

The skilled person may introduce, where appropriate, suitable variations to the conditions specifically described in the examples in order to adapt the synthetic routes to the provision of further compounds of the invention. Such variations may include, but are not limited to, use of appropriate starting materials to generate different compounds, changes in the solvent and temperature of reactions, replacement of reactants with analogous chemical role, introduction or removal of protection/de-protection stages of functional groups sensitive to reaction conditions and reagents, as well as introduction or removal of specific synthetic steps oriented to further functionalization of the chemical scaffold.

Processes which can be used and are described and reported in Examples should not be viewed as limiting the scope of the synthetic methods available for the preparation of the compounds of the invention.

Compounds used as starting materials or intermediates may be commercially available, their preparation may be specifically described in the literature, or they may be prepared according to methods available in the literature and well known to the person skilled in the art.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the Intermediates and Examples and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to.

Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981) which is incorporated herein by reference in its entirety).

Likewise, selective protection and de-protection of any of the said groups, for instance including carbonyl, hydroxyl or amino groups, may be accomplished according to very well-known methods commonly employed in organic synthetic chemistry.

Optional salt formation of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

The diastereoisomers of compounds of formula (I), where available, may be obtained according to methods well known in the art, such as for example by preparative HPLC or by chromatographic purifications. A racemic mixture of compounds of formula (I) may as well be separated using preparative HPLC and a column with a chiral stationary phase, or resolved to yield individual enantiomers using methods well known in the art. Furthermore, chiral intermediates may be resolved and used to prepare chiral compounds of the invention.

From all of the above, it should be clear to the skilled person that the above process, comprehensive of any variant thereof for the preparation of suitable compounds of the invention, may be conveniently modified so as to adapt the reaction conditions to the specific needs, for instance by choosing appropriate condensing agents, solvents and protective groups, as the case may be.

Compounds of formula (XII), wherein $R_3$ is a group —$COXR_4$, $R_1$ is as defined above, A, B and D are CH and $R_2$ is bromine or other suitable activating group taken from the group, but not exclusively, Cl, I, OTf, may be prepared from compounds of formula (IX) according to Scheme D here below reported:

Scheme D.

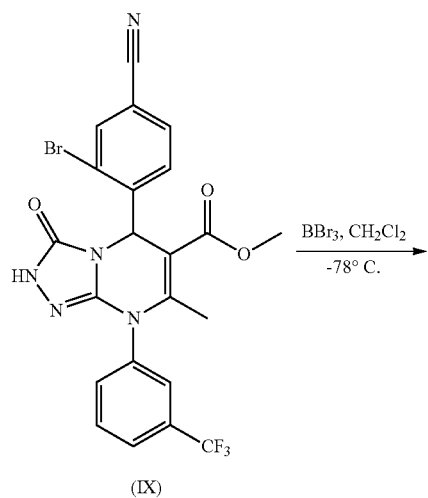

(IX)

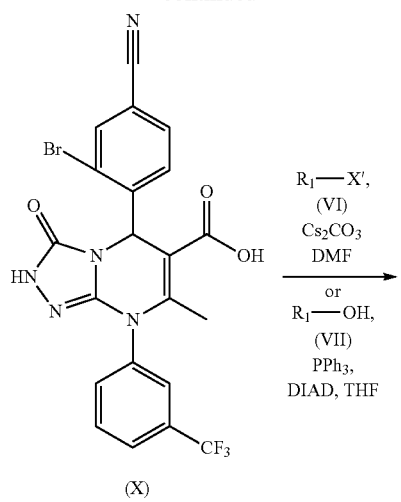

(X)

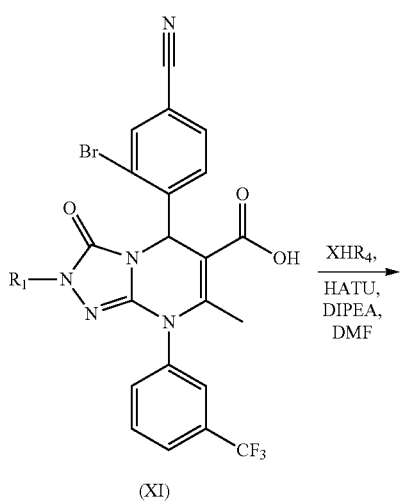

(XI)

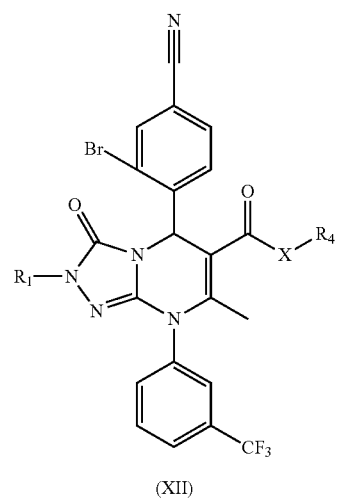

(XII)

Treatment of a compound of formula (IX) with a strong Lewis acid such as boron tribromide in a solvent such as DCM at a temperature of from −78° C. to room temperature followed by quench with water or methanol can provide compounds of formula (X).

It should be clear to the skilled person that other appropriate protecting group strategies may be contemplated and that the acid (X) represents a versatile intermediate for further functionalization as well as for preparation of compounds of formula (XII).

It is in fact to be underlined that many of the synthetic routes described below starting from compounds of formula (IX) (i.e. in Schemes F, G, and H) may be applicable, as the skilled person would understand, to compounds of formula (X) and (XII) also, to get to additional compounds of formula (I), (Ia), and (Ib).

By way of example, by appropriate derivatization of a compound of formula (X), as above defined, into a compound of formula (XI) wherein $R_1$ is not hydrogen, corresponding compounds of formula (XII) wherein $R_1$ is not hydrogen may be obtained. Compounds of formula (XI) may be obtained from compounds of formula (X) using the methods described for the transformation of compounds of formula (Ia) to compounds of formula (Ib) in Scheme A.

Compounds of formula (XII) may be prepared from compounds of formula (XI) by reaction with an alcohol or amine $XHR_4$ such as ammonia or 2-methoxy-ethanol in the presence of a coupling agent such as HATU in a solvent such as DMF in the presence of a base such as triethylamine at a temperature of from room temperature to 80° C. The synthetic route shown in Scheme D would be of benefit in introducing —$XR_4$ substituents at a late stage.

Scheme E.

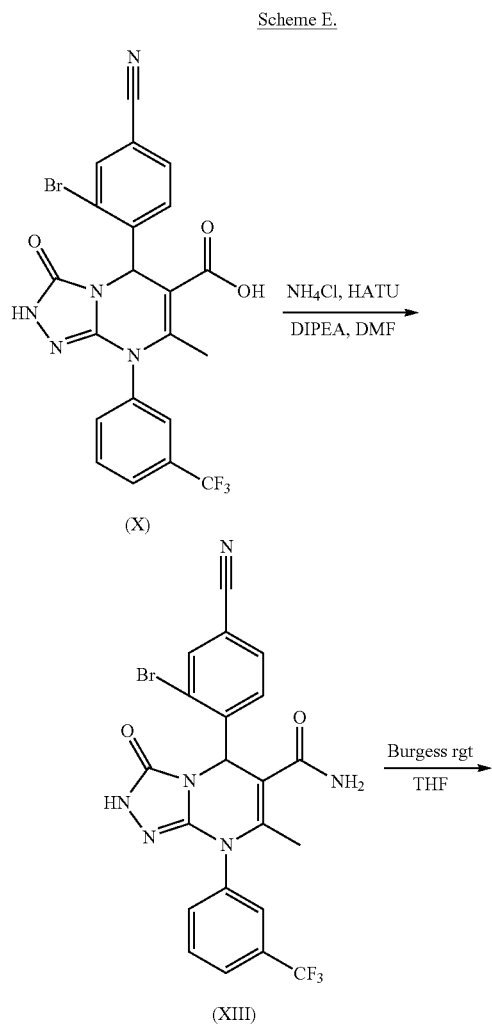

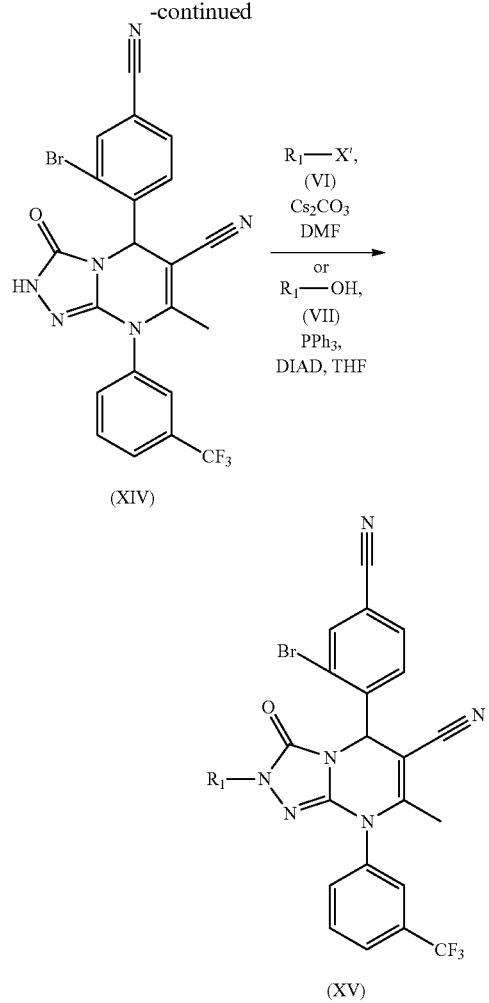

Compounds of formula (XIV) and (XV), i.e. compounds of formula (XII) wherein $R_3$ is a group —CN, may be prepared according to Scheme E from compounds of formula (X). Compounds of formula (XIII), which are compounds of formula (XII) wherein $R_1$ is H and $XR_4$ is $NH_2$, may be prepared by reaction with ammonia in the presence of a coupling agent such as HATU in a solvent such as DMF in the presence of a base such as triethylamine at a temperature of from room temperature to 80° C.

Compounds of formula (XIV) may be prepared from compounds of formula (XIII) by reaction with a dehydrating agent such as Burgess reagent in a solvent such as THF at a temperature of from room temperature to reflux. Compounds of formula (XV) may be obtained from compounds of formula (XIV) using the methods described for the transformation of compounds of formula (Ia) to compounds of formula (Ib) in Scheme A.

It will then be apparent to the skilled person that by adaptation of synthetic routes described below in schemes F or G and starting from compounds of formula (XIV) or (XV), compounds of formula (Im), i.e. compounds of formula (I) wherein $R_3$ is a group cyano, may be prepared.

Compounds of formula (Ic), (Id), (Ie) and (If), i.e. compounds of formula (I) wherein $R_3$ is a group —$COXR_4$, X is oxygen, $R_4$ is a methyl group, $R_1$ is as defined above, A, B and D are CH and $R_2$ is respectively a group as reported in Scheme F where $R_y$ may assume different meanings according to those described for compounds of formula (I), may be prepared from compounds of formula (IX) according to Scheme F here below reported:

Scheme F.
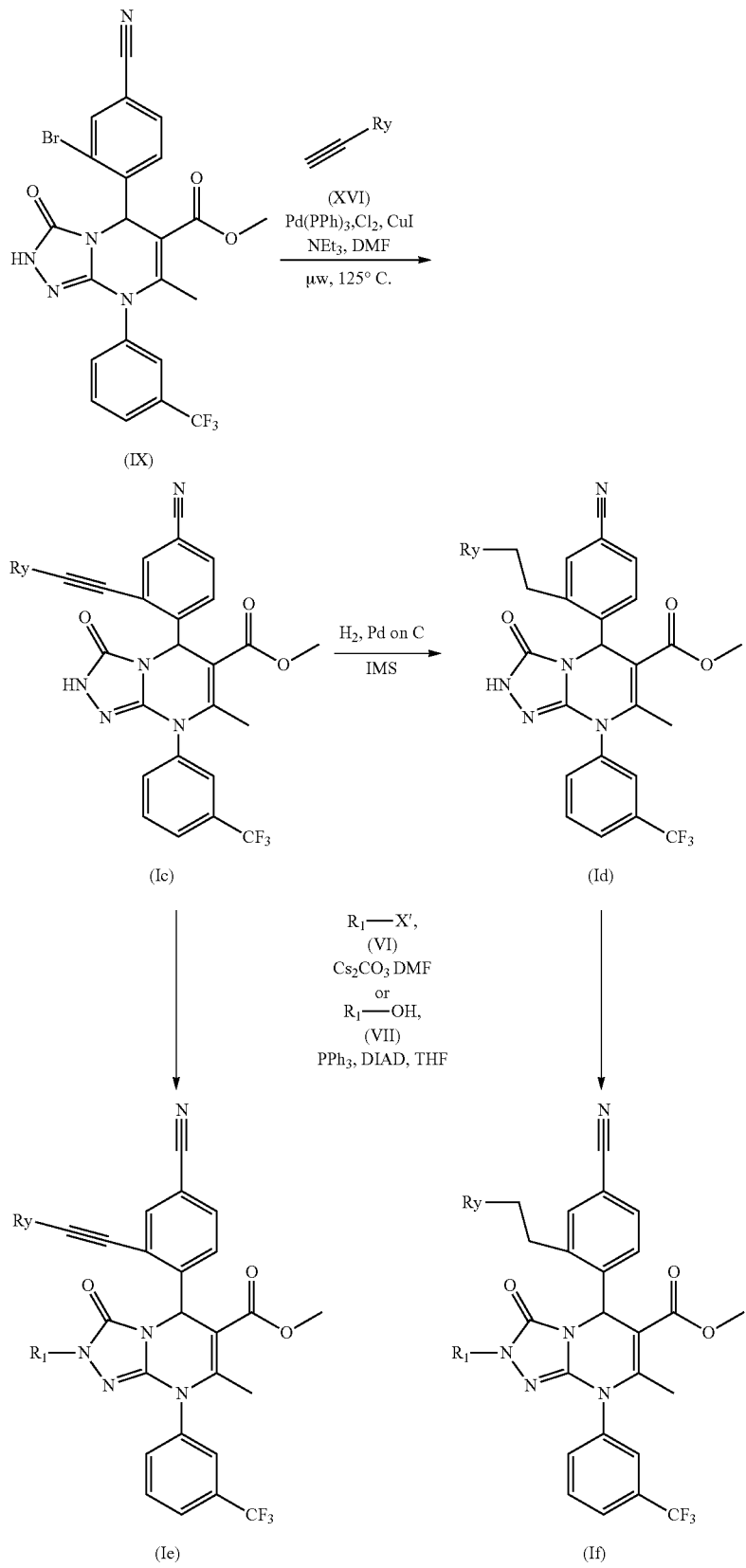

The transformation of compounds of formula (IX) into compounds of formula (Ic) may be achieved by reaction with a suitably unsubstituted acetylic compound (XVI) in the presence of a catalytic mixture such as bis(triphenylphosphine)palladium(II) dichloride and copper (1) iodide with a base such as triethylamine in a solvent such as DMF at a temperature of up to 120° C., typically using microwave irradiation. Compounds of formula (Id) may be prepared from compounds of formula (Ic) by hydrogenation using a catalyst such as Pd/C in a solvent such as IMS.

Furthermore, compounds of the formula (Ie) and (If) may be obtained from compounds of formula (Ic) and (Id), respectively, using the methods described for the transformation of compounds of formula (Ia) to compounds of formula (Ib) in Scheme A.

Compounds of formula (Ig) i.e. compounds of formula (I) wherein $R_3$ is a group —$COXR_4$, $R_1$ is as defined above, X is oxygen, $R_4$ is a methyl group, A, B and D are CH and $R_2$ is a methylene linked tertiary amine $NR_{18}R_{19}$ or quaternary amine $NR_{22}R_{23}R_{24}$ may be prepared from compounds of formula (IX) according to Scheme G below:

Scheme G.

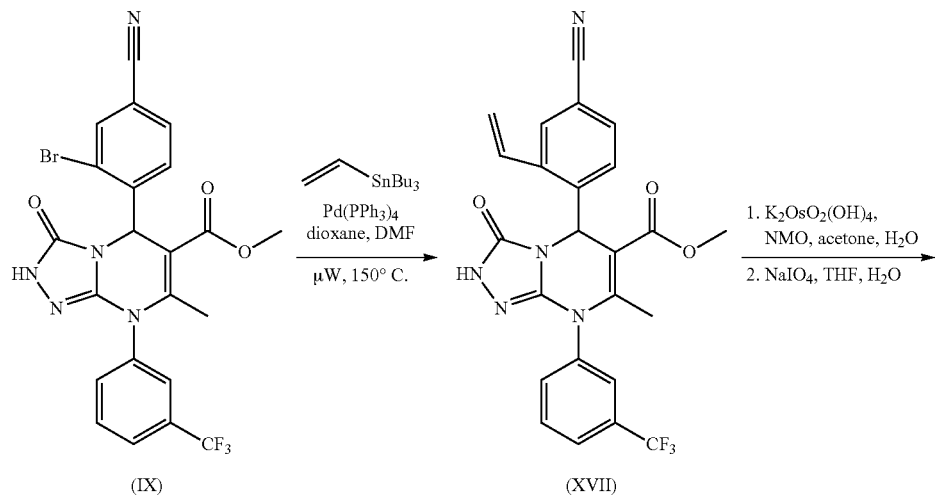

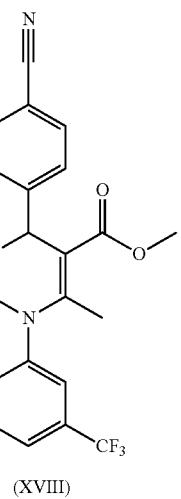

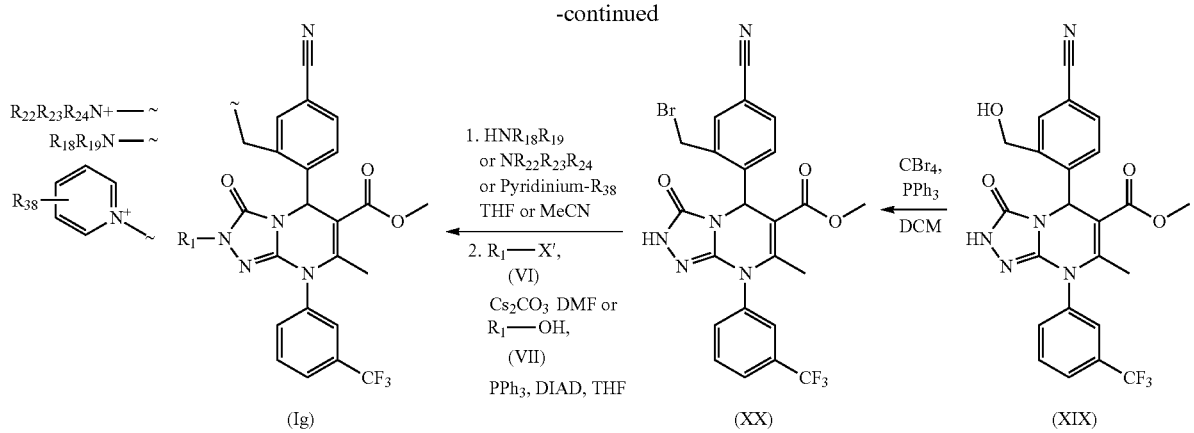

(Ig)                          (XX)                        (XIX)

The transformation of compounds of formula (IX) into compounds of formula (XVII) may be achieved by reaction with a suitable nucleophile such as vinyltributyl stannane in the presence of a catalyst such tetrakis(triphenylphosphine)palladium(0) in a solvent such as dioxane or DMF at a temperature of up to 150° C., typically using microwave irradiation. Compounds of formula (XVIII) may be prepared from compounds of formula (XVII) following a 2 step procedure starting with oxidation using a catalyst such as potassium osmate dihydrate with a co-oxidant such as N-methylmopholine-N-oxide in a solvent mixture such as acetone/water at room temperature. Compounds of formula (XVIII) are thus obtained following cleavage of the intermediate diol using a suitable reagent such as sodium periodate in an appropriate solvent mixture such as THF/water. Compounds of formula (XIX) may be obtained from compounds of formula (XVIII) by reduction, typically using a reducing agent such as sodium borohydride in a solvent such as MeOH. Compounds of formula (XX) may be obtained from compounds of formula (XIX) by bromination. Suitable conditions involve reaction with an appropriate brominating agent such as carbon tetrabromide with triphenyl phosphine in a solvent such as dichloromethane at a temperature of from 0° C. to room temperature. Conversion of compounds of formula (XX) to either tertiary or quaternary amines of formula (Ig) can be achieved by reaction with a suitable secondary amine of formula $NHR_{18}R_{19}$ or tertiary amine of formula $NR_{22}R_{23}R_{24}$, respectively, in a suitable solvent such as THF or MeCN. Alternatively, quaternary amines of the formula (Ig) may be obtained sequentially from tertiary amines of formula (Ig) followed by reaction with a suitable electrophile such as methyl bromide in a suitable solvent such as MeCN at room temperature. Furthermore, conversion of compounds of formula (XX) to pyridinum compounds of formula (Ig) can be achieved by reaction with a suitably substituted pyridine-containing compound, pyridine (R38).

It should be clear to the skilled person that the aldehyde (XVIII) represents a versatile intermediate for further functionalization as well as for preparation of compounds of formula (Ig).

Compounds of formula (Ih), i.e. compounds of formula (I) wherein $R_3$ is a group —$COXR_4$, $R_1$ is as defined above, A, B and D are CH, X is oxygen, $R_4$ is a methyl group, and $R_2$ is an amide-linked group as reported in Scheme H where $R_x$ may assume different meanings according to those described for compounds of formula (I), may be prepared from compounds of formula (XVIII) according to Scheme H below:

Scheme H.

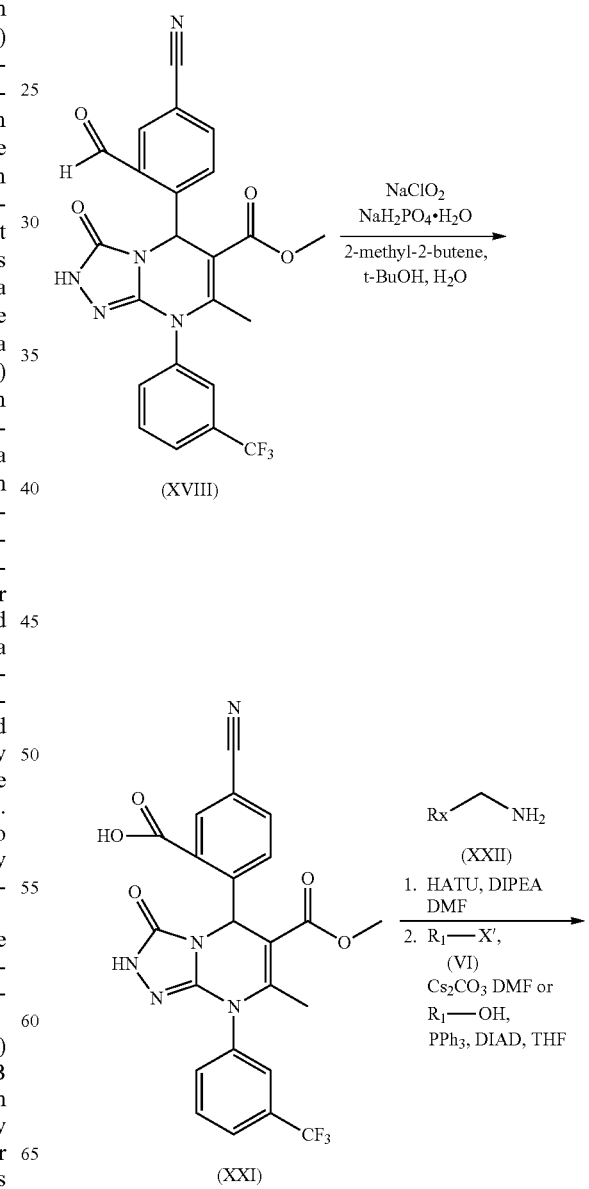

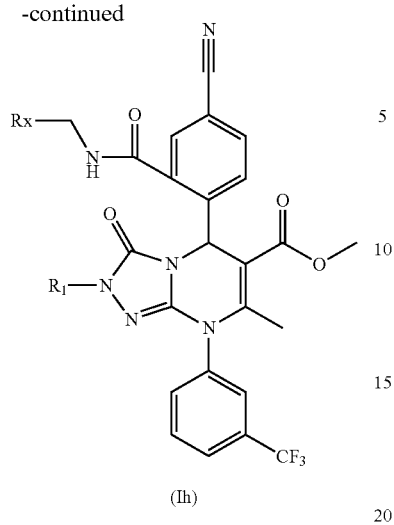

(Ih)

Scheme J.

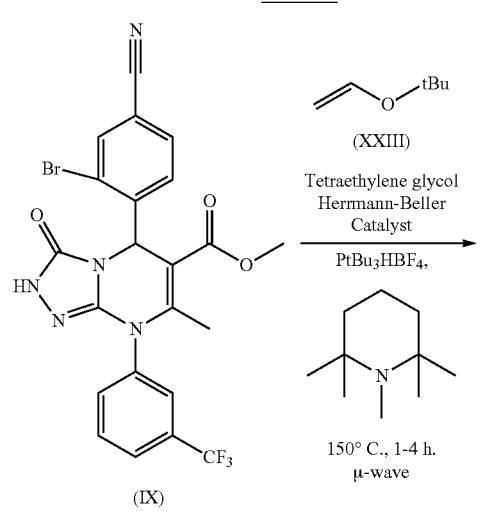

Compounds of formula (XXI) may be prepared from compounds of formula (XVIII) using suitable oxidizing reagent agent such as sodium chlorite and an appropriate co-reductant such as 2-methyl-2-butene in a suitable solvent mixture such as tert-butanol/water and using an appropriate base such as sodium dihydrogenphosphate at room temperature. Typically, compounds of formula (Ih) where R₁=H may be obtained from compounds of formula (XXI) by reaction with an amine (XXII) in the presence of a coupling agent such as HATU in a solvent such as DMF in the presence of a base such as triethylamine at a temperature of from room temperature to 80° C.

Furthermore, compounds of the formula (Ig) and (Ih) where R₁≈H may be obtained from compounds of formula (Ig) and (Ih) where R₁=H, using the methods described for the transformation of compounds of formula (Ia) to compounds of formula (Ib) in Scheme A. It should be clear to the skilled person that other appropriate protecting group strategies may be contemplated at R₁ and that the incorporation of R₁ (where R₁≈H) can be possible at any intervening step in the synthesis of compounds of the invention, (Ig) and (Ih).

A compound of formula (XXVI) may be prepared according to Scheme J from a compound of formula (IX). A compound of formula (XXIV) may be prepared using Heck coupling chemistry by reaction with an appropriately substituted vinyl compound (XXIII) in the presence of an appropriate catalyst/ligand system such as Herrmann-Beller catalyst/ tributylphosphine tetrafluoroborate in a solvent such as tetraethylene glycol or dimethoxyethane in the presence of a base such as pentamethylpiperidine at a temperature of from room temperature to 160° C. A compound of formula (XXV) may be prepared from compounds of formula (XXIV) following hydrolysis and reduction steps using an acid such as trifluoroacetic acid in a solvent such as DCM at −10° C. to give the intermediate aldehyde, and a reducing agent such as sodium borohydride in a solvent such as MeOH at a temperature of from 0° C. to room temperature to give a compound of formula (XXV). A compound of formula (XXVI) can be prepared from a compound of formula (XXV) using a mixture of carbon tetrabromide/triphenyl phosphine in a solvent such as DCM at a temperature of from 0° C. to 50° C.

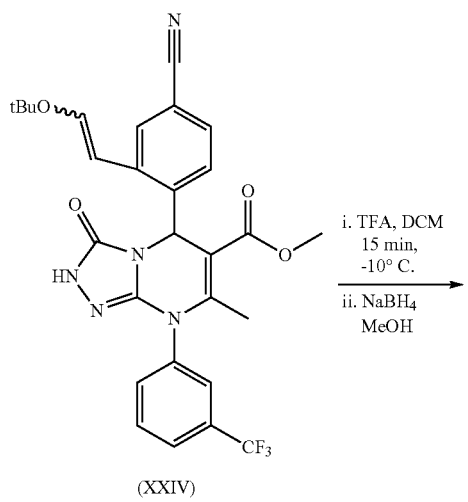

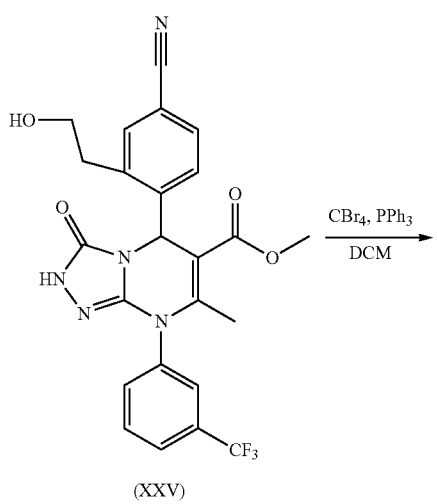

-continued

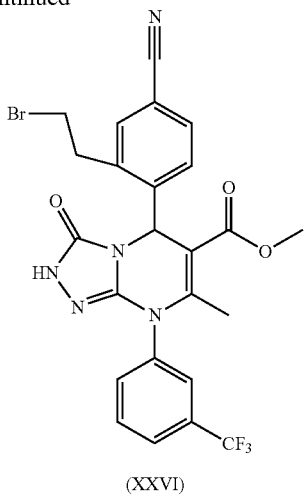

(XXVI)

Compounds of formula (Ij), (Ik) or (Im), i.e. compounds of formula (I) where $R_2$ is defined as $(C_1-C_4)$alkyleneN$^+$R$_{22}$R$_{23}$R$_{24}$, a group $(C_1-C_4)$alkyleneNR$_{18}$R$_{19}$, a group [CH$_2$]$_y$G[CH$_2$]$_j$CH$_2$—N$^+$pyridinium(R38), respectively as substituents, may be prepared according to Scheme K. Similarly, compounds of formula (Ij), (Ik) or (Im), i.e. compounds of formula (I) where $R_2$ is defined as a group alkyne-Ry or C(O)NHCH$_2$Rx may be prepared according to Scheme K. Compounds of formula (Ij), (Ik) or (Im) may also be prepared similarly from compounds of formula (XXVII).

Scheme K.

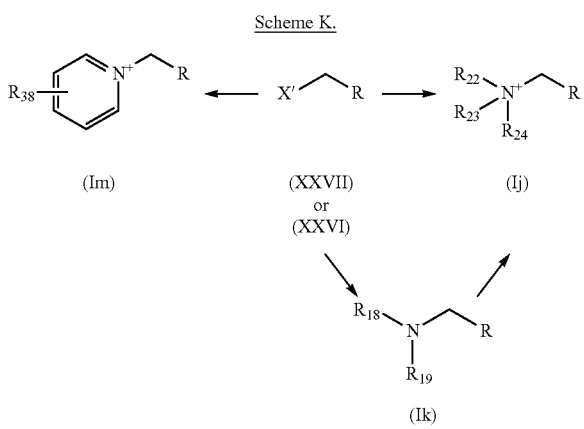

Compounds of formula (Ij) can be obtained directly by alkylation reaction of an appropriate tertiary amine R$_{22}$R$_{23}$R$_{24}$N, such as trimethylamine or dimethylpiperazine, with compounds of formula (XXVII) wherein X' is an appropriate leaving group (X'=Cl, Br, I, Tosylate etc.) and group —CH$_2$R represents the portion of a compound of formula (Ij) remaining out of its substitution by a group $(C_1-C_4)$alkyleneN$^+$R$_{22}$R$_{23}$R$_{24}$. Typical conditions could involve heating a tertiary amine in a solvent such as ethanol or THF at elevated temperatures of between 60° C. and 150° C., using microwave irradiation.

Alternatively, the transformation of compounds of formula (XXVII) to compounds of formula (Ij) may be achieved via the tertiary amine (Ik) where $R_{18}$ and $R_{19}$≈H. Tertiary amine compounds of formula (Ik) may be prepared from compounds of formula (XXVII) by reaction with a secondary amine R$_{19}$R$_{18}$NH. Typical reaction conditions include the use of a base such as cesium carbonate or potassium carbonate in a solvent such as DMF at RT. The conversion of compounds of formula (Ik), where $R_{18}$ and $R_{19}$≈H, to compounds of formula (Ij) can be obtained using methylating agents such as methyl bromide, methyl iodide or methyl benzenesulfonate. Typical reaction conditions consist of the use of a solvent such as MeCN or acetone at a temperature of between RT to 60° C. under conventional or microwave heating.

Furthermore, primary and secondary amine compounds of formula (Ik) may also be prepared from compounds of formula (XXVII) by reaction with ammonia or a suitable primary amine R$_{18}$NH$_2$, respectively to give a primary amine or secondary amine.

Compounds of formula (Im) can be obtained directly by alkylation reaction of an appropriate pyridine-containing compound such as pyridine with compounds of formula (XXVII), wherein X' is an appropriate leaving group (X'=Cl, Br, I, Tosylate etc.) and group —CH$_2$R represents the portion of a compounds of formula (Im) remaining out of its substitution by a group or a group [CH$_2$]$_y$G[CH$_2$]$_j$CH$_2$—N pyridinium (R38). Typical conditions could involve heating compounds of formula (XXVII), with pyridine in a solvent such as MeCN or THF at elevated temperatures of between 50° C. and 100° C., using microwave irradiation.

Compounds of formula (Ij), (Ik) or (Im), i.e. compounds of formula (I) which incorporate a group R$_y$ or R$_x$ (see Scheme F/H) defined as $(C_1-C_4)$alkyleneN$^+$R$_{22}$R$_{23}$R$_{24}$, a group $(C_1-C_4)$alkyleneNR$_{18}$R$_{19}$, or a group [CH$_2$]$_y$G[CH$_2$]$_j$CH$_2$—N$^+$pyridinium(R38), respectively as substituents, may be also be prepared according to Scheme K from compounds of formula (XXVI).

Other features of the invention will become apparent in the course of the following descriptions of exemplary embodiments which are given for illustration of the invention and are not intended to be limiting thereof.

EXAMPLES

Reactions were not carried out under an inert atmosphere unless specified and all solvents and commercial reagents were used as received.

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled, the organic fraction removed by evaporation, and the remaining aqueous fraction lyophilised, to give the final product. Where thin layer chromatography (TLC) has been used, it refers to silica gel TLC using plates, typically 3×6 cm silica gel on aluminium foil plates with a fluorescent indicator (254 nm), (e.g. Fluka 60778). Microwave experiments were carried out using a Biotage Initiator 60™ which uses a single-mode resonator and dynamic field tuning. Temperature from 40-250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using the Autonom 2000 feature in MDL ISIS™/Draw 2.5 SP2 software.

Preparative HPLC Conditions

HPLC System 1

C18-reverse-phase end-capped column (250×21.2 mm Gemini column with 5 μm particle size), eluting with a gradient of A: water; B: MeCN (0.1% formic acid added) with a flow rate typically 18 mL/min and gradient of 1%/min increasing in B. UV detection at 254 nm.

HPLC System 2

C18-reverse-phase end-capped column (250×21.2 mm Gemini column with 5 μm particle size), eluting with a gradient of A: water; B: methanol (0.1% formic acid added) with a flow rate typically 13 mL/min and gradient of 1%/min increasing in B. UV detection at 254 nm.

Analytical LC-MS Conditions

LC-MS Method 1

The Waters ZQ quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 μl/min split to the ESI source with in-line HP1100 PDA detector)

MS ionization method—Electrospray (positive and negative ion)

LC-MS Method 2

Waters Micromass ZMD quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow(mL/min) | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 μl split to MS with in-line UV detector)

MS ionization method—Electrospray (positive and negative ion)

LC-MS Method 3

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid. Alternatively, where specified, a C18-reverse-phase (100×2.1 mm Acquity UPLC BEH Shield 1.7 μm particle size) column was used.

Gradient:

| Gradient - Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionization method—Electrospray (positive/negative ion).

LC-MS Method 4

Waters Platform LC quadrupole mass spectrometer with a C18-reverse-phase column (30×4.6 mm Phenomenex Luna 3 μm particle size), elution with A: water+0.1% formic acid; B: MeCN+0.1% formic acid. Gradient:

| Gradient - Time | flow (mL/min) | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (Split—200 μl/min split to the ESI source with in-line HP1100 DAD detection)

MS ionization method—Electrospray (positive and negative ion).

LC-MS Method 5

Waters VG Platform II quadrupole spectrometer with a C18-reverse-phase column (30×4.6 mm Luna 3 μm particle size), elution with A: water+0.1% formic acid; B: MeCN+ 0.1% formic acid.

Gradient:

| Gradient - Time | flow | % A | % B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (Split—200 μl/min split to the ESI source with in-line HP1050 DAD detection)

MS ionization method—Electrospray (positive and negative ion)

MDAP System:

Instrumentation: Agilent 1260 infinity purifications system. Agilent 6100 series single Quadrupole LC/MS Column: XSELECT CSH Prep C18 5 μm OBD, 30×150 mm, RT Mobile Phase A: 0.1% aqueous formic acid Mobile Phase B: 0.1% formic acid in acetonitrile Flow: 60 ml/min Gradient Program: 10%-95%, 22 min, centred around a specific focused gradient Sample Injection of a 20-60 mg/ml solution in DMSO (+optional formic acid and water).

Abbreviations used in the experimental section:

9-BBN 9-Borabicyclo[3.3.1]nonane dba Dibenzylideneacetone

DCE Dichloroethane

DCM Dichloromethane

DIPEA Di-isopropylethylamine

DMF N,N-dimethylformamide
DMSO Dimethylsulphoxide
Dppf 1,1'-Bis(diphenylphosphino)ferrocene
Et$_2$O Diethyl ether
EtOAc Ethyl acetate
HPLC High performance liquid chromatography
IMS Industrial methylated spirits
LC-MS Liquid chromatography-mass spectrometry
MeCN Acetonitrile
MDAP Mass Directed Automatic Purification
NBS N-Bromosuccinimide
NMO N-Methylmorpholine-N-Oxide
Rt Retention time
RT Room temperature
THF Tetrahydrofuran In the procedures that follow, some of the starting materials are identified through an "Intermediate" or "Example" number. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Example 1

5-[4-Cyano-2-(4-hydroxy-but-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

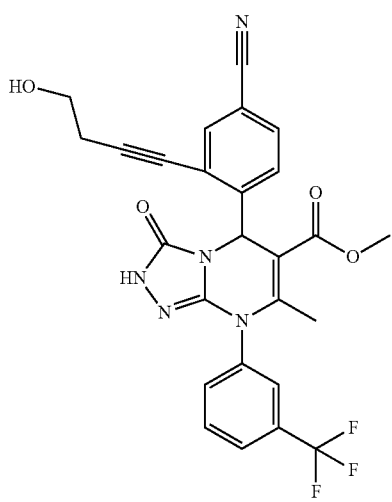 [SMILES: COC(=O)C1=C(C)N(c2cccc(C(F)(F)F)c2)c2n[nH]c(=O)n2C1c1ccc(C#N)cc1C#CCCO]

Intermediate 1

4-(2-Bromo-4-cyanophenyl)-6-methyl-2-thioxo-1-(3-trifluoromethylphenyl)-1,2,3,4-tetrahydro-pyrimidine-5-carboxylic acid methyl ester

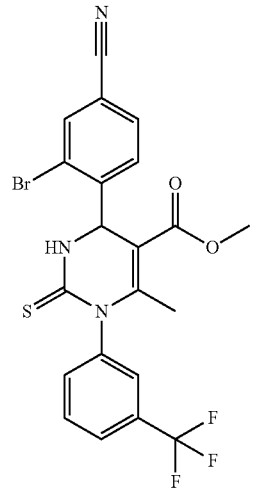 [SMILES: COC(=O)C1=C(C)N(c2cccc(C(F)(F)F)c2)C(=S)NC1c1ccc(C#N)cc1Br]

3-Trifluoromethylphenylthiourea (12.8 g, 87 mmol), 2-bromo-4-cyanobenzaldehyde (18.3 g, 87 mmol), and methyl acetoacetate (10.4 mL, 96 mmol) were dissolved in THF (300 mL) under an atmosphere of N$_2$ and then trimethylsilylphosphate (18 g) in THF (50 mL) was added, and the mixture heated at 75° C. After 17 hours the reaction mixture was allowed to cool, poured onto 0.5 M HCl (600 mL) and stirred for 30 minutes. The mixture was extracted into EtOAc. The organic phase was washed with water, then brine and dried (Na$_2$SO$_4$) before being concentrated in vacuo. The resulting solid was triturated with Et$_2$O (50 mL), filtered and the solid collected to yield the title compound as a white solid (22.2 g).

LC-MS (Method 2): Rt=4.03 min, m/z=432 [M(79Br)+H]$^+$

Intermediate 2

4-(2-Bromo-4-cyanophenyl)-2-hydrazino-6-methyl-1-(3-trifluoromethylphenyl)-1,4-dihydro-pyrimidine-5-carboxylic acid methyl ester

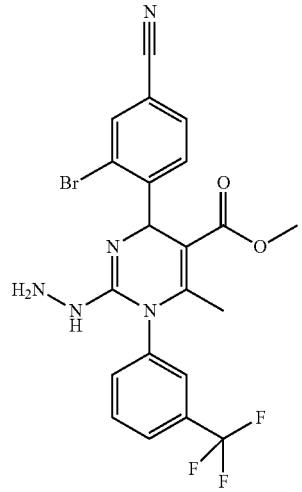 [SMILES: COC(=O)C1=C(C)N(c2cccc(C(F)(F)F)c2)C(NN)=NC1c1ccc(C#N)cc1Br]

Intermediate 1 (4.6 g, 9 mmol) was dissolved in IMS (350 mL), urea hydrogen peroxide (3.4 g, 36.2 mmol) was added, and the mixture stirred for 2 hours at RT before addition of hydrazine hydrate (4.1 mL, 54.4 mmol). The mixture was stirred for a further 2 hours at RT, filtered, the filtrate collected and then the solvent reduced to a low volume in vacuo. The resultant residue was partitioned between EtOAc and brine. The organic layer was separated, washed with brine, dried (Na$_2$SO$_4$) and evaporated in vacuo. The resulting residue was used directly in the next step.

LC-MS (Method 2): Rt=2.49 min, m/z=508 [M($^{79}$Br)+H]$^+$

Intermediate 3

4-(2-Bromo-4-cyanophenyl)-2-(M-ethoxycarbonyl-hydrazino)-6-methyl-1-(3-trifluoro methylphenyl)-1,4-dihydro-pyrimidine-5-carboxylic acid methyl ester

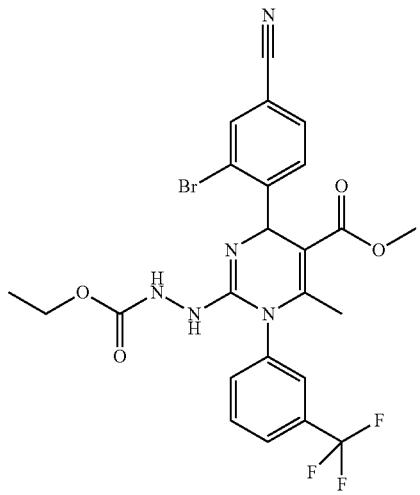 [SMILES: CCOC(=O)NNC1=NC(c2ccc(C#N)cc2Br)C(C(=O)OC)=C(C)N1c1cccc(C(F)(F)F)c1]

Intermediate 2 (approximately 9 mmol) was dissolved in DCM (40 mL) under an atmosphere of N$_2$ and cooled to −78° C. before addition of triethylamine (1.7 mL, 12 mmol) and ethyl chloroformate (765 µL, 8 mmol). The reaction mixture was stirred at −78° C. and allowed to warm slowly to RT over 16 hours and then partitioned between EtOAc and water. The organic layer was separated, washed with brine, dried (Na$_2$SO$_4$) and evaporated in vacuo. The resulting residue was purified by silica gel chromatography eluting with a gradient of 0-50% EtOAc in cyclohexane to give the title compound as a yellow solid (2 g over 2 steps).

LC-MS (Method 2): Rt=3.55 min, m/z=580 [M($^{79}$Br)+H]$^+$

Intermediate 4

5-(2-Bromo-4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester

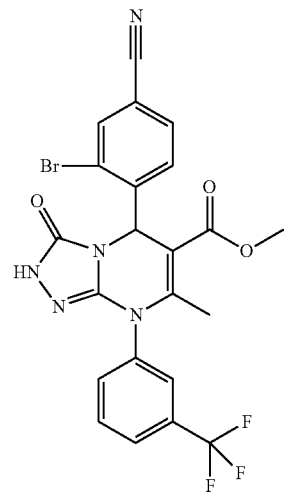 [SMILES: COC(=O)C1=C(C)N(c2cccc(C(F)(F)F)c2)c2n[nH]c(=O)n2C1c1ccc(C#N)cc1Br]

Route A

Intermediate 3 (2 g, 3.5 mmol) was dissolved in IMS (20 mL) and heated at 160° C. for 1 hour using microwave irradiation. The solvent was removed in vacuo and the resulting residue triturated with Et$_2$O, filtered and the solid collected to yield the title compound as a white solid (1.5 g).

LC-MS (Method 3): Rt=4.65 min, m/z=534 [M($^{79}$Br)+H]$^+$ $^1$H NMR (400 MHz, DMSO) δ 11.20 (1H, s), 8.18 (1H, d, J=1.6 Hz), 8.09 (1H, br s), 7.93-7.75 (5H, m), 6.23 (1H, d, J=1.2 Hz), 3.49 (3H, s), 2.13 (3H, s).

Route B

To Intermediate 1 (75 g, 147 mmol) dissolved in dry DCM (1350 mL) and 2,6-lutidine (51.3 mL) at 0° C. under nitrogen was added portion-wise triphosgene (13.82 g) with stirring. After 5 minutes the reaction was warmed to 20° C. and stirred for 25 minutes. The reaction mixture was cooled to 10° C. and added via a cannula to a stirred solution of anhydrous hydrazine (0.419 moles) in THF (400 mL) and MeCN (380 mL) cooled in an ice bath. After a further 5 minutes, the reaction was warmed to 20° C. and stirred at RT for 2¼ hours. Water (800 mL) degassed with nitrogen was added to the reaction and the organic layer washed with further water (800 mL) and then brine (500 mL). The organic layer was dried (Na$_2$SO$_4$) and evaporated in vacuo and the residue was re-dissolved in toluene (300 mL) and again evaporated in vacuo. The residue was dissolved in toluene (500 mL) a final time and concentrated to a weight ~200 g. The resultant solution was diluted with Et$_2$O (500 mL) and left to crystallise. The title compound was collected by filtration to give yellow solid (32.1 g). The mother liquors were concentrated in vacuo and the resultant residue was dissolved in DCM and left to crystallise. The solid was collected to give further title product as a yellow solid (2.56 g).

LC-MS (710016978): Rt=3.39 min, m/z=533.9 [M($^{79}$Br)+H]$^+$

Intermediate 4a/4b (R) and (S) 5-(2-Bromo-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

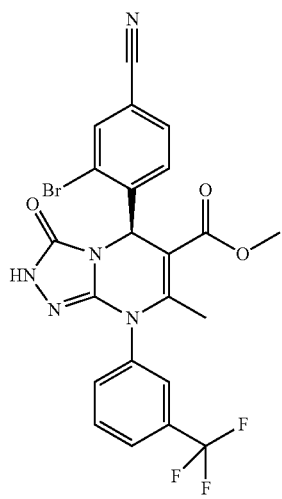

(4a)

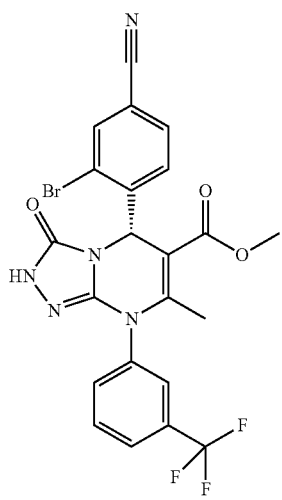

(4b)

The enantiomers of Intermediate 4 (155 mg, 0.290 mmol) were separated by preparative HPLC chromatography on a chiral phase [Daicel Chiralpak IC column (5 µm, 250 mm×10 mm, 1% MeOH/DCM eluent, 5 mL/min flow rate, 220 nm detection)] to give 69 mg of the (R) enantiomer (first eluting and assigned as 4a) and 71 mg of the (S) enantiomer (second eluting and assigned as 4b).

5-[4-Cyano-2-(4-hydroxy-but-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 1)

Intermediate 4 (150 mg, 0.28 mmol), 3-butyn-1-ol (42 mL, 0.57 mmol), bis(triphenylphosphine) palladium(II) dichloride (15 mg, 0.021 mmol), and copper (1) iodide (6 mg, 0.024 mmol) were dissolved in DMF (1.5 mL) and triethylamine (1.5 mL) and then purged with $N_2$ for 5 minutes. The reaction mixture was then heated at 120° C. for 1 hour using microwave irradiation. The reaction mixture was then filtered through a plug of silica and the resulting residue was purified by reverse phase HPLC (Method 1) using a gradient of 10-60% (+0.1% formic acid) MeCN in water to yield the title compound as an off-white solid (32 mg).

LC-MS (Method 3): Rt=4.30 min, m/z=524 [M+H]$^+$ $^1$H NMR (400 MHz, CDCl$_3$) δ 8.14 (1H, s), 7.79 (1H, d, J=8 Hz), 7.72-7.67 (2H, m), 7.60 (1H, s), 7.54 (2H, dd, J=8, 2 Hz), 7.37 (1H, d, J=8 Hz), 6.64 (1H, s), 3.87-3.77 (2H, m), 3.58 (3H, s), 2.76-2.63 (2H, m), 2.58 (1H, s), 2.24 (3H, s).

Example 2

5-[4-Cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester formate salt

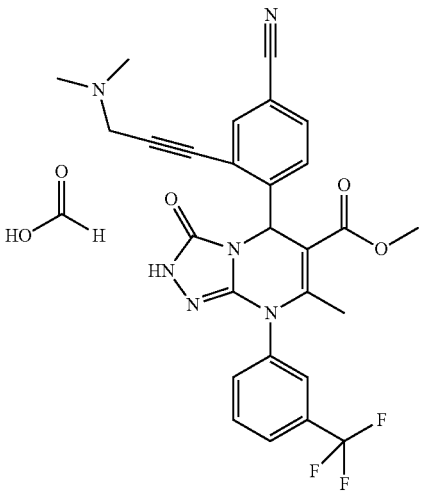

Intermediate 4 (400 mg, 0.75 mmol), 1-dimethylamino-2-propyne (160 µL, 1.5 mmol), bis(triphenylphosphine)palladium(II) dichloride (79 mg, 0.11 mmol) and copper (1) iodide (43 mg, 0.23 mmol) were dissolved in DMF (2.5 mL) and triethylamine (2.5 mL) and purged with $N_2$ for 5 minutes. The reaction was then heated at 125° C. for 50 mins using microwave irradiation. The reaction mixture was filtered through a plug of celite and then diluted with EtOAc. The resultant solution was washed with brine, dried (Na$_2$SO$_4$) and evaporated in vacuo. A portion of the resulting residue (25 mg) was purified by reverse phase HPLC (Method 1) using a gradient of 10-40% (+0.1% formic acid) and gave the title compound as an off-white solid (11 mg).

LC-MS (Method 3): Rt=3.38 min, m/z=537 [M+H]$^+$ $^1$H NMR (400 MHz, CDCl$_3$) δ 9.30 (1H, br s), 8.28 (1H, s), 7.82-7.71 (3H, m), 7.64-7.58 (3H, m), 7.42 (1H, d, J=8 Hz), 6.50 (1H, s), 3.84 (1H, d, J=17 Hz), 3.76 (1H, d, J=17 Hz), 3.60 (3H, s), 2.60 (6H, s), 2.26 (3H, s).

Example 3

5-[4-Cyano-2-(3-dimethylamino-prop-1-ynyl)-phenyl]-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

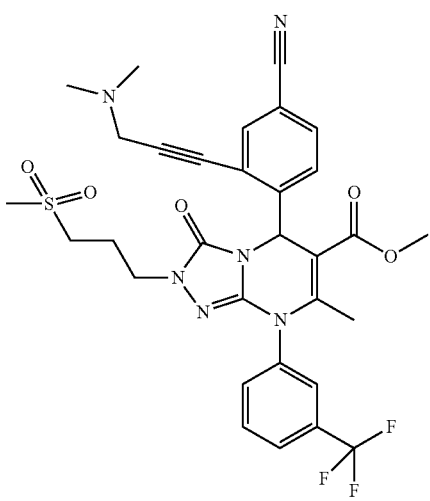

Intermediate 5

1-Bromo-3-methanesulfonyl-propane

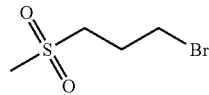

3-(Methylsulfonyl)-1-propanol (276 mg, 2 mmol) was dissolved in DCM (10 mL) and then CBr$_4$ (730 mg, 2.2 mmol) was added followed by PPh$_3$ (580 mg, 2.2 mmol) portionwise under an atmosphere of N$_2$. The resulting solution was stirred at RT for 17 hours. The mixture was partitioned between DCM and water. The organic layer was separated, washed with brine, dried (Na$_2$SO$_4$) and evaporated in vacuo. The resulting residue was purified by silica gel chromatography eluting with 50% EtOAc in cyclohexane to yield the title compound as a colorless oil (297 mg).

$^1$H NMR (400 MHz, DMSO) δ 3.63 (2H, t, J=7 Hz), 3.25-3.20 (2H, m), 3.01 (3H, s), 2.27-2.19 (2H, m).

5-[4-Cyano-2-(3-dimethylamino-prop-1-ynyl)-phenyl]-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester Example 2 (34.5 mg, 0.06 mmol) was dissolved in DMF (1 mL) and then cesium carbonate (25 mg, 0.08 mmol) and intermediate 4 (13 mg, 0.06 mmol) were added. The mixture was stirred at RT for 16 hours. The mixture was partitioned between EtOAc and water. The organic layer was separated, and the aqueous layer extracted with EtOAc. The combined organic layers were washed with brine, dried (Na$_2$SO$_4$) and evaporated in vacuo. The resulting residue was purified by silica gel chromatography eluting from 0-10% (2 M NH$_3$ in MeOH) in DCM to yield the title compound as a white solid (4 mg).

LC-MS (Method 3): Rt=3.45 min, m/z=657 [M+H]$^+$ $^1$H NMR (400 MHz, CDCl$_3$) δ 7.82-7.69 (3H, m), 7.63-7.58 (3H, m), 7.43 (1H, d, J=8 Hz), 6.50 (1H, s), 3.74-3.59 (2H, m), 3.61 (3H, s), 3.55 (2H, s), 2.95-2.90 (2H, m), 2.80 (3H, s), 2.40 (6H, s), 2.24 (3H, s), 2.12-2.04 (2H, m).

Example 4

(3-{5-Cyano-2-[2-(3-methanesulfonyl-propyl)-6-methoxycarbonyl-7-methyl-3-oxo-8-m-tolyl-2,3,5,8-tetrahydro-[1,2,4]triazolo[4,3-a]pyrimidin-5-yl]-phenyl}-prop-2-ynyl)-trimethyl-ammonium formate

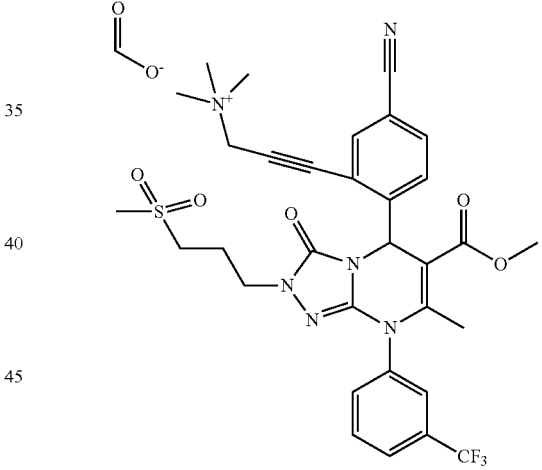

Example 3 (16 mg, 0.02 mmol) was dissolved in a 30% methyl bromide in MeCN solution (1 mL) and then K$_2$CO$_3$ (10 mg) was added. The mixture was stirred at RT for 24 hours. The reaction mixture was filtered and then evaporated in vacuo. The resulting residue was purified by reverse phase HPLC (Method 1) eluting from 10-40% (+0.1% formic acid) and gave the title compound as a white solid (11 mg).

LC-MS (Method 3): Rt=3.45 min, m/z=671 [M+H]$^+$ $^1$H NMR (400 MHz, DMSO) δ 8.46 (2H, s), 8.16-8.15 (1H, m), 7.96-7.92 (2H, m), 7.89-7.82 (2H, m), 6.34 (1H, s), 4.78 (1H, d, J=16 Hz), 4.72 (1H, d, J=16 Hz), 3.64-3.56 (2H, m), 3.53 (3H, s), 3.27 (9H, s), 3.05-2.92 (2H, m), 2.88 (3H, s), 2.17 (3H, s), 1.86-1.77 (2H, m).

Example 5

5-[4-Cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

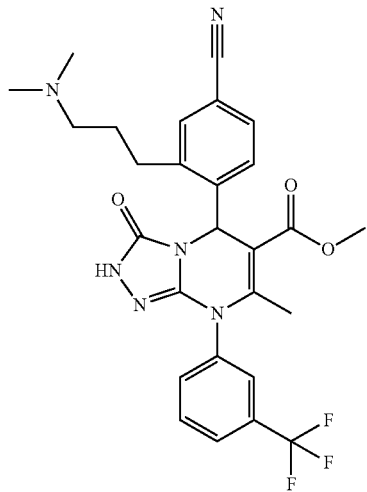

Example 2 (35 mg, 0.06 mmol) was dissolved in IMS (0.5 mL) and then added to a suspension of 10% palladium on carbon (approx. 30 mg) in IMS (0.5 mL). The mixture was stirred under a $H_2$ atmosphere (balloon) for 2 hours and then filtered through Celite© and the filtrate evaporated in vacuo. The resulting residue was purified by silica gel chromatography eluting from 0-10% (2 M $NH_3$ in MeOH) in DCM to give the title compound as a white solid (6 mg).

LC-MS (Method 3): Rt=3.43 min, m/z=541 [M+H]$^+$ $^1$H NMR (400 MHz, CDCl$_3$) δ 7.80 (1H, d, J=9 Hz), 7.72 (1H, t, J=8 Hz), 7.64 (1H, s), 7.59 (1H, d, J=8 Hz), 7.54 (1H, s), 7.50 (1H, dd, J=8, 1 Hz), 7.37 (1H, d, J=8 Hz), 6.28 (1H, s), 3.59 (3H, s), 3.28-3.20 (1H, m), 3.07-2.99 (1H, m), 2.48 (2H, t, J=7 Hz), 2.28 (6H, s), 2.24 (3H, s), 2.07-1.99 (1H, m), 1.94-1.85 (1H, m).

Example 6

5-(4-Cyano-2-dimethylaminomethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

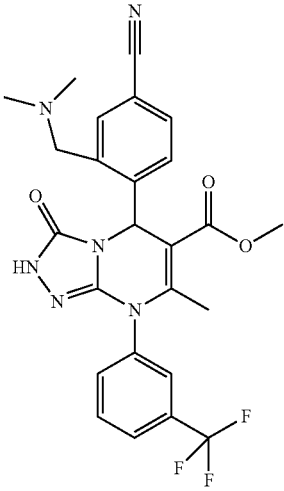

Intermediate 6

5-(4-Cyano-2-vinyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

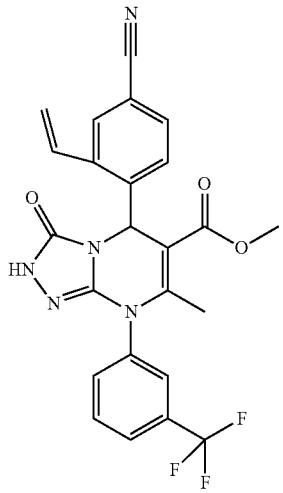 [SMILES: C=Cc1cc(C#N)ccc1C1C(C(=O)OC)=C(C)N(c2cccc(C(F)(F)F)c2)c2n[nH]c(=O)n21]

Intermediate 4 (1.42 g, 2.66 mmol), tributyl vinyl stannane and palladium-tetrakis(triphenylphosphine) were dissolved in dioxane (18 mL) and a few drops of DMF and the resulting solution was purged with $N_2$ for 5 minutes. The reaction mixture was then heated at 150° C. for 1 hour using microwave irradiation. The reaction mixture was purified by silica gel chromatography eluting with a gradient of 0-70% EtOAc in cyclohexane followed by trituration with Et$_2$O to yield the title compound as an off-white solid (1.02 g).

LC-MS (Method 2): Rt=3.52 min, m/z=482 [M+H]$^+$

Intermediate 7

5-(4-Cyano-2-formyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

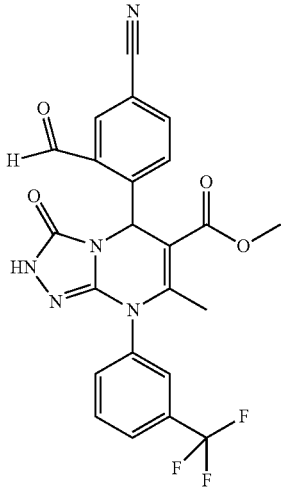 [SMILES: COC(=O)C1=C(C)N(c2cccc(C(F)(F)F)c2)c2n[nH]c(=O)n2C1c1ccc(C#N)cc1C=O]

Intermediate 6 (0.8 g, 1.66 mmol) was suspended in acetone (4.5 mL) and water (0.5 mL). Potassium osmate dihydrate (31 mg, 0.08 mmol) was added, followed by NMO (0.39 g, 3.32 mmol) and the reaction mixture stirred vigorously at RT for 18 hours. Na$_2$S$_2$O$_5$ (4 g, 21.06 mmol) was then added and the reaction diluted with DCM and stirred for a further 20 minutes. The resultant mixture was filtered through celite and then evaporated in vacuo. The resultant residue was taken up in THF (8 mL) and water (8 mL) and then cooled to 0° C. before sodium periodate (0.71 g, 3.32 mmol) was added. The reaction mixture was allowed to warm to RT and then stirred for 3 hours before being diluted with saturated aqueous NaHCO$_3$ and then extracted with EtOAc. The combined organic layers were washed with saturated aqueous NaHCO$_3$ then brine, dried (Na$_2$SO$_4$) and evaporated in vacuo. The resulting residue was purified by silica gel chromatography eluting with a gradient of 50-70% EtOAc in cyclohexane to yield the title compound as a pink solid (0.56 g).

LC-MS (Method 1): Rt=2.98 min, m/z=484 [M+H]$^+$

Intermediate 8

5-(4-Cyano-2-hydroxymethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

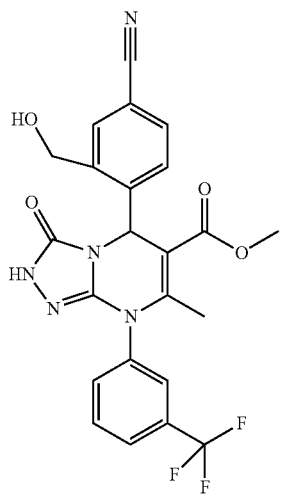 [SMILES: COC(=O)C1=C(C)N(c2cccc(C(F)(F)F)c2)c2n[nH]c(=O)n2C1c1ccc(C#N)cc1CO]

Intermediate 7 (273 mg, 0.57 mmol) was dissolved in MeOH (5 mL) and sodium borohydride (26 mg, 0.68 mmol) was added and the reaction stirred at RT for 2 hours. The mixture was evaporated in vacuo and the residue partitioned between EtOAc and water and the phases separated. The organic layer was washed with brine, dried (Na$_2$SO$_4$) and evaporated in vacuo. The resulting residue was triturated with Et$_2$O, filtered and the solid collected to yield the title compound as an off-white solid (184 mg).

LC-MS (Method 2): Rt=3.24 min, m/z=486 [M+H]+

Intermediate 9

5-(2-Bromomethyl-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

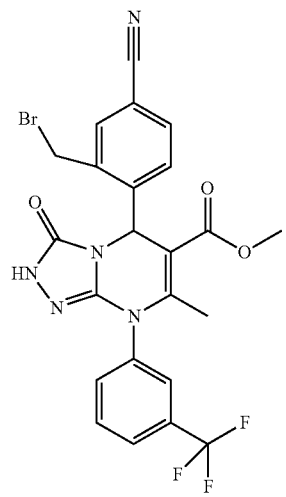 [SMILES: COC(=O)C1=C(C)N(c2cccc(C(F)(F)F)c2)c2n[nH]c(=O)n2C1c1ccc(C#N)cc1CBr]

Intermediate 8 (approximately 0.1 mmol) was dissolved in DCM (1 mL) and the solution cooled to 0° C. Carbon tetrabromide (40 mg, 0.12 mmol) was added, followed by triphenylphosphine (29 mg, 0.11 mmol) and the reaction stirred at RT. After 5 hours, further portions of carbon tetrabromide (53 mg, 0.16 mmol) and triphenylphosphine (42 mg, 0.16 mmol) were added and stirring continued at RT for 16 hours. The reaction mixture was diluted with DCM and washed with water followed by brine, dried (Na$_2$SO$_4$) and evaporated in vacuo. The resulting residue was purified by silica gel chromatography eluting with a gradient of 50-80% EtOAc in cyclohexane to give the title compound as a white solid (19 mg).

LC-MS (Method 1): Rt=3.12 min, m/z=548 [M+H]$^+$ 5-(4-Cyano-2-dimethylaminomethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 6)

Intermediate 9 (23 mg, 0.04 mmol) was dissolved in THF (0.5 mL), 2 M dimethylamine in MeOH (0.5 mL) was added and the reaction stirred at RT. After 2 hours the reaction mixture was evaporated to dryness and the resulting residue was purified by silica gel chromatography eluting with a gradient of 0-5% (2 M NH$_3$ in MeOH) in DCM to yield the title compound as a white solid (13 mg).

LC-MS (Method 3): Rt=3.38 min, m/z=513 [M+H]$^+$ $^1$H NMR (400 MHz, CDCl$_3$) δ 8.07 (1H, s), 7.82-7.81 (2H, m), 7.74 (1H, t, J=8 Hz), 7.65 (1H, s), 7.60 (1H, d, J=7 Hz), 7.55-7.52 (1H, m), 7.38 (1H, d, J=8 Hz), 6.31 (1H, s), 4.16 (1H, d, J=16 Hz), 3.86 (1H, d, J=16 Hz), 3.61 (3H, s), 2.38 (6H, s), 2.26 (3H, s).

Example 7

{5-Cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium bromide

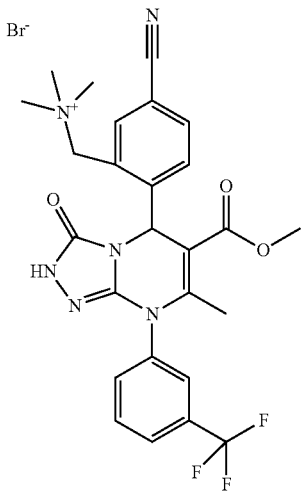

Intermediate 9 (17 mg, 0.03 mmol) was dissolved in THF (2 mL) and 31% trimethylamine in EtOH (2 mL) and the mixture stirred at RT for 72 hours. The solvent was removed in vacuo and the resulting residue was purified by reverse phase HPLC using a gradient of 10-90% MeCN in water to give the title compound as a white solid (6 mg).

LC-MS (Method 3): Rt=3.28 min, m/z=527 [M]$^+$ $^1$H NMR (400 MHz, DMSO) δ 11.34 (1H, s), 8.11 (2H, s), 8.03 (1H, dd, J=2 and 8 Hz), 7.95-7.79 (4H, m), 6.48 (1H, s), 5.13 (1H, d, J=14 Hz), 4.98 (1H, d, J=14 Hz), 3.52 (3H, s), 3.26 (9H, s), 2.07 (3H, s).

Example 8

(2-{5-Cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzoylamino}-ethyl)-trimethyl-ammonium chloride

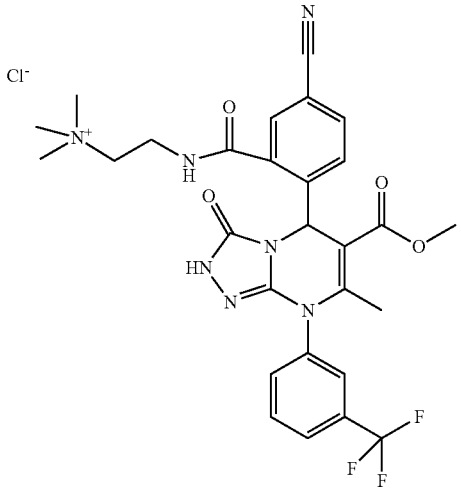

Intermediate 10

5-(2-Carboxy-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

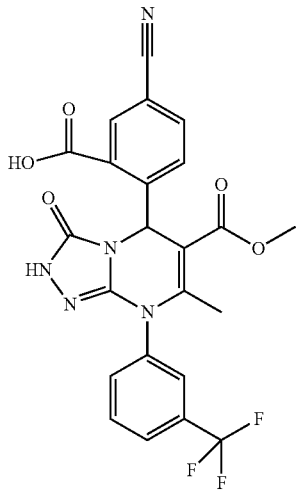 [SMILES: COC(=O)C1=C(C)N(c2cccc(C(F)(F)F)c2)c2n[nH]c(=O)n2C1c1ccc(C#N)cc1C(=O)O]

Intermediate 7 (50 mg, 0.1 mmol) was dissolved in tert-butanol (700 μL) and water (170 μL), then sodium dihydrogenphosphate (14 mg, 0.1 mmol) and 2-methyl-2-butene (2 M in THF, 220 μL, 0.44 mmol) were added, followed by sodium chlorite (40 mg, 0.35 mmol) and the mixture was stirred at RT for 4 hours. The mixture was acidified to pH 1 with aqueous 1 M HCl and then extracted with EtOAc and the combined organic layers were washed with brine, dried (Na$_2$SO$_4$) and evaporated in vacuo to yield the title compound as a cream foam.

LC-MS (Method 1): Rt=2.77 min, m/z=500 [M+H]$^+$ (2-{5-Cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzoylamino}-ethyl)-trimethyl-ammonium chloride
(Example 8)

Intermediate 10 (0.1 mmol) was dissolved in DMF (2 mL) and diisopropylethylamine (68 μL, 0.4 mmol) was added followed by HATU (57 mg, 0.15 mmol). (2-Aminoethyl)trimethylammonium chloride hydrochloride (22 mg, 0.12 mmol) was added and the mixture stirred at RT for 16 hours. The mixture was partitioned between EtOAc and water. The organic layer was separated, and the aqueous layer extracted with EtOAc and the combined organic layers were washed with brine, dried (Na$_2$SO$_4$) and evaporated in vacuo. The resulting residue was purified by reverse phase HPLC using a gradient of 10-90% MeCN in water (+0.1% formic acid) to give the formate of the title compound as a white solid. Following elution through Amberlite IRA458 chloride resin, the title compound was obtained as a white solid (14 mg).

LC-MS (Method 3): Rt=3.28 min, m/z=584 [M]$^+$ $^1$H NMR (400 MHz, DMSO) δ 11.63 (1H, s), 9.48 (1H, s), 7.98-7.92 (3H, m), 7.88-7.80 (4H, m), 6.40 (1H, m), 3.87-3.71 (2H, m), 3.57 (2H, t, J=7 Hz), 3.41 (3H, s), 3.17 (9H, s), 2.16 (3H, s).

Example 9

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium formate

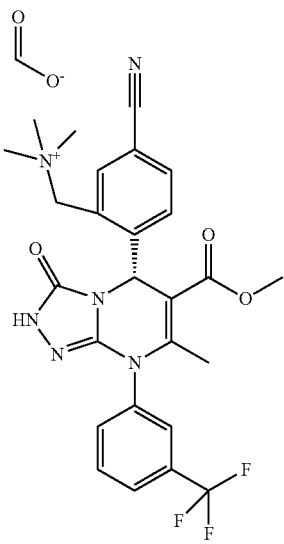

The title compound was prepared from Intermediate 4b (2.05 g, 3.81 mmol) using an analogous method to Example 7. Following MDAP purification the title compound was obtained as a white solid (107 mg).

LC-MS (Method 3): Rt=3.28 min, m/z=527 [M]+

$^1$H NMR (400 MHz, DMSO) δ 11.59 (1H, s), 8.42 (1.6H, s, formate) 8.11 (2H, m), 8.04 (1H, dd, J=1.7 and 8.3 Hz), 7.95-7.79 (4H, m), 6.49 (1H, s), 5.13 (1H, d, J=14 Hz), 4.98 (1H, d, J=14 Hz), 3.52 (3H, s), 3.26 (9H, s), 2.07 (3H, s).

Example 10

(R)-5-[4-Cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

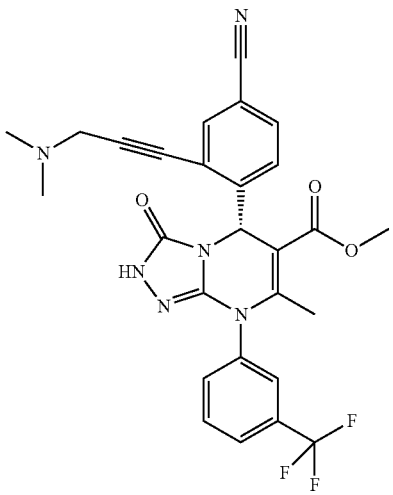

Intermediate 4b (500 mg, 0.94 mmol), 1-dimethylamino-2-propyne (305 μl, 3.76 mmol), bis(triphenylphosphine)palladium(II) dichloride (65 mg, 0.093 mmol) and copper (1) iodide (43 mg, 0.096 mmol) were dissolved in dioxane (4 mL) and triethylamine (0.48 mL) and purged with Argon for 5 minutes. The reaction was then heated at 120° C. for 30 minute using microwave irradiation. The reaction mixture was diluted with ethyl acetate and washed with water and the organic layer was dried (Na$_2$SO$_4$) and concentrated in vacuo. The resulting residue was purified by chromatography eluting from 0-5% (2 M NH$_3$ in MeOH) in DCM to yield the title compound as a brown gum (159 mg).

LC-MS (Method 1): Rt=2.48 min, m/z=537 [M+H]+

$^1$H NMR (400 MHz, DMSO) δ 8.75 (1H, br s), 7.80 (1H, d, J=7.8 Hz), 7.76 (1H, d, J=1.6 Hx), 7.72 (1H, t, J=7.8 Hz), 7.64 (1H, bs), 7.62-7.54 (2H, m), 7.42 (1 h, d, J=8.1 Hz), 6.48 (1H, m), 3.52 (2H, m), 3.60 (3H, s), 2.38 (6H, s), 2.24 (3H, s).

Example 11

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-prop-2-ynyl)-trimethyl-ammonium iodide

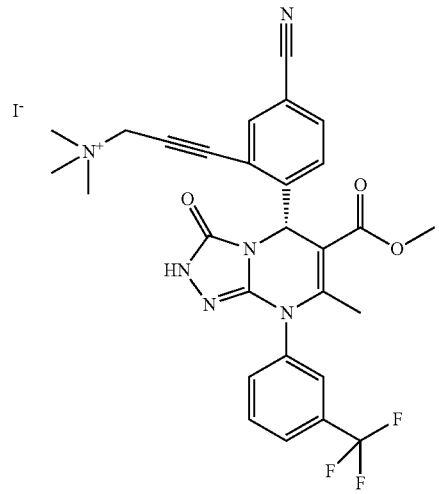

Example 10 (41 mg, 0.076 mmol) in MeCN (1 mL) was treated with iodomethane (24 μL, 0.385 mmol). After 20 minutes, the reaction was concentrated in vacuo and the residue sonicated with diethyl ether and the solid residue collected by filtration to give the title compound as a pale brown solid (36 mg).

LC-MS (Method 3): Rt=3.47 min, m/z=555.4 [M]+

$^1$H NMR (400 MHz, DMSO) δ 11.24 (1H, s), 8.12 (1H, s), 7.95-7.89 (2H, m), 7.85-7.79 (2H, m), 7.71 (1H, dd, J=1.5, 8.1 Hz), 7.66 (1H, bd, J=8.1 Hz), 6.17 (1H, s), 3.52 (3H, s), 3.48 (2H, t, J=8.5 Hz), 3.27 (1H, m) 3.13 (9H, s),) 2.97 (1H, m) 2.40 (1H, m), 2.20 (1H, m) and 2.15 (3H, s).

Example 12

(R)-5-[4-Cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

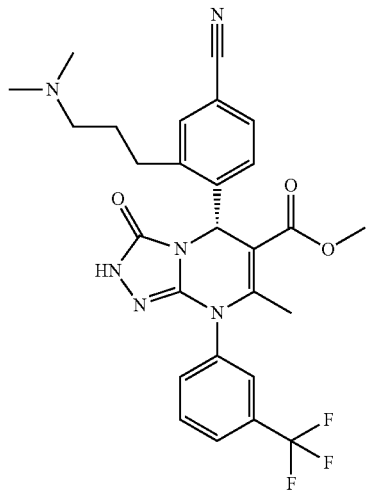

Route A

The title compound was prepared from Example 10 (120 mg, 0.223 mmol) using an analogous method to Example 5 except that the reaction required warming to 50° C. to progress satisfactorily. The resulting residue was purified by chromatography eluting from 3-8% (2 M NH$_3$ in MeOH) in DCM to yield the title compound as a brown gum (45 mg).

LC-MS (Method 3): Rt=2.55 min, m/z=541 [M+H]$^+$ $^1$H NMR (400 MHz, CDCl$_3$) δ 7.80 (1H, d, J=9 Hz), 7.72 (1H, t, J=8 Hz), 7.64 (1H, s), 7.59 (1H, d, J=8 Hz), 7.54 (1H, s), 7.50 (1H, dd, J=8, 1 Hz), 7.37 (1H, d, J=8 Hz), 6.28 (1H, s), 3.59 (3H, s), 3.28-3.20 (1H, m), 3.07-2.99 (1H, m), 2.48 (2H, t, J=7 Hz), 2.28 (6H, s), 2.24 (3H, s), 2.07-1.99 (1H, m), 1.94-1.85 (1H, m).

Route B to Example 12

Intermediate 11

(R)-5-[4-Cyano-2-(3-oxo-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

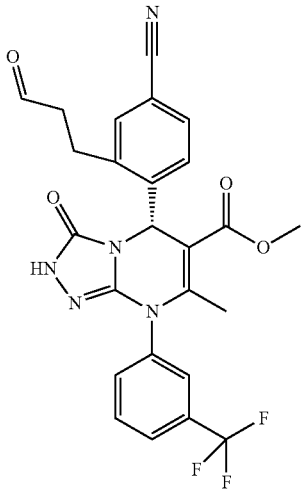 [SMILES: COC(=O)C1=C(C)N(c2cccc(C(F)(F)F)c2)c2n[nH]c(=O)n2[C@@H]1c1ccc(C#N)cc1CCC=O]

A suspension of tri-tert-butylphosphonium tetrafluoroborate (163 mg, 0.56 mmol) and tris(dibenzylideneacetone)dipalladium(0) in dry dioxane (20 mL) was degassed with argon for 10 minutes. To this was added a solution of Intermediate 4b (5.0 g, 9.36 mmol) in dry dioxane (30 mL), followed by allyl alcohol (2.55 mL, 37.43 mmol) and N,N-dicyclohexylmethylamine (4.01 mL, 18.72 mmol). The resulting mixture was stirred at 60° C. for 30 mins then cooled, filtered through Celite and concentrated in vacuo to yield the title compound as a dark yellow foam which was used without further purification (287 mg).

LC-MS (Method 4): Rt=3.32/3.49 min, m/z=512 [M+H]$^+$ (R)-5-[4-Cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Example 12)

To a solution of crude intermediate 11 (4.79 g, 9.36 mmol) in MeOH (80 mL) at 5° C. was added dimethylamine solution (2 M in methanol, 37.44 mL, 74.88 mmol) followed by sodium cyanoborohydride (647 mg, 10.30 mmol), zinc chloride (647 mg, 4.74 mmol) and 1 M HCl (56 mL, 56.0 mmol). The mixture was stirred for 30 minute and allowed to warm to RT. The resultant mixture was then partitioned between DCM and water and the aqueous layer extracted with DCM (×2) and the combined organic layers dried (Na$_2$SO$_4$), and concentrated in vacuo. The resulting residue was purified by chromatography using an Isolute® SPE Si NH$_2$ cartridge eluting with a gradient from 2-9% (2 M NH$_3$ in MeOH) in DCM. The crude product was further purified by NH$_2$ cartridge, eluting with 0-10% MeOH in EtOAc to afford the title compound as a cream foam (3.9 g)

LC-MS (Method 4): Rt=2.50 min, m/z=541 [M+H]$^+$

Example 13

3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium iodide

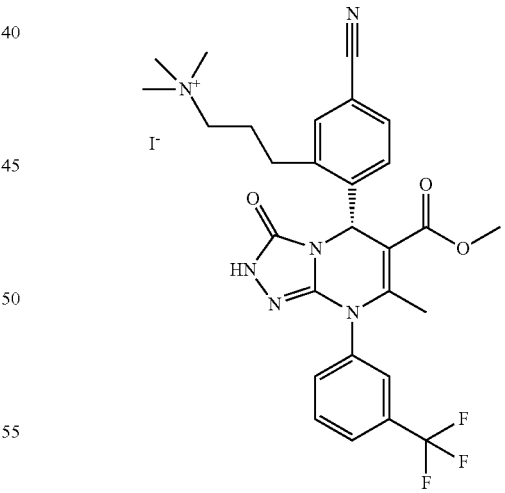

The title compound was prepared from Example 12 (41 mg, 0.076 mmol) using an analogous method to Example 11 to give the title compound as a pale brown solid (38 mg).

LC-MS (Method 3): Rt=3.47 min, m/z=555.4 [M]$^+$ $^1$H NMR (400 MHz, DMSO) δ 11.24 (1H, s), 8.12 (1H, s), 7.95-7.89 (2H, m), 7.85-7.79 (2H, m), 7.71 (1H, dd, J=1.5, 8.1 Hz), 7.66 (1H, bd, J=8.1 Hz), 6.17 (1H, s), 3.52 (3H, s), 3.48 (2H, t, J=8.4 Hz), 3.27 (1H, m) 3.13 (9H, s), 2.97 (1H, m) 2.40 (1H, m), 2.20 (1H, m) and 2.15 (3H, s).

Example 14

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(3-methanesulfonyl-propyl)-dimethyl-ammonium formate

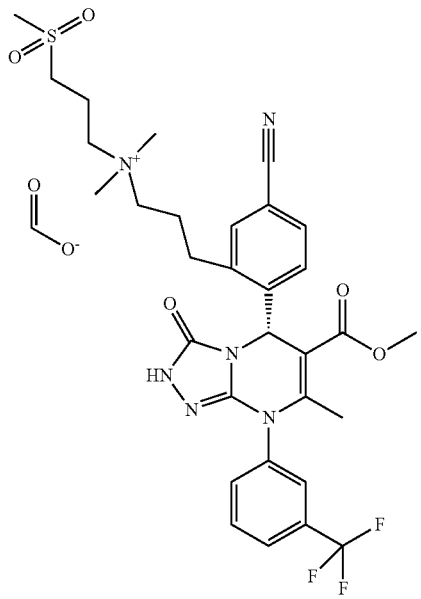

To a solution of Example 12 (150 mg, 0.28 mmol) in MeCN (2 mL) was added 1-bromo-3-methanesulfonyl-propane (225 mg, 1.12 mmol). The resulting mixture was heated at 90° C. for 40 minutes using microwave irradiation. The solvent was removed in vacuo and the resultant residue was purified by reverse phase chromatography (MDAP), giving the title compound as an off-white solid (65 mg)

LC-MS (Method 3): Rt=3.53 min, m/z=661.2 [M]$^+$ $^1$H NMR (400 MHz, DMSO) δ 11.44 (1H, bs), 8.46 (1H, s), 8.14 (1H, s), 7.97-7.91 (2H, m), 7.91-7.87 (2H, m), 7.73 (1H, dd, J=1.6, 8.2 Hz), 7.67 (1H, bd, J=8.2 Hz), 6.20 (1H, s), 3.54 (3H, s), 3.52 (2H, t, J=8.3 Hz), 3.45 (2H, t, J=8.3 Hz), 3.36-3.20 (4H, m), 3.14 (6H, s), 3.07 (3H, s), 2.98 (1H, m), 2.42 (1H, m), 2.26-2.14 (2H, m), 2.17 (3H, s)

The following examples were prepared from Example 12 and the appropriately substituted alkyl halide using an analogous method to Example 14.

| Example | Structure | Name | LC-MS (Method 3) | NMR |
|---|---|---|---|---|
| 15 | 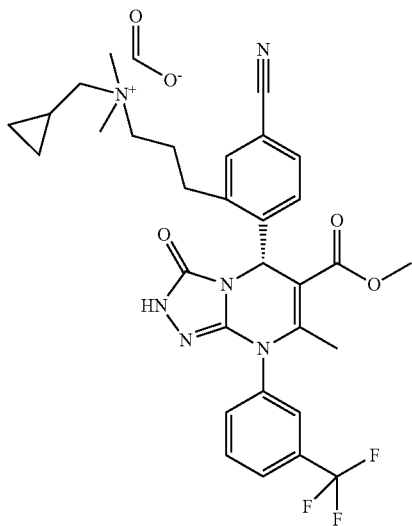 | (3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-cyclopropylmethyl-dimethyl-ammonium formate | Rt = 3.68 min, m/z = 595.2 [M]$^+$ | $^1$H NMR (400 MHz, DMSO) δ 11.44 (1H, bs), 8.44 (1H, s), 8.14 (1H, s), 7.98-7.91 (2H, m), 7.88-7.83 (2H, m), 7.73 (1H, dd, J = 1.5, 8.0 Hz), 7.67 (1H, bd, J = 8.2Hz), 6.20 (1H, s), 3.54 (3H, s), 3.52 (2H, t, J = 8.3 Hz), 3.34-3.24 (3H, m), 3.13 (6H, s), 2.99 (1H, m), 2.41 (1H, m), 2.21 (1H, m), 2.17 (3H, s), 1.22 (1H, m), 0.77-0.71 (2H, m), 0.48-0.41 (2H, m) |

| Example | Structure | Name | LC-MS (Method 3) | NMR |
|---|---|---|---|---|
| 16 | 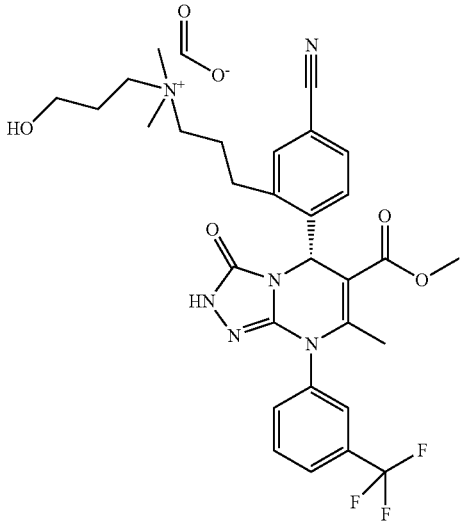 | (3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(3-hydroxy-propyl)-dimethyl-ammonium formate | Rt = 3.60 min, m/z = 599.3 [M]+ | $^1$H NMR (400 MHz, DMSO) δ 11.44 (1H, bs), 8.47 (1H, s), 8.14 (1H, s), 7.97-7.89 (2H, m), 7.87-7.80 (2H, m), 7.73 (1H, dd, J = 1.5, 8.0 Hz), 7.67 (1H, bd, J = 8.2Hz), 6.20 (1H, s), 3.54 (3H, s), 3.53-3.38 (7H, m), 3.27 (1H, m), 3.11 (6H, s), 2.99 (1H, m), 2.38 (1H, m), 2.18 (1H, m) 2.17 (3H, s) 1.94-1.85 (2H, m) |
| 17 | 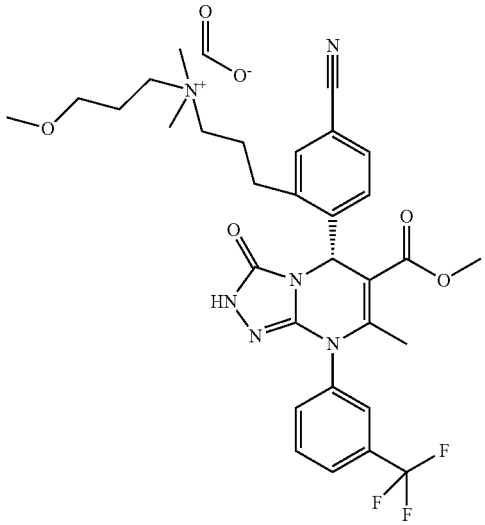 | (3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(3-methoxy-propyl)-dimethyl-ammonium formate | Rt = 3.79 min, m/z = 613.3 [M]+ | $^1$H NMR (400 MHz, DMSO) δ 11.46 (1H, bs), 8.45 (1H, s), 8.14 (1H, s), 7.97-7.90 (2H, m), 7.87-7.81 (2H, m), 7.73 (1H, dd, J = 1.5, 8.0 Hz), 7.67 (1H, bd, J = 8.2Hz), 6.20 (1H, s), 3.54 (3H, s), 3.51-3.37 (6H, m), 3.28 (3H, s), 3.26 (1H, m) 3.11 (6H, s), 2.98 (1H, m), 2.40 (1H, m), 2.18 (1H, m) 2.17 (3H, s) 2.04-1.95 (2H, m) |
| 18 | 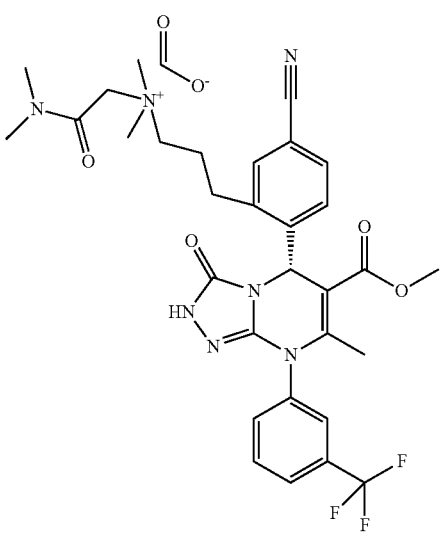 | (3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-dimethylcarbamoyl-methyl-dimethyl-ammonium formate | Rt = 3.73 min, m/z = 626.3 [M]+ | $^1$H NMR (400 MHz, DMSO) δ 11.46 (1H, bs), 8.48 (1H, s), 8.14 (1H, s), 7.97-7.91 (2H, m), 7.87-7.81 (2H, m), 7.73 (1H, dd, J = 1.5, 8.0 Hz), 7.67 (1H, bd, J = 8.2Hz), 6.17 (1H, s), 4.50 (2H, s) 3.77 (2H, t, J = 8.5 Hz) 3.54 (3H, s), 3.30 (6H, s), 3.29 (1H, m), 2.99 (3H, s), 2.97 (1H, m), 2.90 (3H, m) 2.44 (1H, m), 2.20 (1H, m) 2.17 (3H, s) |

Intermediate 12

(R)-5-[4-Cyano-2-(3-hydroxy-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

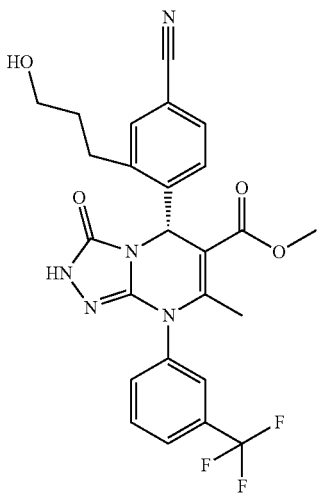 [SMILES: COC(=O)C1=C(C)N(c2cccc(C(F)(F)F)c2)c2n[nH]c(=O)n2[C@@H]1c1ccc(C#N)cc1CCCO]

To a solution of intermediate 11 (4.30 mmol) in MeOH (40 mL) at 5° C. was added sodium borohydride (163 mg, 4.30 mmol) portion-wise. The mixture was stirred for 30 mins and allowed to warm to RT. The solvent was removed in vacuo and the residue was partitioned between 1 N HCl and EtOAc. The aqueous layer was extracted with EtOAc (×2) and the combined organic extracts dried (Na$_2$SO$_4$) and concentrated in vacuo. The resulting residue was purified by chromatography eluting with a gradient of 0-10% MeOH in DCM to give the title compound as a yellow foam (990 mg).

LC-MS (Method 4): Rt=3.29 min, m/z=514 [M+H]$^+$

Intermediate 13

(R)-5-[2-(3-Bromo-propyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

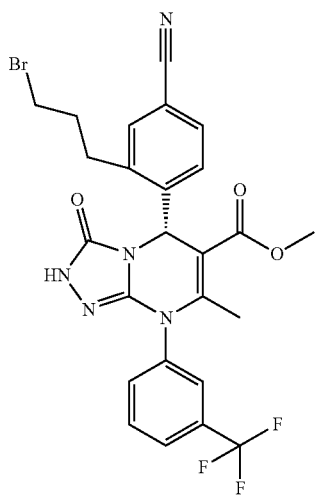 [SMILES: COC(=O)C1=C(C)N(c2cccc(C(F)(F)F)c2)c2n[nH]c(=O)n2[C@@H]1c1ccc(C#N)cc1CCCBr]

To a solution of intermediate 12 (780 mg, 1.52 mmol) in DCM (20 mL) at 5° C. was added carbon tetrabromide (756 mg, 2.28 mmol) followed by triphenylphosphine (598 mg, 2.28 mmol). The resulting mixture was stirred for 1.5 hours and allowed to warm to RT. The solution was diluted with DCM and washed with water and the organic layer dried (Na$_2$SO$_4$) and concentrated in vacuo. The resulting residue was purified by chromatography eluting from 0-50% EtOAc in cyclohexane to give the title compound as a yellow foam (620 mg).

LC-MS (Method 4): Rt=3.90 min, m/z=576/578 [M+H]$^+$ (Br isotopic pattern)

Example 19

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-1-azonia-bicyclo[2.2.2]octane formate

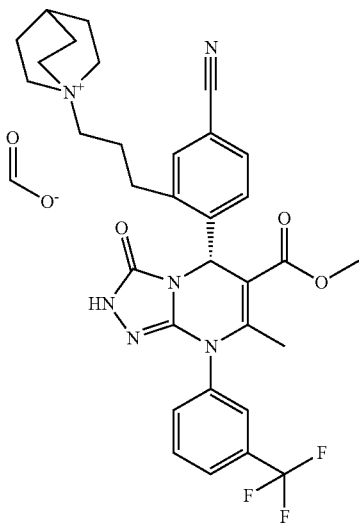

To a solution of Intermediate 13 (100 mg, 0.17 mmol) in MeCN (2 mL) was added quinuclidine (77 mg, 0.69 mmol). The mixture was heated at 90° C. for 30 mins using microwave irradiation. The solvent was removed in vacuo and the residue was purified by reverse phase chromatography (MDAP), giving the title compound as an off-white solid (98 mg).

LC-MS (Method 3): Rt=3.80 min, m/z=607.3 [M]$^+$ $^1$H NMR (400 MHz, DMSO) δ 11.52 (1H, bs), 8.45 (1H, s), 8.14 (1H, s), 7.97-7.91 (2H, m), 7.87-7.81 (2H, m), 7.73 (1H, dd, J=1.6, 8.2 Hz), 7.67 (1H, bd, J=8.2 Hz), 6.19 (1H, s), 3.54 (3H, s), 3.51-3.43 (6H, m), 3.34-3.22 (3H, m), 2.95 (1H, m), 2.36 (1H, m) 2.17 (3H, s), 2.17 (1H, m) 2.10 (1H, m), 1.93-1.85 (6H, m)

The following examples were prepared from Intermediate 13 and the appropriately substituted tertiary amine using an analogous method to Example 19.

| Example | Structure | Name | LC-MS (Method 3) | NMR |
|---|---|---|---|---|
| 20 | 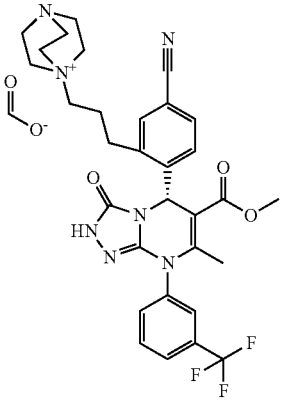 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-4-aza-1-azonia-bicyclo[2.2.2]octane formate | Rt = 3.52 min, m/z = 608.2 [M]⁺ | ¹H NMR (400 MHz, DMSO) δ 11.46 (1H, bs), 8.49 (1H, s), 8.14 (1H, s), 7.97-7.91 (2H, m), 7.87-7.81 (2H, m), 7.73 (1H, dd, J = 1.5, 8.0 Hz), 7.67 (1H, bd, J = 8.2 Hz), 6.20 (1H, s), 3.56-3.30 (8H, m), 3.54 (3H, s), 3.29 (1H, m) 3.10-3.03 (6H, m), 2.97 (1H, m), 2.40 (1H, m), 2.18 (1H, m) 2.17 (3H, s) |
| 21* | 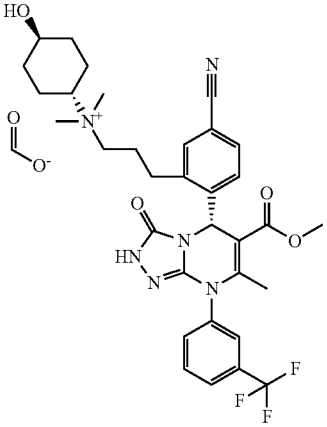 | (3-{5-Cyano-2-[(R)-6-methoxycarbonyl-7-methyl-3-oxo-8-(3-trifluoromethyl-phenyl) 2,3,5,8-tetrahydro-[1,2,4]triazolo[4,3-a]pyrimidin-5-yl]-phenyl}-propyl)-(4-hydroxy-cyclohexyl)-dimethyl-ammonium formate | Rt = 2.93 min, m/z = 639.3 [M]⁺ | ¹H NMR (400 MHz, DMSO) δ 11.42 (1H, bs), 8.47 (1H, s), 8.12 (1H, s), 7.97-7.99 (2H, m), 7.87-7.79 (2H, m), 7.73-7.62 (2H, m), 6.19 (1H, s), 3.65-3.38 (3H, m, partially obscured by water peak), 3.54 (3H, s), 3.22 (1H, m), 3.03 (3H, s), 3.01 (3H, s), 2.93 (1H, m), 2.40 (1H, m), 2.17 (1H, m) 2.15 (3H, s), 2.07 (2H, m), 1.93 (2H, m), 1.59 (2H, m) 1.28 (2H, m) |
| 22 | 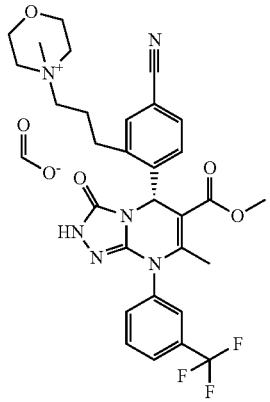 | 4-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-4-methyl-morpholin-4-ium formate | Rt = 3.63 min, m/z = 597.3 [M]⁺ | ¹H NMR (400 MHz, DMSO) δ 11.52 (1H, bs), 8.50 (1H, s), 8.12 (1H, bs), 7.95-7.90 (2H, m), 7.85-7.80 (2H, m), 7.71 (1H, dd, J = 1.6, 8.1 Hz), 7.65 (1H, bd, J = 8.1 Hz), 6.20 (1H, s), 3.96 (4H, m), 3.65 (2H, m, partially obscured by water peak), 3.54 (3H, s), 3.49 (4H, m), 3.29 (1H, m), 3.14 (3H, s), 2.98 (1H, m), 2.41 (1H, m), 2.20 (1H, m) 2.17 (3H, s) |

| Example | Structure | Name | LC-MS (Method 3) | NMR |
|---|---|---|---|---|
| 23* | 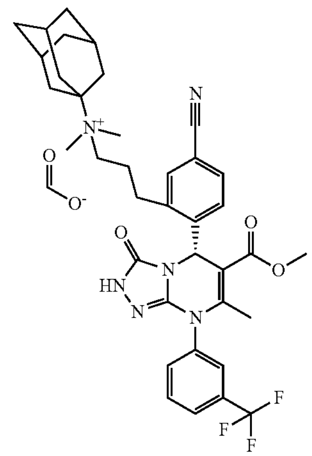 | Adamantan-1-yl-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-ammonium formate | Rt = 3.33 min, m/z = 675.4 [M]+ | $^1$H NMR (400 MHz, DMSO) δ 11.43 (1H, bs), 8.47 (1H, s), 8.12 (1H, bs), 7.96-7.87 (2H, m), 7.87-7.78 (2H, m), 7.72-7.62 (2H, m), 6.21 (1H, s), 3.52 (3H, s), 3.36 (2H, m, partially obscured by water peak), 3.22 (1H, m), 2.90 (1H, m), 2.90 (3H, s), 2.88 (3H, s) 2.43 (1H, m), 2.25 (3H, bs), 2.13 (3H, s), 2.08 (7H, m) 1.66 (6H, m) |

* = Alternative Acquity UPLC BEH Shield RP18 1.7 micron 100 mm × 2.1 mm used in LCMS method Intermediate 14

(R)-5-(2-Bromomethyl-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

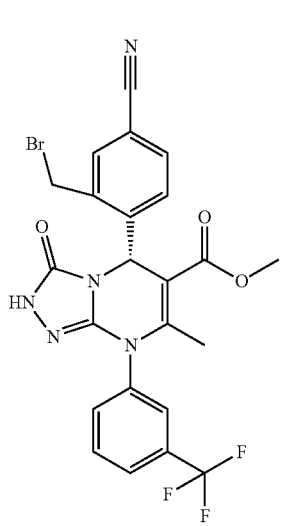 [SMILES: COC(=O)C1=C(C)N(c2cccc(C(F)(F)F)c2)c2n[nH]c(=O)n2[C@@H]1c1ccc(C#N)cc1CBr]

The title compound was prepared from Intermediate 4b (0.5 g, 1.03 mmol) using analogous methods to those employed to make Intermediate 9 and gave the title compound as a colourless gum (1.26 g).

LC-MS (Method 4); Rt=3.70 min, m/z=548.0 [M($^{79}$Br)+H]+

Example 24

4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-morpholin-4-ium formate

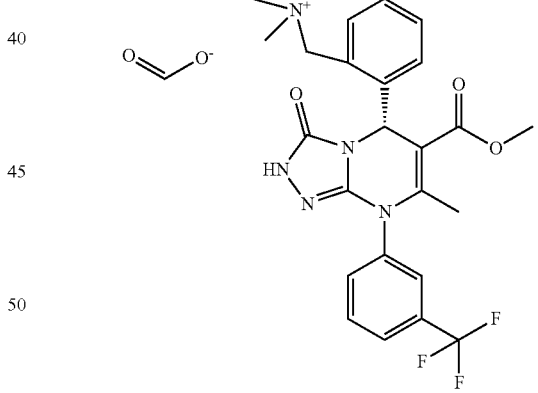

Intermediate 14 (110 mg, 0.2 mmol) was heated in N-methylmorpholine (6 mL) under argon for 11 h at 50° C. The resultant material was partitioned between EtOAc and water, and the aqueous layer was separated and subjected to purification by HPLC (System 1). The crude product fractions were concentrated to remove MeCN and treated with concentrated aqueous ammonia (10% by volume) for 15 min at room temperature. The solution was further purified by chromatography using a C$_{18}$ Isolute cartridge and eluting from 0-30% MeCN (+0.1% HCO$_2$H) to give, following freeze drying, the title product as a white solid (34 mg).

LC-MS (Method 3): Rt=3.37 min, m/z=569.2 [M]+

$^1$H NMR (400 MHz, DMSO-D$_6$) δ 8.43 (1.H, s), 8.10 (2H, m), 8.03 (1H, dd, J=8.0, 1.5 Hz), 7.95-7.79 (4H, m), 6.54 (1H, s), 5.22 (1H, d, J=13.8 Hz), 5.10 (1H, d, J=13.8 Hz), 4.09-3.53 (8H, m), 3.54 (3H, s), 3.28 (3H, s) and 2.07 (3H, s).

The following examples were prepared from Intermediate 14 using an analogous method to Example 24.

| Example | Structure | Name | LC-MS (Method 3) | NMR |
|---|---|---|---|---|
| 25 | 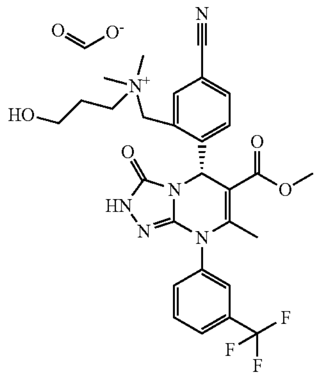 | {5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-hydroxy-propyl)-dimethyl-ammonium formate | Rt = 3.27 min, m/z = 571.2 [M]$^+$ | $^1$H NMR (400 MHz, DMSO) δ 11.5 (1H, bs), 8.45 (1H, s), 8.13 (1H, d, J = 1.5 Hz), 8.1 (1H, bs), 8.02 (1H, dd, J = 8, 1.5 Hz). 7.95-7.79 (4H, m), 6.48 (1H, s), 5.11 (1H, d, J = 14.0 Hz), 4.96 (1H, d, J = 14.0 Hz), 3.64, (2H, m), 3.56 (2H, m), 3.53 (3H, s), 3.21 (3H, s), 3.16 (3H, s), 2.07 (3H, s) and 2.02 (2H, m) |
| 26 | 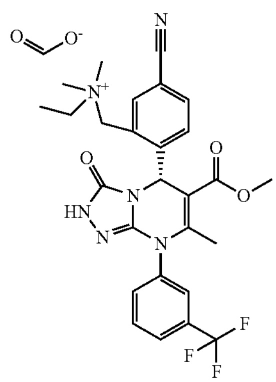 | {5-cyano-2-[(R)-6-methoxycarbonyl-7-methyl-3-oxo-8-(3-trifluoromethyl-phenyl) 2,3,5,8-tetrahydro-[1,2,4]triazolo[4,3-a]pyrimidin-5-yl]-benzyl}-ethyl-dimethyl-ammonium formate | Rt = 3.39 min, m/z = 541.2 [M]$^+$ | $^1$H NMR (400 MHz, DMSO) δ 11.41 (1H, bs), 8.41 (1 H, s), 8.12-8.08 (m, 2H), 8.02 (1H, dd, J = 8.0, 1.5 Hz). 7.95-7.79 (4H, m), 6.47 (1H, s), 5.10 (1H, d, J = 14.0 Hz), 4.94 (1H, d, J = 14.1 Hz), 3.65-3.56 (2H, m), 3.5 (3H, s), 3.18 (3H, s), 3.14 (3H, s), 2.07 (3H, s) and 1.39 (3H, t, J = 7.2 Hz) |
| 27 | 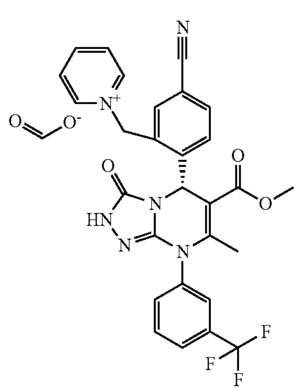 | 1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium formate | Rt = 3.40 min, m/z = 547.2 [M]$^+$ | $^1$H NMR (400 MHz, DMSO) δ 9.36 (2H, d, J = 5.9 Hz), 8.69 (1H, t, J = 7.6 Hz), 8.39 (1.9 H, s), 8.24 (2H, m), 8.16 (1H, bs), 7.96-7.90 (3H, m), 7.86-7.81 (3H, m), 7.77 (1H, m), 6.56 (1H, d, J = 15.1 Hz), 6.14 (1H, d, J = 15.1 Hz), 6.42 (1H, s), 3.55 (3H, s) and 2.18 (3H, s) |

| Example | Structure | Name | LC-MS (Method 3) | NMR |
|---|---|---|---|---|
| 28 | 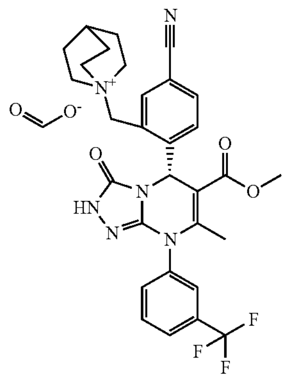 | 1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-azonia-bicyclo[2.2.2]octane formate | Rt = 3.48 min, m/z = 579.3 [M]⁺ | ¹H NMR (400 MHz, DMSO) δ 11.49 (1H, bs), 8.37 (1H, s), 8.10 (1H, bs), 8.08 (1H, d, J = 1.6 Hz), 8.01 (1H, dd, J = 8.3, 1.6 Hz). 7.95-7.79 (4H, m), 6.43 (1H, s), (1H, d, J = 14.4 Hz), 4.86 (1H, d, J = 14.4 Hz), 3.78-3.68 (3H, m), 3.65-3.55 (3H, m), 3.53 (3H, s), 2.11-2.06 (1H, m), 2.07 (3H, s) and 1.95-1.85 (6H, m) |
| 29 | 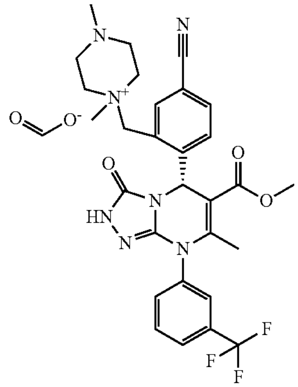 | 1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1,4-dimethyl-piperazin-1-ium formate | Rt = 2.99 min, m/z = 582.2 [M]⁺ | ¹H NMR (400 MHz, DMSO) δ 11.48 (1H, bs), 8.42 (1H, s), 8.12-8.08 (m, 2H), 8.02 (1H, dd, J = 8.1, 1.6 Hz). 7.95-7.79 (4H, m), 6.51 (1H, s), 5.18 (1H, d, J = 14.1 Hz), 5.05 (1H, d, J = 14.1 Hz), 3.84-3.74 (2H, m), 3.63-3.53 (2H, m), 3.54 (3H, s), 3.15 (3H, s), 2.88-2.79 (2H, m), 2.72-2.61 (2H, m), 2.31 (3H, s) and 2.07 (3H, s)) |
| 30 | 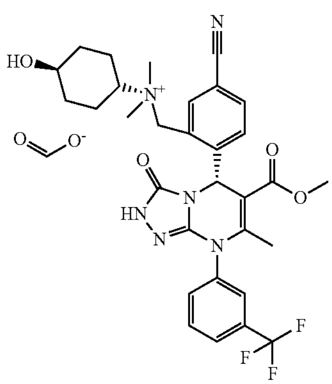 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(4-hydroxy-cyclohexyl)-dimethyl ammonium formate | Rt = 3.33 min, m/z = 611.2 [M]⁺ | ¹H NMR (400 MHz, DMSO) δ 11.4 (1H, bs), 8.45 (1H, s), 8.12-8.07 (m, 2H), 8.02 (1H, dd, J = 8.1, 1.6 Hz). 7.95-7.79 (4H, m), 6.35 (1H,s), 5.17 (1H, d, J = 13.8 Hz), 4.86 (1H, d, J = 13.8 Hz), 3.77-3.68 (1H, m), 3.53 (3H, s), 3.54-3.45 (1H, m), 3.17 (3H, s), 3.04 (3H, s), 2.36-2.27 (2H, m), 2.10-2.00 (2H, m), 2.09 (3H, s), 1.84-1.68 (2H, m) and 1.38-1.23 (2H, m) |
| 31 | 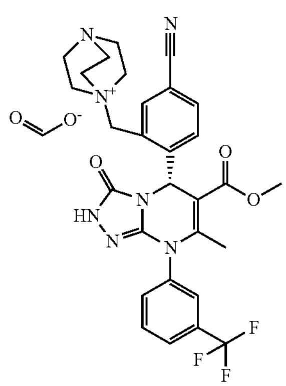 | 1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-aza-1-azonia-bicyclo[2.2.2]octane formate | Rt = 3.23 min, m/z = 580.2 [M]⁺ | ¹H NMR (400 MHz, DMSO) δ 11.48 (1H, bs), 8.44 (1H, s), 8.10 (1H, bs), 8.08 (1H, d, J = 1.7 Hz), 8.02 (1H, dd, J = 8.2, 1.7 Hz). 7.95-7.79 (4H, m), 6.45 (1H, s), 5.10 (1H, d, J = 14.4 Hz), 4.95 (1H, d, J = 14.4 Hz), 3.67-3.58 (3H, m), 3.55-3.46 (3H, m), 3.53 (3H, s), 3.10-3.02 (6H, m) and 2.08 (3H, s) |

| Example | Structure | Name | LC-MS (Method 3) | NMR |
|---------|-----------|------|------------------|-----|
| 32** | 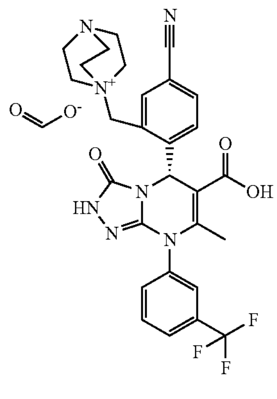 | 1-{2-[(R)-6-carboxy-7-methyl-3-oxo-8-(3-trifluoromethyl-phenyl)-2,3,5,8-tetrahydro-[1,2,4]triazolo[4,3-a]pyrimidin-5-yl]-5-cyano-benzyl}-4-aza-1-azonia-bicyclo[2.2.2]octane formate | Rt = 3.00 min, m/z = 566.2 [M]+ | $^1$H NMR (400 MHz, DMSO) δ 11.04 (1H, bs), 8.27 (1 H, s), 8.02 (1H, d, J = 1.7 Hz), 7.92 (1H, bs), 7.95 (1H, dd, J = 8.3, 1.7 Hz). 7.95-7.72 (3H, m), 7.62 (1H, d, J = 8.3 Hz), 6.37 (1H, s), 5.44 (1H, d, J = 14.3 Hz), 4.87 (1H, d, J = 14.3 Hz), 3.67-3.47 (6H, m), 3.08-2.99 (6H, m) and 2.04 (3H, s) |
| 33 | 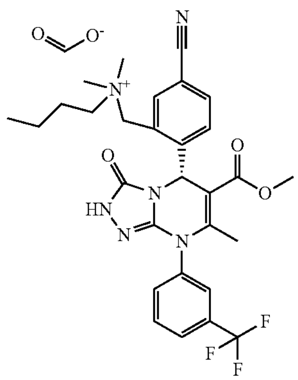 | Butyl-{5-cyano-2-[(R)-6-methoxy carbonyl-7-methyl-3-oxo-8-(3-trifluoromethyl-phenyl)-2,3,5,8-tetrahydro [1,2,4]triazolo[4,3-a]pyrimidin-5-yl]-benzyl}-dimethyl-ammonium formate | Rt = 3.64 min, m/z = 569.3 [M]+ | $^1$H NMR (400 MHz, DMSO) δ 11.51 (1H, bs), 8.42 (1H, s), 8.12-8.09 (m, 2H), 8.02 (1H, dd, J = 8.2, 1.7 Hz). 7.95-7.79 (4H, m), 6.46 (1H, s), 5.11 (1H, d, J = 14.2 Hz), 4.95 (1H, d, J = 14.2 Hz), 3.61-3.47 (2H, m, partially obscured by water peak), 3.53 (3H, s), 3.20 (3H, s), 3.15 (3H, s), 2.07 (3H, s) 1.87-1.77 (2H, m), 1.44-1.34 (2H, m) and 0.98 (3H, t, J = 7.3 Hz) |
| 34 | 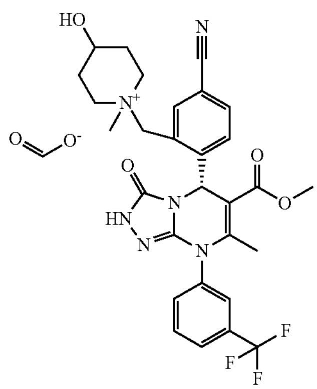 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-hydroxy-1-methyl-piperidinium formate | Rt = 3.39 min, m/z = 583.2 [M]+ | $^1$H NMR (400 MHz, DMSO) δ 11.40 (1H, bs), 8.42 (1H, s), 8.15-8.06 (m, 2H), 8.02 (1H, bd, J = 8.2). 7.95-7.79 (4H, m), 6.48, 6.50 (1H, 2s), 5.2-4.97 (2H, m), 3.92-3.2 (5H, m, partially obscured by water peak), 3.53 (3H, s), 3.16, 3.13 (3H, 2s), 2.18-1.98 (2H, m), 2.07 (3H, s), 1.91-1.75 (2H, m) |
| 35 | 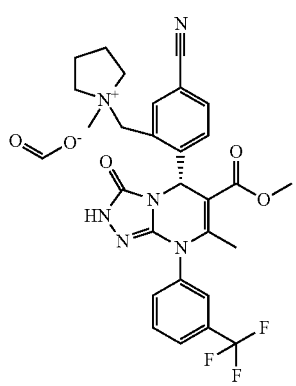 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-methyl-pyrrolidinium formate | Rt = 3.53 min, m/z = 553.2 [M]+ | $^1$H NMR (400 MHz, DMSO) δ 11.3 (1H, bs), 8.43 (1H, s), 8.14-8.09 (m, 2H), 8.00 (1H, dd, J = 8.2, 1.6 Hz). 7.95-7.79 (4H, m), 6.48 (1H, s), 5.18 (1H, d, J = 14.2 Hz), 5.09 (1H, d, J = 14.2 Hz), 3.88-3.71 (4H, m), 3.53 (3H, s), 3.05 (3H, s), 2.22-2.1 (4H, m) and 2.09 (3H, s) |

| Example | Structure | Name | LC-MS (Method 3) | NMR |
|---|---|---|---|---|
| 36 | 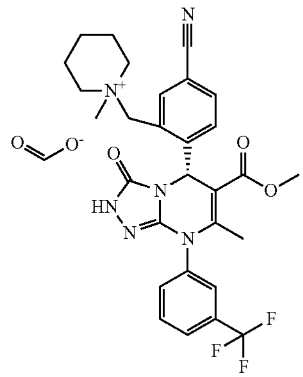 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-methyl-piperidinium formate | Rt = 3.57 min, m/z = 567.2 [M]+ | $^1$H NMR (400 MHz, DMSO) δ 8.41 (1H, s), 8.13-8.06 (m, 2H), 8.02 (1H, dd, J = 8.2, 1.5 Hz). 7.95-7.79 (4H, m), 6.49 (1H, s), 5.13 (1H, d, J = 14.2 Hz), 5.00 (1H, d, J = 14.2 Hz), 3.73-3.48 (4H, m), 3.54 (3H, s), 3.15 (3H, s), 2.07 (3H, s) 2.01-1.78 (4H, m) 1.74-1.65 (1H, m) and 1.55-1.41 (1H, m) |
| 37 | 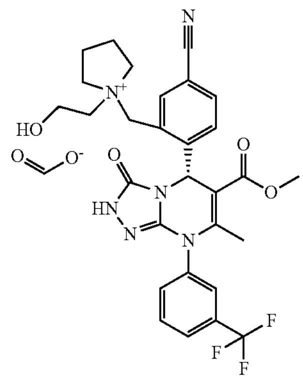 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-(2-hydroxy-ethyl)-pyrrolidinium formate | Rt = 3.50 min, m/z = 583.2 [M]+ | $^1$H NMR (400 MHz, DMSO) δ 8.42 (1H, s), 8.16 (1H, d, J = 1.5 Hz), 8.11 (1H, bs), 7.98 (1H, dd, J = 1.5, 8.2 Hz), 7.95-7.79 (4H, m), 6.41 (1H, s), 5.30 (1H, d, J = 14.8 Hz), 5.19 (1H, d, J = 14.8 Hz), 4.03-3.92 (2H, m), 3.90-3.82 (4H, m), 3.75-3.48 (2H, m), 3.54 (3H, s), 2.15-2.04 (4H, m) and 2.08 (3H, s) |
| 38 | 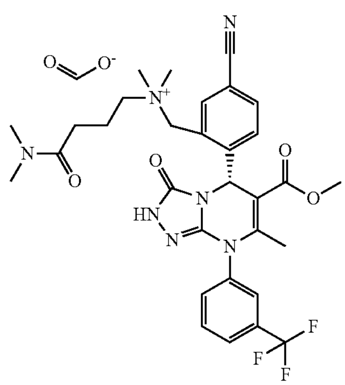 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-dimethylcarbamoyl-propyl)-dimethyl-ammonium formate | Rt = 3.50 min, m/z = 626.2 [M]+ | $^1$H NMR (400 MHz, DMSO) δ 8.43 (1H, s), 8.16 (1H, d, J = 1.6 Hz), 8.10 (1H, bs), 8.01 (1H, dd, J = 1.6, 8.2 Hz), 7.95-7.79 (4H, m), 6.48 (1H, s), 5.10 (1H, d, J = 14.1 Hz), 4.98 (1H, d, J = 14.1 Hz), 3.57-3.51 (2H, m), 3.54 (3H, s), 3.22 (3H, s), 3.18 (3H, s) 2.97 (3H, s), 2.85 (3H, s) 2.46 (2H, t, J = 6.7 Hz), 2.14-2.02 (2H, m), 2.07 (3H, s) |
| 39 | 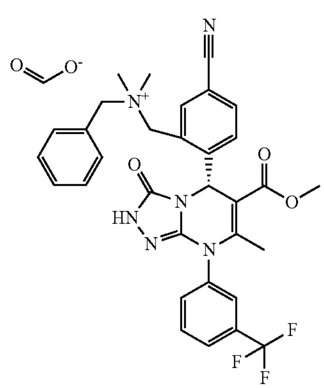 | Benzyl-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-ammonium formate | Rt = 3.80 min, m/z = 603.3 [M]+ | $^1$H NMR (400 MHz, DMSO) δ 11.48 (1H, bs), 8.40 (1.7H, s), 8.17 (1H, d, J = 1.6 Hz), 8.10 (1H, bs), 8.03 (1H, dd, J = 1.6, 8.3 Hz), 7.95-7.79 (4H, m), 7.66-7.51 (5H, m), 6.49 (1H, s), 5.26 (1H, d, J = 14.1 Hz), 5.03 (1H, d, J = 14.1 Hz), 4.87 (1H, d, J = 12.4 Hz), 4.74 (1H, d, J = 12.4 Hz), 3.50 (3H, s) 3.13 (3H, s), 3.11 (3H, s) and 2.08 (3H, s) |

**Example 32 was formed as a by-product during the preparation of Example 31 and was isolated during HPLC purification.

Example 40

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium bromide

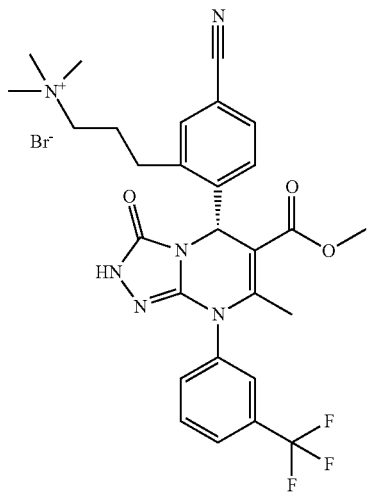

To a solution of Example 12 (2.0 g, 3.70 mmol) in MeCN (10 mL) at 5° C. was added a 26% solution of methyl bromide in acetonitrile (10 mL) drop-wise. The mixture was allowed to warm to room temperature and stirred for 2 hours. The solvent was evaporated in vacuo. The resulting residue was taken up in 30% MeCN in water (30 mL) and freeze dried to yield a white solid (2.05 g).

LC-MS (Method 3): Rt=3.48 min, m/z=555.2 [M]$^+$ $^1$H NMR (400 MHz, DMSO) δ 11.26 (1H, s), 8.14 (1H, s), 7.96-7.92 (2H, m), 7.87-7.82 (2H, m), 7.73 (1H, dd, J=1.5, 8.1 Hz), 7.68 (1H, bd, J=8.1 Hz), 6.19 (1H, s), 3.54 (3H, s), 3.51 (2H, t, J=8.4 Hz), 3.30 (1H, m) 3.15 (9H, s), 2.99 (1H, m) 2.42 (1H, m), 2.22 (1H, m) and 2.17 (3H, s).

Example 41

(S)-5-[4-Cyano-2-(5-hydroxypentyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

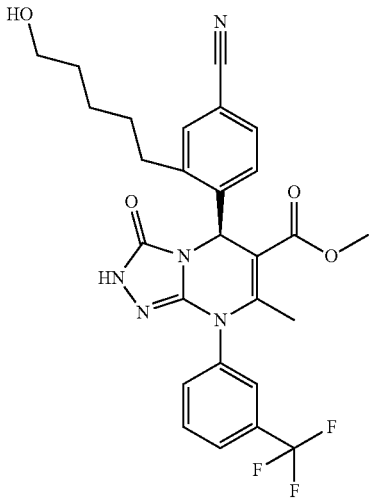 [SMILES: COC(=O)C1=C(C)N(c2cccc(C(F)(F)F)c2)c2n[nH]c(=O)n2[C@H]1c1ccc(C#N)cc1CCCCCO]

To pent-4-en-1-ol (51 mg) under argon at 0° C. was added a solution of 9-BBN (0.5 M in THF, 2.24 ml). The solution was then stirred at RT 2 hours. Cesium carbonate (241 mg, 0.74 mmol), Intermediate 4a (200 mg, 0.37 mmol), PdCl$_2$(dppf).DCM (30 mg, 0.037 mmol) and water (0.2 mL) were then added. The mixture was heated at reflux for 6 hours then DMF (1 mL) was added and the THF distilled off under a stream of argon. The reaction was heated at 115° C. under argon for a further 1.5 hours. The mixture was cooled and diluted with EtOAc and water and the organic extract was dried (Na$_2$SO$_4$) and concentrated in vacuo. The resultant residue was purified by chromatography, eluting with 0-10% methanol in DCM, and then by HPLC (System 1) eluting from 20-80% MeCN in water (+0.1% HCO$_2$H) to give the title compound as a colourless gum, (25 mg).

C-MS (Method 1): Rt=3.24 min, m/z=542.1 [M+H]$^+$ $^1$H NMR (400 MHz, CDCl$_3$) δ 9.69 (1H, s), 7.80 (1H, d, J=7.8 Hz), 7.72 (1H, t, J=7.8 Hz), 7.63 (1H, s), 7.58 (1H, d, J=7.8 Hz), 7.5 (1H, bs), 7.48 (1H, bd, J=7.4 Hz), 7.33 (1H, d, J=7.4 Hz), 6.29 (1H, s), 3.59 (3H, s), 3.55 (2H, t, J=6.16 Hz), 3.33-3.24 (1H, m), 2.95-2.85 (1H, m), 2.24 (3H, s), 1.90-1.68 (2H, m), 1.68-1.47 (4H, m).

Example 42

(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium benzenesulfonate

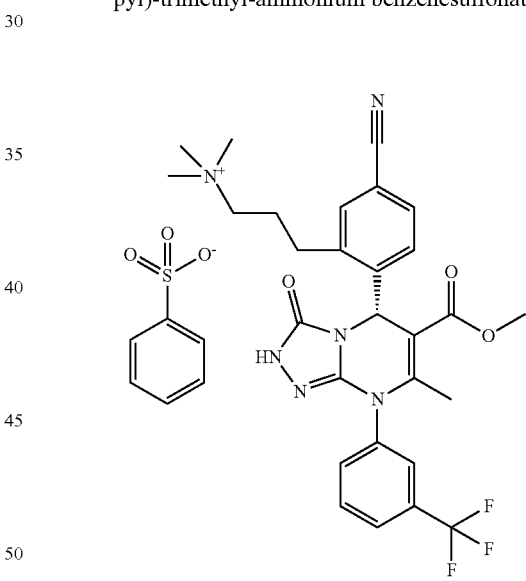

Amberlite IRA 458 'chloride' resin (40 g, wet) was converted to the besylate equivalent by passing a solution of benzene sulphonic acid (400 mL, 10% aqueous solution) through the resin in a glass column at a slow rate of 5-10 mL/minute. Following this, the resin was washed with water until the filtrate had a pH of ~5/6. The resin was stored "damp" prior to use. A solution of Example 40 (1 g, 1.57 mmol) in a round-bottom flask (250 mL) was treated with 30% MeCN/water (60 mL) and then mixed with the besylate resin (40 g, wet). The resulting mixture was gently agitated by slowly rotating the flask on a Buchi evaporator for 50 minutes at atmospheric pressure. The contents were placed in a resin tube, then filtered and washed with 30% MeCN/water and the filtrate was freeze dried to give the title compound as a white electrostatic solid (1.01 g).

LC-MS (Method 3): Rt=3.47 min, m/z=555.4 [M]⁺

¹H NMR (400 MHz, DMSO) δ 11.24 (1H, s), 8.12 (1H, s), 7.96-7.89 (2H, m), 7.86-7.80 (2H, m), 7.74-7.63 (2H, m), 7.63-7.55 (2H, m, besylate), 7.35-7.27 (3H, m, besylate), 6.17 (1H, s), 3.52 (3H, s), 3.51-3.43 (2H, m), 3.32-3.21 (1H, m) 3.13 (9H, s), 3.03-2.91 (1H, m) 2.40 (1H, m), 2.20 (1H, m), 2.15 (3H, s).

Example 43

(5-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-pentyl)-trimethyl-ammonium formate

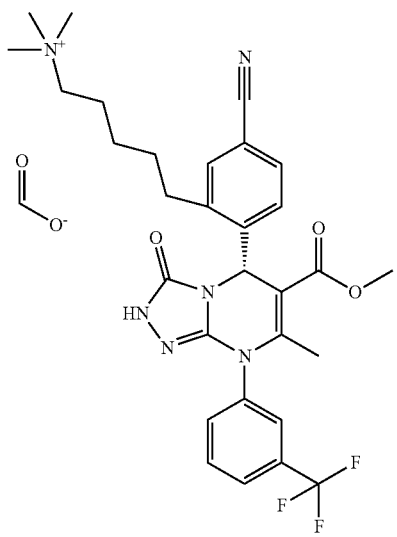

Intermediate 15

(R)-5-[2-(5-Bromo-pentyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

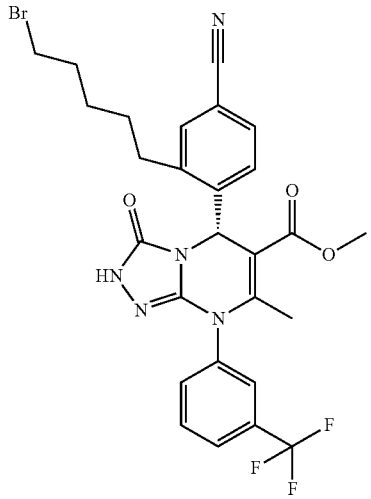 [SMILES: COC(=O)C1=C(C)N(c2cccc(C(F)(F)F)c2)c2n[nH]c(=O)n2[C@@H]1c1ccc(C#N)cc1CCCCCBr]

The title compound was prepared from Intermediate 4b (240 mg, 0.45 mmol) using analogous methods to those used for Example 41 and Intermediate 13 and gave the desired compound as a yellow gum (90 mg).

LC-MS (Method 3): Rt=4.12 min, m/z=604 [M(⁷⁹Br)+H]⁺

(5-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-pentyl)-trimethyl-ammonium formate (Example 43)

The title compound was prepared from Intermediate 15 (89 mg, 0.15 mmol) using an analogous method to that used for Example 7 and gave the desired compound as a yellow gum (10 mg) following chromatographic purification (HPLC system 1).

LC-MS (Method 3): Rt=3.66 min, m/z=583.3 [M]⁺

¹H NMR (400 MHz, DMSO) δ 11.28 (1H, bs), 8.42 (1.6H, s, formate), 8.09 (1H, s), 7.95-7.86 (2H, m), 7.84-7.77 (1H, m), 7.69-7.58 (3H, m), 6.18 (1H, s), 3.51 (3H, s), 3.37-3.28 (2H, m) 3.26-3.14 (1H, m), 3.06 (9H, s), 3.07-2.95 (1H, m), 2.14 (3H, s), 1.93-1.70 (4H, m), 1.51-1.39 (2H, m).

Example 44

(4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-trimethyl-ammonium formate

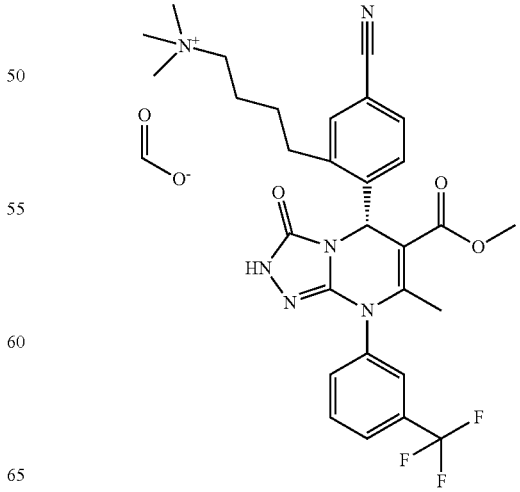

Intermediate 16

(R)-5-[2-(5-Bromo-pentyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester.

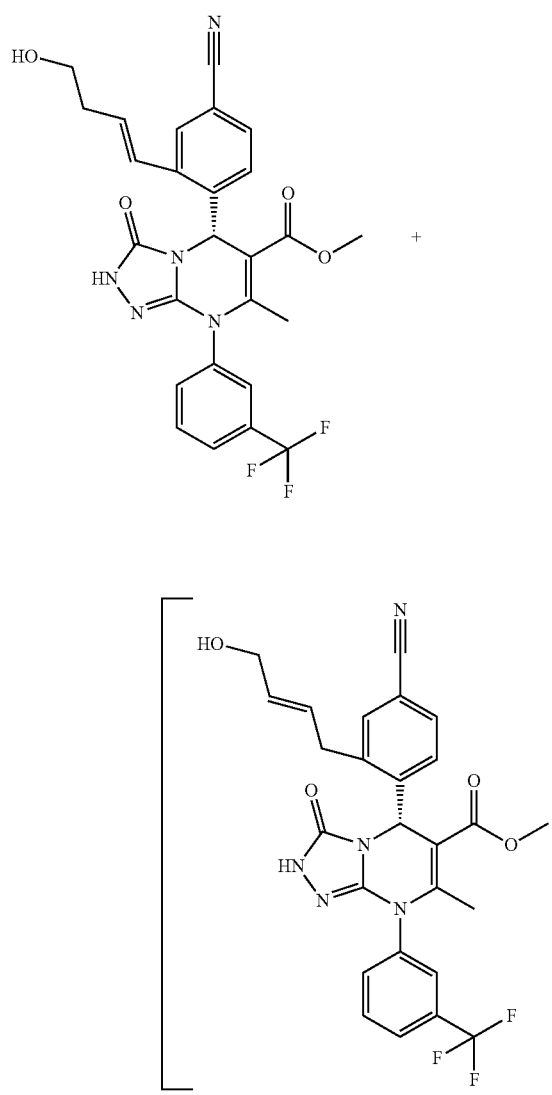

To a mixture of Intermediate 4b (1.0 g, 1.87 mmol), but-3-en-1-ol (270 mg, 3.74 mmol), tri-tertiary-butyl phosphonium tetrafluoroborate (100 mg, 0.34 mmol), $Pd_2(dba)_3$ (90 mg, 0.10 mmol) and dicyclohexyl-methyl-amine (1.80 mL, 8.42 mmol) was added DMF (10 mL) and the resulting solution degassed under Argon. The mixture was then heated at 95° C. for 18 hours. The mixture was cooled, diluted with EtOAc and aqueous 10% citric acid and the organic extract was washed with brine, then dried ($Na_2SO_4$) and concentrated in vacuo. The resultant residue was purified by chromatography, eluting with 0-5% MeOH in DCM to give the title compound as a yellow solid (816 mg), which was contaminated with over 50% of an isomeric by-product (shown above). This material was used without further purification.

LC-MS (Method 4): Rt=3.35 min, m/z=526.2 [M+H]$^+$

Intermediate 17

(R)-5-[2-(4-Bromo-butyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

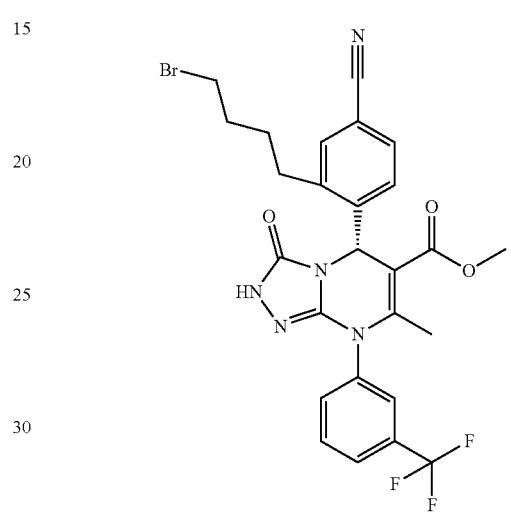

The title compound was prepared from Intermediate 16 (270 mg, 0.51 mmol) using analogous methods to those used for Example 5 and Intermediate 13 and gave the desired compound as a white solid (260 mg).

LC-MS (Method 4): Rt=3.99 min, m/z=589.9[M($^{79}$Br)+H]$^+$ (4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-trimethyl-ammonium formate (Example 44)

The title compound was prepared from Intermediate 17 (80 mg, 0.13 mmol) using an analogous method to that used for Example 7 and gave the desired compound as an electrostatic solid (44 mg) following chromatographic purification (HPLC system 1).

LC-MS (Method 3):) Rt=3.52 min, m/z=569.3 [M]$^+$ $^1$H NMR (400 MHz, DMSO) δ 11.40 (1H, bs), 8.49 (1H, s, formate), 8.11 (1H, s), 7.95-7.87 (2H, m), 7.85-7.79 (1H, m), 7.74-7.70 (1H, m), 7.70-7.61 (2H, m), 6.18 (1H, s), 3.52 (3H, s), 3.43-3.35 (2H, m) 3.28-3.18 (1H, m), 3.09 (9H, s), 3.18-3.05 (1H, m, obscured), 2.14 (3H, s), 1.95-1.80 (3H, m), 1.80-1.67 (1H, m).

The following examples were prepared from Intermediate 17 and the appropriately substituted tertiary amines using an analogous method to Example 44.

| Example | Structure | Name | LC-MS (Method 3) | NMR |
|---|---|---|---|---|
| 45 | 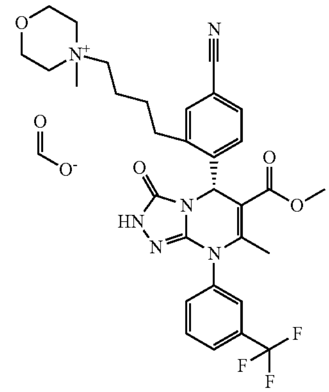 | 1-(4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-1-azonia-bicyclo[2.2.2]octane formate | Rt = 3.53 min, m/z = 611.3 [M]+ | $^1$H NMR (400 MHz, DMSO) δ 11.41 (1H, bs), 8.45 (1.4H, s, formate), 8.11 (1H, s), 7.95-7.86 (2H, m), 7.85-7.79 (1H, m), 7.73-7.70 (1H, m), 7.72-7.61 (2H, m), 6.19 (1H, s), 4.00-3.89 (4H, m), 3.59-3.50 (2H, m), 3.51 (3H, s), 3.48-3.39 (4H, m), 3.30-3.19 (1H, m), 3.16 (3H, s), 3.13-3.00 (1H, m), 2.15 (3H, s), 1.97-1.72 (4H, m). |
| 46 | 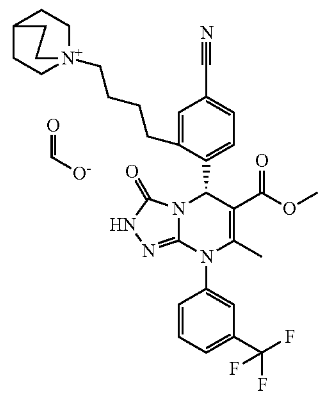 | 1-(4-{5-Cyano-2-[(R)-6-methoxycarbonyl 7-methyl-3-oxo-8-(3-trifluoromethyl-phenyl)-2,3,5,8-tetrahydro-[1,2,4]triazolo[4,3-a]pyrimidin-5-yl]-phenyl}-butyl)-1-azonia-bicyclo[2.2.2]octane formate | Rt = 3.68 min, m/z = 621.3 [M]+ | $^1$H NMR (400 MHz, DMSO) δ 11.39 (1H, bs), 8.41 (1.8H, s, formate), 8.11 (1H, bs), 7.96-7.87 (2H, m), 7.85-7.79 (1H, m), 7.72-7.70 (1H, m), 7.70-7.60 (2H, m), 6.17 (1H, s), 3.51 (3H, s), 3.44-3.56 (6H, m), 3.28-3.15 (3H, m), 3.11-3.00 (1H, m), 2.14 (3H, s), 2.08 (1H, m), 1.93-1.67 (10H, m). |

Example 47

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium bromide

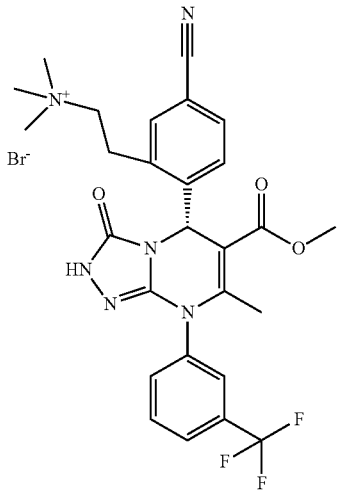

Intermediate 18

(R)-5-[2-(2-tert-Butoxy-vinyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

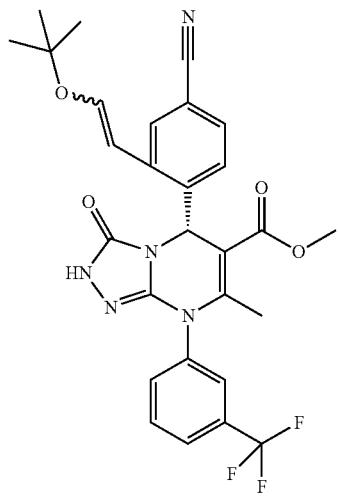 [SMILES: COC(=O)C1=C(C)N(c2cccc(C(F)(F)F)c2)c2n[nH]c(=O)n2[C@@H]1c1ccc(C#N)cc1C=COC(C)(C)C]

An autoclave was charged with a mixture of Intermediate 4b (10 g, 18.72 mmol), 2-methyl-2-vinyloxy-propane (6.55 g, 65.50 mmol), tri-tertiary-butyl phosphonium tetrafluoroborate (540 mg, 1.86 mmol), Herrmann-Beller catalyst (trans-di(μ-acetotao)bis(0-di-o-tolyl-phosphino)benzyl)dipalladium (II)) (880 mg, 0.94 mmol), 1,2,2,6,6-pentamethylpiperidine (11.5 g, 74.20 mmol). Tetra-ethylene glycol (140 mL) was added and the resulting solution degassed under Argon. The mixture was then heated at 150° C. for 1 hour. The mixture was cooled, diluted with EtOAc and aqueous 10% citric acid and the organic extract was washed with water and brine, then dried (Na$_2$SO$_4$) and concentrated in vacuo. The resultant residue was purified by chromatography, eluting with 25-75% EtOAc in cyclohexane to give the title compound as a [3:1] mixture of E/Z isomers and as a yellow foam (7.95 g).

LC-MS (Method 5): Rt=3.87 min, m/z=554.2 [M+H]$^+$

Intermediate 19

(R)-5-[4-Cyano-2-(2-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

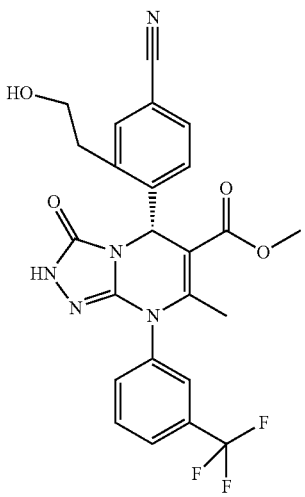 [SMILES: COC(=O)C1=C(C)N(c2cccc(C(F)(F)F)c2)c2n[nH]c(=O)n2[C@@H]1c1ccc(C#N)cc1CCO]

A solution of Intermediate 18 (7.87 g, 14.20 mmol) in DCM (130 mL) was cooled to −10° C. using a salt/ice bath and treated drop-wise with TFA (6.35 mL, 85.47 mmol). After stirring the solution at −10° C. for 2 hours, the resulting solution was poured into ice-cold aqueous Na$_2$CO$_3$ solution. The organic phase was separated and the aqueous phase was further extracted with DCM (70 mL) and the combined DCM extract returned to the salt/ice bath at −5° C. Sodium borohydride (1.57 g, 41.42 mmol) was added portion-wise and after stirring for 15 minutes, MeOH (32 mL) was added to the resulting mixture. The reaction was stirred at −5° C. for 1.5 hours, water was added and the resulting mixture allowed to stir vigorously for 15 minutes prior to separation of the organic phase. The aqueous phase was further extracted with DCM and the combined organic extract was washed with brine, dried (Na$_2$SO$_4$) and concentrated in vacuo. The resultant residue was purified by chromatography, eluting with EtOAc and gave the title compound as a cream solid (3.7 g).

LC-MS (Method 5): Rt=3.17 min, m/z=500.1 [M+H]$^+$

Alternative Synthesis of Intermediate 19

Intermediate 20

(R)-5-(4-Cyano-2-methoxycarbonylmethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

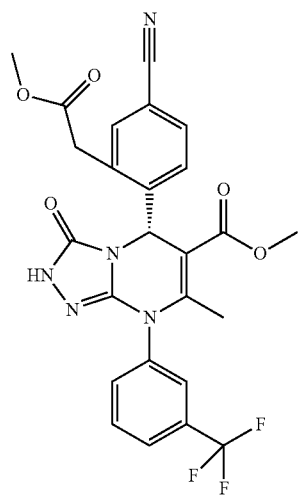

A microwave vial was charged with Intermediate 4b (2.5 g, 4.67 mmol), palladium(0)bis(dibenzylideneacetone) (132 mg, 0.23 mmol), zinc fluoride (242 mg, 2.34 mmol) and dry DMF (12 mL), then degassed under an argon atmosphere. A solution of tri(tert-butyl)phosphine (1 M in toluene; 475 μL, 0.19 mmol) and 1-(tert-butyldimethylsilyloxy)-1-methoxyethene (3.05 mL, 14 mmol) were added to the reaction, followed by further degassing. The mixture was heated under microwave irradiation at 135° C. for 4 hours. Further 1-(tert-butyldimethylsilyloxy)-1-methoxyethene (0.7 mL, 3.2 mmol) was added and the mixture heated under microwave irradiation for a further 1 hour at 135° C. The resultant mixture was partitioned between EtOAc and water, and the aqueous layer was extracted with EtOAc. The combined organic extract was washed with brine, dried (MgSO$_4$) and then concentrated in vacuo. The resultant residue was dissolved in MeOH, treated with TFA (5 drops) and allowed to stir for 18 h at RT (this process removes the TBDMS group from the initially generated silylated product). The reaction mixture was concentrated in vacuo and then purified by chromatography, eluting with 0-100% EtOAc in cyclohexane, to afford the title compound as a white solid (1.82 g).

LC-MS (Method 4): Rt=3.45 min, m/z=528.3 [M+H]$^+$ (R)-5-[4-Cyano-2-(2-hydroxy-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester (Intermediate 19)

A solution of Intermediate 20 (458 mg, 0.87 mmol) in anhydrous THF (5 mL) under argon was cooled to 0° C. in an ice-bath. A solution of lithium borohydride (1 M in THF; 1.04 mL, 1.04 mmol) was added drop-wise. The resulting solution was stirred at 0° C. for 3 h, then at RT for 18 hours. The reaction was quenched with water and diluted with EtOAc. The aqueous layer was further extracted with EtOAc. The combined organic extract was washed with brine, dried (MgSO$_4$), and purified by chromatography, eluting with 0-5% MeOH in DCM, to afford the title compound as a white solid (115 mg).

Intermediate 21

(R)-5-[2-(2-Bromo-ethyl)-4-cyano-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

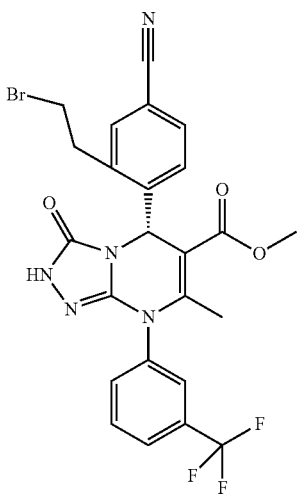 [SMILES: COC(=O)C1=C(C)N(c2cccc(C(F)(F)F)c2)c2n[nH]c(=O)n2[C@@H]1c1ccc(C#N)cc1CCBr]

The title compound was prepared from Intermediate 19 (0.30 g, 0.60 mmol) using an analogous method to that used for Intermediate 13 and gave the desired compound as a white solid (0.24 g).

LC-MS (Method 4): Rt=3.83 min, m/z=562.1 [M($^{79}$Br)+H]$^+$ (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium bromide (Example 47)

A cooled solution (ice bath) of Intermediate 21 (400 mg, 0.71 mmol) in MeCN (10 mL) was treated drop-wise with a solution of trimethylamine in EtOH (50 wt %) and the resulting solution allowed to stir at RT for 18 hours. The mixture was concentrated in vacuo then triturated with Et$_2$O and following sonication, a solid was collected and dried in vacuo at 35° C. for 2 hours. The solid product was partitioned between water (10 mL) and EtOAc (10 mL) and the aqueous layer separated and freeze dried to give the title compound as a white electrostatic solid.

LC-MS (Method 3) Rt=3.46 min, m/z=541.2 [M]$^+$ $^1$H NMR (400 MHz, DMSO) δ 11.30 (1H, bs), 8.13 (1H, bs), 7.97-7.87 (2H, m), 7.86-7.79 (2H, m), 7.78-7.67 (2H, m), 6.27 (1H, s), 4.03-3.93 (1H, m), 3.79-3.62 (2H, m) 3.53 (3H, s), 3.43-3.34 (1H, m, obscured), 3.21 (9H, s), 2.17 (3H, s).

Example 48

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium bromide

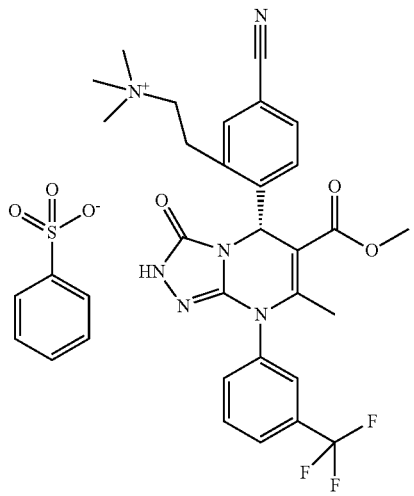

Intermediate 22

(R)-5-(4-Cyano-2-trimethylsilanylethynyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

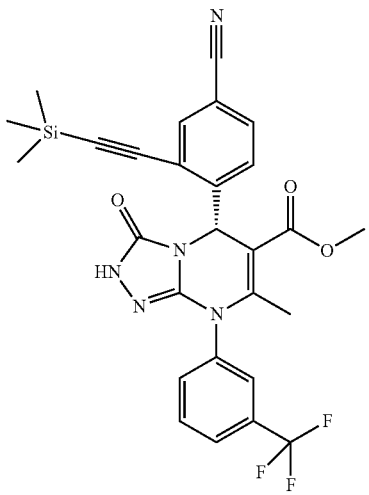

A microwave vial was charged with a mixture of Intermediate 4b (3.5 g, 6.57 mmol), ethynyl-trimethyl-silane (3.70 mL, 26.28 mmol), bis(triphenylphosphine) palladium(II) dichloride (461 mg, 0.66 mmol), copper(II)iodide (136 mg, 0.72 mmol) and DIPEA (3.40 mL, 19.71 mmol). Dioxane (16 mL) was added and the resulting solution degassed under Argon. The mixture was then heated at 130° C. for 1.25 hours. The reaction was cooled, diluted with water and the mixture was extracted with EtOAc (×3) and the combined organic extract was washed with brine, then dried (MgSO$_4$), filtered and concentrated in vacuo. The resultant residue was purified by chromatography, eluting with 0-60% EtOAc in cyclohexane to give the title compound as a cream coloured foam (5.65 g).

LC-MS (Method 2): Rt=4.18 min, m/z=552.3 [M+H]$^+$

Intermediate 23

(R)-5-(2-Bromoethynyl-4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

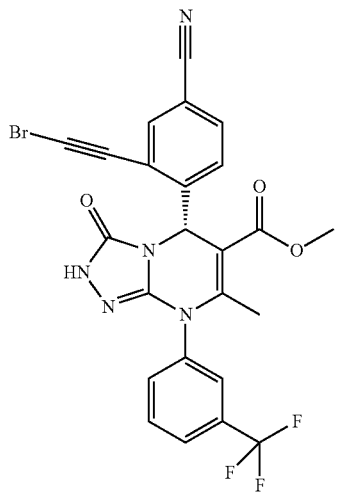 [SMILES: COC(=O)C1=C(C)N(c2cccc(C(F)(F)F)c2)c2n[nH]c(=O)n2[C@@H]1c1ccc(C#N)cc1C#CBr]

A cooled (ice bath) stirred solution of Intermediate 22 (2.14 g, 3.88 mmol) in acetone (40 mL) was treated with silver nitrate (66 mg, 0.39 mmol) followed by NBS (829 mg, 4.66 mmol). The cooling bath was removed after 1 hour and after a further 1 hour the mixture was diluted EtOAc and poured into water. The aqueous layer was separated and further extracted with EtOAc (×3) and the combined organic extract was washed with brine, dried (MgSO$_4$), filtered and concentrated in vacuo. The resultant residue was purified by chromatography, eluting with 0-100% EtOAc in cyclohexane to give the title compound as a pale yellow foam (1 g).

LC-MS (Method 5): Rt=3.63 min, m/z=558.1 [M($^{79}$Br)+H]$^+$

Intermediate 24

(R)-5-[4-Cyano-2-(2-dimethylamino-ethyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

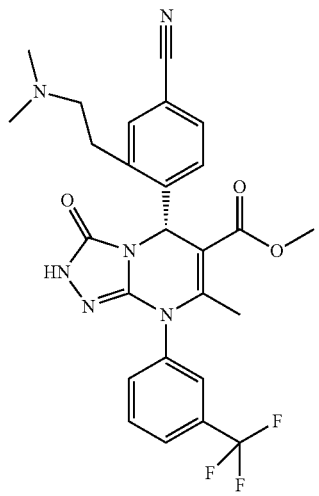

A solution of Intermediate 23 (210 mg, 0.38 mmol) in MeCN (0.40 mL) was treated with a solution of dimethylamine (2 M in THF; 1.90 mL, 3.80 mmol) and the resulting mixture stirred for 18 hours. The reaction mixture was cooled to 0° C. and MeOH (3 mL) was added, followed by sodium borohydride (71 mg, 1.88 mmol). After stirring for 1 hour the resultant mixture was poured into EtOAc and then washed with brine, dried (MgSO$_4$), filtered and concentrated in vacuo. The resultant residue was purified by chromatography, eluting with 2-8% (2M NH$_3$ in MeOH) in DCM to give the title compound as clear oil.

LC-MS (Method 4): Rt=3.52 min, m/z=527.2 [M+H]$^+$

Intermediate 25

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium iodide

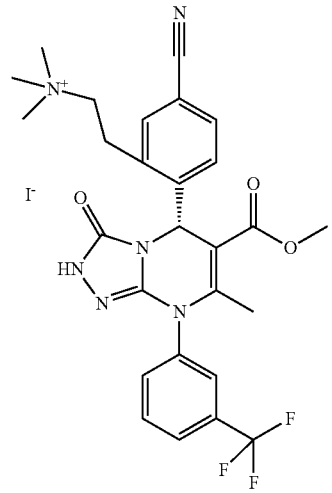

To a solution of Intermediate 24 (0.59 g, 1.12 mmol) in MeCN (10 mL) was added methyl iodide (0.25 mL, 4.0 mmol). The resultant mixture was warmed to 50° C. and stirred for 1.5 hours. The solvent was evaporated in vacuo to yield the title compound as a pale orange solid (0.68 g).

LC-MS (Method 1): Rt=2.39 min, m/z=541.3 [M]+

(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium benzenesulfonate (Example 48)

The title compound was prepared from Intermediate 25 (0.68 g, 1.02 mmol) using an analogous method to that used for Example 42 and gave the desired compound as a pale yellow electrostatic solid (0.72 g).

LC-MS (Method 3): Rt=3.45 min, m/z=541.2 [M]+

$^1$H NMR (400 MHz, DMSO) δ 11.30 (1H, bs), 8.13 (1H, bs), 7.97-7.87 (2H, m), 7.86-7.79 (2H, m), 7.78-7.67 (2H, m), 7.62-6.56 (2H, m. besylate), 7.35-7.28 (3H, m, besylate), 6.27 (1H, s), 4.03-3.93 (1H, m), 3.79-3.62 (2H, m), 3.53 (3H, s), 3.46-3.34 (1H, m, obscured), 3.21 (9H, s), 2.17 (3H, s).

Example 49

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium bromide

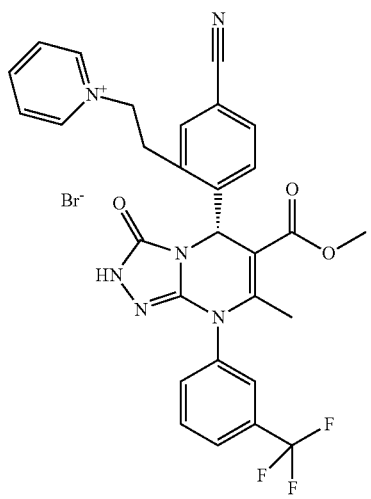 [SMILES: COC(=O)C1=C(C)N(c2cccc(C(F)(F)F)c2)c2n[nH]c(=O)n2[C@@H]1c1ccc(C#N)cc1CC[n+]1ccccc1 ; [Br-]]

A mixture of Intermediate 21 (0.40 g, 0.71 mmol) and pyridine was warmed to 50° C. for 3 hours then concentrated in vacuo. The crude product was partitioned between water and EtOAc and the aqueous layer separated and freeze dried to give the title compound as a white electrostatic solid (0.39 g).

LC-MS (Method 3): Rt=3.48 min, m/z=561.2 [M]+

$^1$H NMR (400 MHz, DMSO) δ 11.38 (1H, bs), 9.10 (2H, d, J=5.6 Hz), 8.67 (1H, t, J=7.7 Hz), 8.23 (2H, t, J=7.2 Hz), 8.15 (1H, bs), 7.97-7.87 (2H, m), 7.86-7.80 (1H, m), 7.79-7.70 (2H, m), 7.61 (1H, m), 6.43 (1H, s), 5.26-5.07 (2H, m), 3.97-3.84 (1H, m), 3.65-3.52 (1H, m), 3.49 (3H, s), 2.16 (3H, s).

Example 50

1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridininium formate

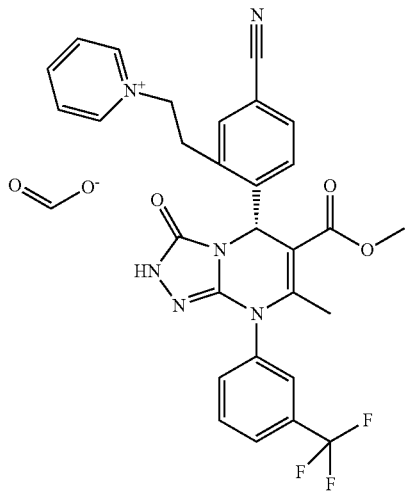

A solution of Intermediate 21 (100 mg, 0.18 mmol) in a mixture of MeCN (2.5 mL) and pyridine (0.15 mL, 1.78 mmol) was warmed to 70° C. for 18 hours in a sealed vial. The resultant solution was concentrated in vacuo and the crude product was purified directly by DMAP to give the title compound as a white electrostatic solid (54 mg).

LC-MS (Method 3): Rt=3.52 min, m/z=561.2 [M]+

$^1$H NMR (400 MHz, DMSO) δ 11.67 (1H, bs), 9.11 (2H, d, J=5.7 Hz), 8.67 (1H, t, J=7.8 Hz), 8.46 (1.4H, bs, formate), 8.23 (2H, t, J=7.2 Hz), 8.15 (1H, bs), 7.97-7.87 (2H, m), 7.86-7.80 (1H, m), 7.79-7.69 (2H, m), 7.61 (1H, m), 6.43 (1H, s), 5.27-5.09 (2H, m), 3.97-3.85 (1H, m), 3.65-3.52 (1H, m), 3.49 (3H, s), 2.16 (3H, s).

Example 51

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium bromide

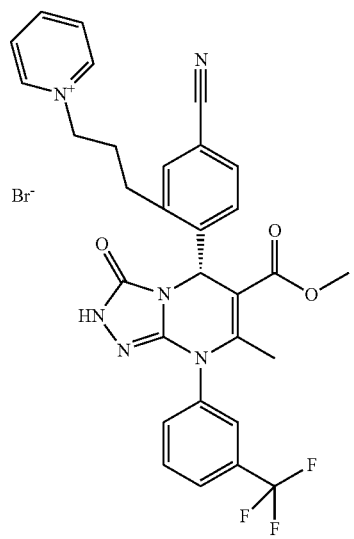 [SMILES: COC(=O)C1=C(C)N(c2cccc(C(F)(F)F)c2)c2n[nH]c(=O)n2[C@@H]1c1ccc(C#N)cc1CCC[n+]1ccccc1 ; [Br-]]

The title compound was prepared from Intermediate 13 (0.68 g, 1.02 mmol) and pyridine using an analogous method to that used for Example 19 and gave the desired compound as a pale yellow electrostatic solid (0.72 g).

LC-MS (Method 3): Rt=3.53 min, m/z=575.22 [M]⁺

¹H NMR (400 MHz, DMSO) δ 11.18 (1H, bs), 9.18 (2H, d, J=6.6 Hz), 8.64 (1H, t, J=7.8 Hz), 8.21 (2H, t, J=7.2 Hz), 8.12 (1H, bs), 7.96-7.86 (2H, m), 7.86-7.80 (1H, m), 7.76-7.72 (1H, m), 7.72-7.60 (2H, m), 6.12 (1H, s), 4.79 (2H, t, J=7.5 Hz), 3.50 (3H, s), 3.35-3.24 (1H, m, obscured), 3.12-2.99 (1H, m), 2.65-2.53 (1H, m), 2.51-2.40 (1H, m, obscured), 2.14 (3H, s).

Example 52

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium formate

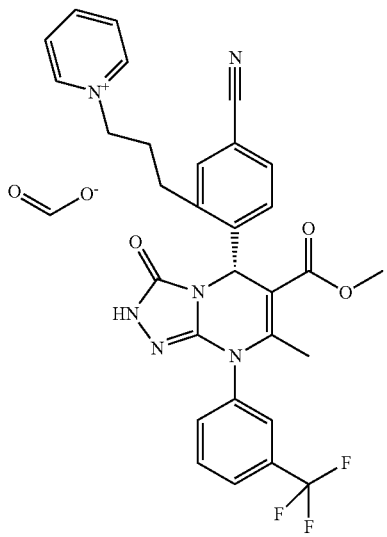

The title compound was prepared from Example 51 (91 mg, 0.14 mmol) following MDAP purification and gave the title compound as a white electrostatic solid (59 mg).

LC-MS (Method 3): Rt=3.52 min, m/z=575.22 [M]⁺

¹H NMR (400 MHz, DMSO) δ 11.50 (1H, bs), 9.20 (2H, d, J=5.7 Hz), 8.64 (1H, t, J=7.8 Hz), 8.46 (1.4H, bs, formate), 8.21 (2H, t, J=6.8 Hz), 8.12 (1H, bs), 7.96-7.87 (2H, m), 7.86-7.79 (1H, m), 7.76-7.72 (1H, m), 7.72-7.61 (2H, m), 6.12 (1H, s), 4.80 (2H, t, J =7.4 Hz), 3.49 (3H, s), 3.37-3.24 (1H, m, obscured), 3.12-2.99 (1H, m), 2.65-2.53 (1H, m), 2.51-2.40 (1H, m, obscured), 2.14 (3H, s).

Example 53

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium benzenesulfonate.

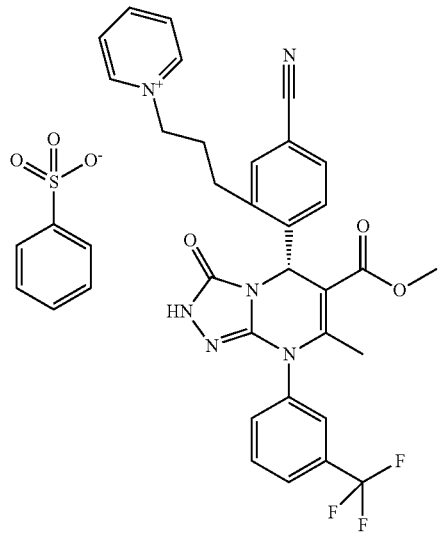 [SMILES: O=S(=O)([O-])c1ccccc1 ; COC(=O)C1=C(C)N(c2cccc(C(F)(F)F)c2)c2n[nH]c(=O)n2[C@@H]1c1ccc(C#N)cc1CCC[n+]1ccccc1]

The title compound was prepared from Example 51 (0.51 g, 0.78 mmol) using an analogous method to that used for Example 42 and gave the desired compound as a pale yellow electrostatic solid (0.55 g).

LC-MS (Method 3): Rt=3.50 min, m/z=575.2 [M]⁺

¹H NMR (400 MHz, DMSO) δ 11.23 (1H, bs), 9.18 (2H, d, J=6.5 Hz), 8.64 (1H, t, J=7.7 Hz), 8.21 (2H, t, J=7.4 Hz), 8.12 (1H, bs), 7.95-7.88 (2H, m), 7.86-7.78 (1H, m), 7.76-7.72 (1H, m), 7.72-7.61 (2H, m), 7.61-7.57 (2H, m, besylate), 7.35-7.27 (3H, m, besylate), 6.12 (1H, s), 4.80 (2H, t, J=7.4 Hz), 3.49 (3H, s), 3.37-3.24 (1H, m, obscured), 3.12-2.99 (1H, m), 2.65-2.53 (1H, m), 2.51-2.40 (1H, m, obscured), 2.14 (3H, s).

Example 54

1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium chloride

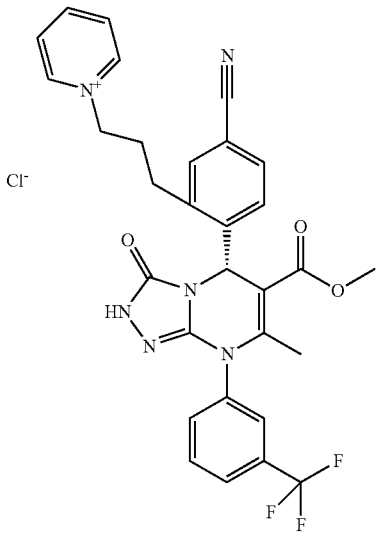 [SMILES: [Cl-] ; COC(=O)C1=C(C)N(c2cccc(C(F)(F)F)c2)c2n[nH]c(=O)n2[C@@H]1c1ccc(C#N)cc1CCC[n+]1ccccc1]

The title compound was prepared from Example 53 (0.51 g, 0.70 mmol) using Amberlite IRA 458 'chloride' resin (40 g, wet) and an analogous method to that used for Example 42 and gave the desired compound as a white electrostatic solid (0.44 g).

LC-MS (Method 3): Rt=3.50 min, m/z=575.2 [M]$^+$ $^1$H NMR (400 MHz, DMSO) δ 11.25 (1H, bs), 9.19 (2H, d, J=6.7 Hz), 8.64 (1H, t, J=7.8 Hz), 8.21 (2H, t, J=7.0 Hz), 8.12 (1H, bs), 7.95-7.88 (2H, m), 7.86-7.78 (1H, m), 7.76-7.72 (1H, m), 7.71-7.61 (2H, m), 6.12 (1H, s), 4.80 (2H, t, J=7.4 Hz), 3.49 (3H, s), 3.36-3.23 (1H, m, obscured), 3.12-2.99 (1H, m), 2.65-2.53 (1H, m), 2.51-2.40 (1H, m, obscured), 2.14 (3H, s).

The following compounds were prepared from Example 51 using an analogous method to that used for Example 42, utilising an appropriate acid to prepare the desired IRA-458 resin, and gave the desired compounds as white electrostatic solids.

| Example | Structure | Name | LC-MS (Method 3) | NMR |
|---|---|---|---|---|
| 55 | 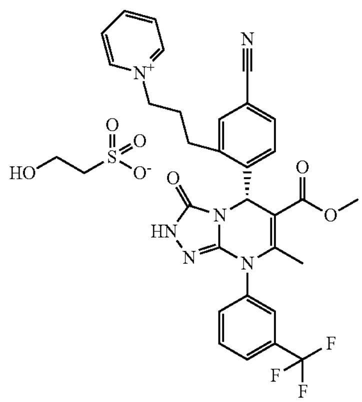 [SMILES: O=S(=O)([O-])CCO ; COC(=O)C1=C(C)N(c2cccc(C(F)(F)F)c2)c2n[nH]c(=O)n2[C@@H]1c1ccc(C#N)cc1CCC[n+]1ccccc1] | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium 2-hydroxy-ethanesulfonate | Rt = 3.53 min, m/z = 575.2 [M]$^+$ | $^1$H NMR (400 MHz, DMSO) δ 11.20 (1H, bs), 9.18 (2H, d, J = 6.6 Hz), 8.64 (1H, t, J = 7.9 Hz), 8.20 (2H, t, J = 7.1 Hz), 8.12 (1H, bs), 7.95-7.88 (2H, m), 7.86-7.78 (1H, m), 7.76-7.72 (1H, m), 7.72-7.60 (2H, m), 6.12 (1H, s), 4.78 (2H, t, J = 7.4 Hz), 4.45 (1H, t, J = 5.8 Hz, isethionate), 3.62 (2H, q, J = 6.5 Hz, isethionate), 3.49 (3H, s), 3.37-3.24 (1H, m, obscured), 3.12-2.99 (1H, m), 2.63-2.53 (1H, m, obscured), 2.60 (1H, t, J = 6.7 Hz, isethionate), 2.53-2.40 (1H, m, obscured), 2.14 (3H, s). |
| 56 | 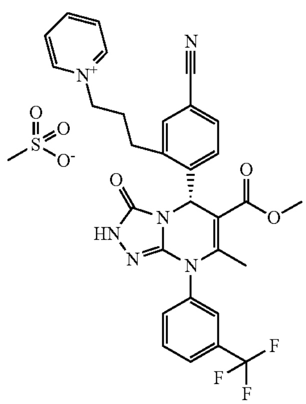 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium methanesulfonate | Rt = 3.52 min, m/z = 575.2 [M]$^+$ | $^1$H NMR (400 MHz, DMSO) δ 11.24 (1H, bs), 9.18 (2H, d, J = 6.7 Hz), 8.64 (1H, t, J = 7.9 Hz), 8.21 (2H, t, J = 7.2 Hz), 8.12 (1H, bs), 7.96-7.87 (2H, m), 7.86-7.78 (1H, m), 7.76-7.73 (1H, m), 7.72-7.60 (2H, m), 6.12 (1H, s), 4.79 (2H, t, J = 7.4 Hz), 3.49 (3H, s), 3.36-3.25 (1H, m, obscured), 3.12-3.00 (1H, m), 2.63-2.54 (1H, m), 2.53-2.42 (1H, m, obscured), 2.30 (3H, s), 2.14 (3H, s). |
| 57 | 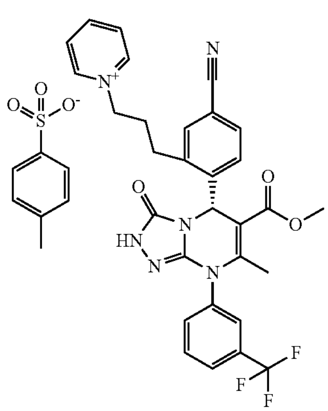 [SMILES: Cc1ccc(S(=O)(=O)[O-])cc1 ; COC(=O)C1=C(C)N(c2cccc(C(F)(F)F)c2)c2n[nH]c(=O)n2[C@@H]1c1ccc(C#N)cc1CCC[n+]1ccccc1] | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-hydroxymethyl-pyridinium tosylate | Rt = 3.49 min, m/z = 575.2 [M]$^+$ | $^1$H NMR (400 MHz, DMSO) δ 11.24 (1H, bs), 9.18 (2H, d, J = 6.2 Hz), 8.64 (1H, t, J = 7.9 Hz), 8.21 (2H, t, J = 7.4 Hz), 8.12 (1H, bs), 7.95-7.88 (2H, m), 7.85-7.78 (1H, m), 7.76-7.72 (1H, m), 7.72-7.61 (2H, m), 7.50-7.45 (2H, m, tosylate), 7.13-7.08 (2H, m, tosylate), 6.12 (1H, s), 4.79 (2H, t, J = 7.5 Hz), 3.49 (3H, s), 3.37-3.25 (1H, m, obscured), 3.12-2.99 (1H, m), 2.66-2.53 (1H, m), 2.51-2.40 (1H, m, obscured), 2.28 (3H, s), 2.14 (3H, s). |

The following examples were prepared from Intermediate 13 and the appropriately substituted pyridines using an analogous method to Example 19.

| Example | Structure | Name | LC-MS (Method 3) | NMR |
|---|---|---|---|---|
| 58 | 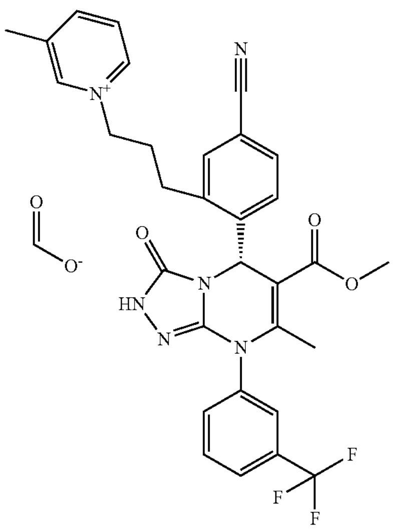 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-methyl-pyridinium formate | Rt = 3.61 min, m/z = 589.2 [M]$^+$ | $^1$H NMR (400 MHz, DMSO) δ 11.46 (1H, bs), 9.09 (1H, s), 9.01 (1H, d, J = 5.9 Hz), 8.49 (1.3H, bs, formate), 8.46 (1H, s), 8.12 (1H, bs), 8.12-8.05 (1H, m), 7.97-7.87 (2H, m), 7.85-7.79 (1H, m), 7.74-7.71 (1H, m), 7.71-7.60 (2H, m), 6.11 (1H, s), 4.73 (2H, t, J = 7.3 Hz), 3.49 (3H, s), 3.37-3.25 (1H, m, obscured), 3.11-2.99 (1H, m), 2.64-2.52 (1H, m, obscured), 2.51 (3H, bs, obscured), 2.51-2.41 (1H, m, obscured), 2.14 (3H, s). |
| 59 | 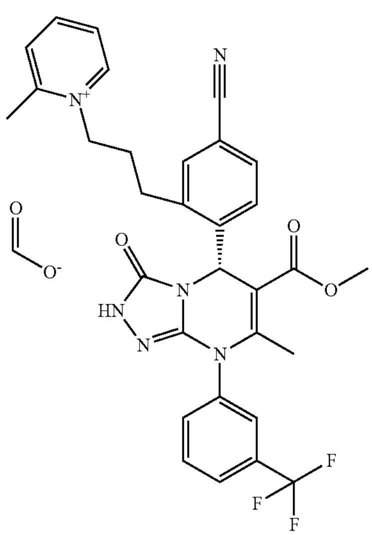 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-2-methyl-pyridinium formate | Rt = 3.59 min, m/z = 589.2 [M]$^+$ | $^1$H NMR (400 MHz, DMSO) δ 11.43 (1H, bs), 9.08 (1H, d, J = 6.1 Hz), 8.50 (1H, t, J = 7.7 Hz), 8.46 (1.4H, bs, formate), 8.12 (1H, bs), 8.08 (1H, d, J = 7.9 Hz), 8.04-7.98 (1H, m), 7.96-7.88 (2H, m), 7.85-7.77 (2H, m), 7.72-7.60 (2H, m), 6.17 (1H, s), 4.74 (2H, t, J = 7.7 Hz), 3.50 (3H, s), 3.40-3.28 (1H, m), 3.14-3.03 (1H, m), 2.92 (3H, s), 2.61-2.48 (1H, m, obscured), 2.43-2.28 (1H, m), 2.15 (3H, s). |

| Example | Structure | Name | LC-MS (Method 3) | NMR |
|---|---|---|---|---|
| 60 | 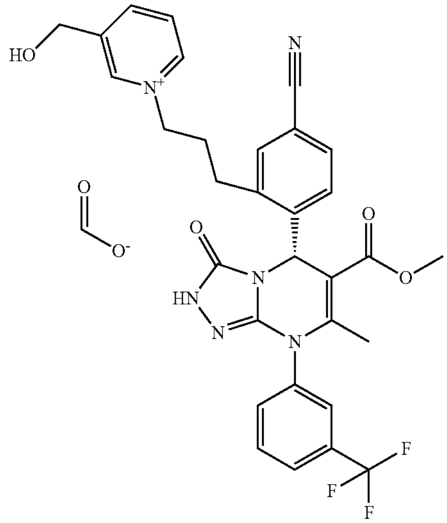 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-hydroxymethyl-pyridinium formate | Rt = 3.47 min, m/z = 605.2 [M]⁺ | $^1$H NMR (400 MHz, DMSO) δ 11.32 (1H, bs), 9.15 (1H, s), 9.06 (1H, d, J = 5.9 Hz), 8.53 (1H, t, J = 7.9 Hz), 8.46 (1.4H, bs, formate), 8.19-8.13 (1H, m), 8.12 (1H, bs), 7.95-7.87 (2H, m), 7.85-7.78 (1H, m), 7.75-7.72 (1H, m), 7.71-7.60 (2H, m), 6.12 (1H, s), 4.79 (2H, t, J = 7.3 Hz), 4.75 (2H, s), 3.49 (3H, s), 3.36-3.25 (1H, m), 3.12-2.99 (1H, m), 2.61-2.52 (1H, m), 2.49-2.39 (1H, m, obscured), 2.14 (3H, s). |
| 61 | 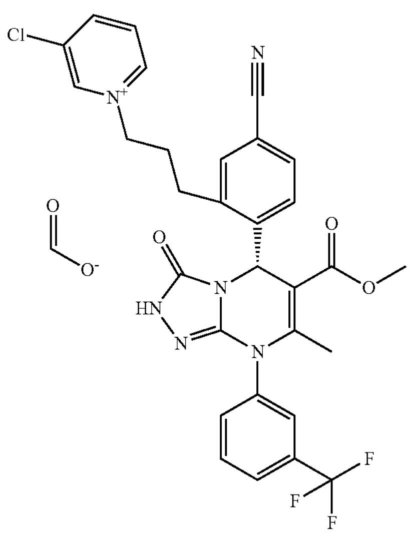 | 3-Chloro-1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium formate | Rt = 3.62 min, m/z = 609.2 [M]⁺ | $^1$H NMR (400 MHz, DMSO) δ 11.27 (1H, bs), 9.56 (1H, s), 9.25-9.14 (1H, m), 8.81 (1H, d, J = 7.6 Hz), 8.43 (1.5H, bs, formate), 8.28-8.20 (1H m), 8.12 (1H, bs), 7.96-7.88 (2H, m), 7.86-7.78 (1H, m), 7.76-7.72 (1H, m), 7.71-7.61 (2H, m). 6.13 (1H, s), 4.79 (2H, t, J = 7.1 Hz), 3.51 (3H, s), 3.38-3.27 (1H, m), 3.13-3.01 (1H, m), 2.65-2.54 (1H, m), 2.53-2.45 (1H, m, obscured), 2.15 (3H, s). |

The following examples were prepared from Intermediate 23 and the appropriately substituted secondary amines using analogous methods to those used for Intermediate 24 and Intermediate 25, respectively. Following purification by MDAP and lyophilisation, the title compounds were obtained as white electrostatic solids.

| Example | Structure | Name | LC-MS (Method 3) | NMR |
|---|---|---|---|---|
| 62 | 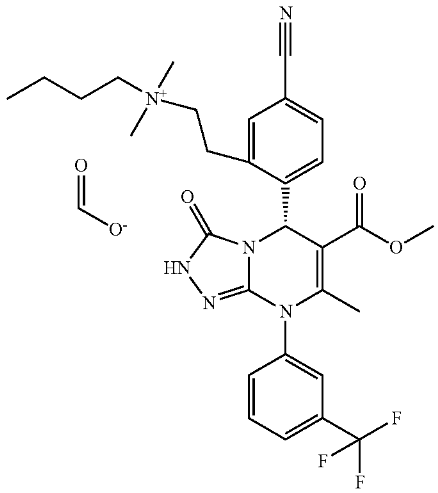 | Butyl-(3-{5-cyano-2-[(R)-6-methoxy-carbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-ammonium formate | Rt = 3.75 min, m/z = 583.3 [M]$^+$ | $^1$H NMR (400 MHz, DMSO) δ 11.55 (1H, bs), 8.53 (1H, s, formate), 8.14 (1H, s), 7.97-7.88 (2H, m), 7.87-7.80 (2H, m), 7.78-7.73 (1H, m), 7.73-7.67 (1H, m), 6.24 (1H, s), 4.04-3.95 (1H, m), 3.74-3.60 (2H, m), 3.54 (3H, s), 3.18 (6H, s), 3.44-3.29 (3H, m, obscured), 2.16 (3H, s), 1.82-1.71 (2H, m), 1.41-1.29 (2H, m), 0.96 (3H, t, J = 8 Hz). |
| 63 | 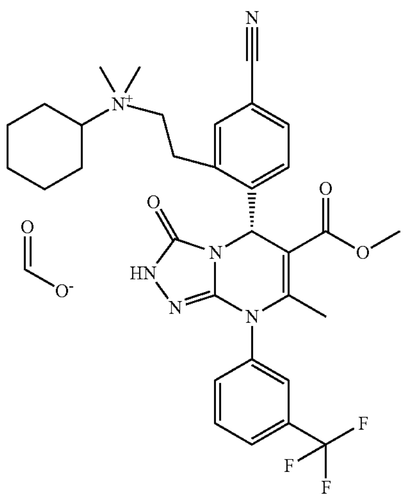 | (3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclohexyl-dimethyl-ammonium formate | Rt = 3.80 min, m/z = 609.4 [M]$^+$ | $^1$H NMR (400 MHz, DMSO) δ 11.52 (1H, bs), 8.43 (1.6H, s, formate), 8.14 (1H, s), 7.97-7.87 (3H, m), 7.87-7.79 (1H, m), 7.78-7.73 (1H, m), 7.73-7.66 (1H, m), 6.23 (1H, s), 4.08-3.97 (1H, m), 3.73-3.24 (4H, m, obscured), 3.54 (3H, s), 3.18-3.12 (6H, m), 2.28-2.18 (2H, m), 2.16 (3H, s), 1.94-1.83 (2H, m), 1.69-1.44 (3H, m), 1.43-1.22 (2H, m), 1.22-1.04 (1H, m). |
| 64 | 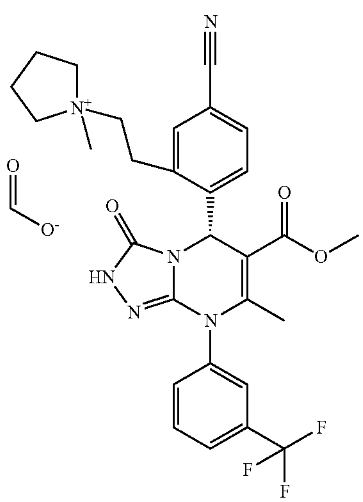 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-methyl-pyrrolidinium formate | Rt = 3.51 min, m/z = 567.3 [M]$^+$ | $^1$H NMR (400 MHz, DMSO) δ 11.32 (1H, very broad s), 8.44 (1.4H, s, formate), 8.13 (1H, bs), 7.97-7.86 (3H, m), 7.86-7.79 (1H, m), 7.79-7.67 (2H, m), 6.27 (1H, s), 4.07-3.95 (1H, m), 3.83-3.28 (7H, m, obscured), 3.53 (3H, s), 3.21 (3H, s), 2.22-2.12 (7H, m). |

-continued

| Example | Structure | Name | LC-MS (Method 3) | NMR |
|---|---|---|---|---|
| 65 | 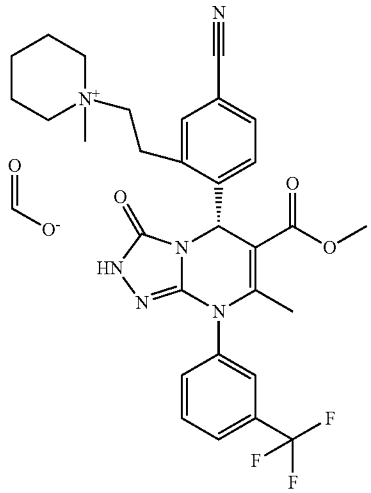 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-methyl-piperidinium formate | Rt = 3.59 min, m/z = 581.2 [M]+ | ¹H NMR (400 MHz, DMSO) δ 11.46 (1H, bs), 8.38 (1.7H, s, formate), 8.08 (1H, bs), 7.92-7.82 (3H, m), 7.82-7.74 (1H, m), 7.74-7.68 (1H, m), 7.68-7.62 (1H, m), 6.18 (1H, s), 4.17-4.05 (1H, m), 3.67-3.21 (7H, m, obscured), 3.49 (3H, s), 3.18 (3H, s), 2.11 (3H, s), 1.96-1.72 (4H, m), 1.58-1.48 (2H, m). |
| 66 | 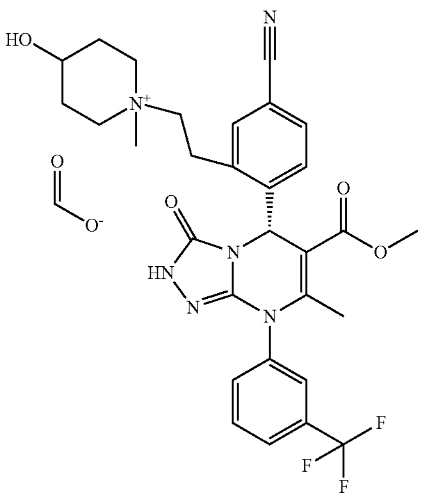 | 1-(3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-hydroxy-1-methyl-piperidinium formate | Rt = 3.44 min, m/z = 597.3 [M]+ | ¹H NMR (400 MHz, DMSO) δ 11.52 (1H, bs), 8.43 (1.4H, s, formate), 8.13 (1H, bs), 7.97-7.87 (3H, m), 7.87-7.79 (1H, m), 7.79-7.73 (1H, m), 7.73-7.66 (1H, m), 6.23 & 6.26 (1H total, 2s, isomers), 4.21-4.05 (1H, m), 3.93-3.17 (9H, m, obscured), 3.53 (3H, s), 3.27 & 3.22 (3H total, 2s, isomers), 2.16 (3H, s), 2.19-1.99 (2H, m), 1.89-1.69 (2H, m). |
| 67 | 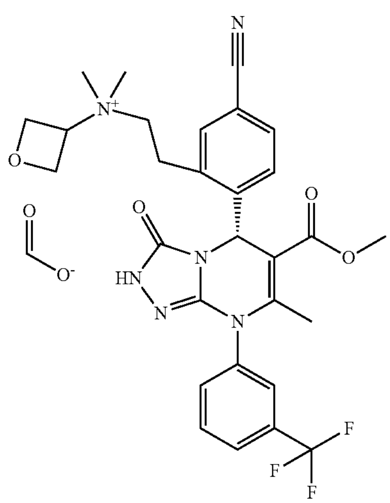 | (3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-oxetan-3-yl-ammonium formate | Rt = 3.44 min, m/z = 583.3 [M]+ | ¹H NMR (400 MHz, DMSO) δ 11.58 (1H, bs), 8.52 (1H, s, formate), 8.13 (1H, bs), 7.93 (2H, m), 7.86 (1H, d, J = 1.4 Hz), 7.83 (1H, t, J = 7.9 Hz), 7.76 (1H, dd, J = 1.6, 7.9 Hz), 7.70 (1H, d, J = 8.2 Hz), 6.26 (1H, s), 4.98 (2H, m), 4.92-4.83 (3H, m), 4.00 (1H, m), 3.73-3.58 (2H, m), 3.53 (3H, s), 3.39-3.31 (1H, obscured), 3.28 (3H, s), 3.27 (3H, s), 2.16 (3H, s). |

| Example | Structure | Name | LC-MS (Method 3) | NMR |
|---|---|---|---|---|
| 68 | 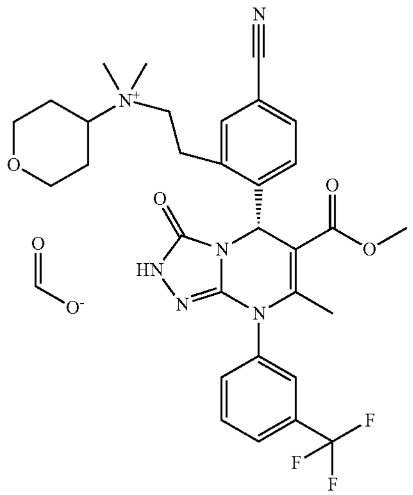 | (3-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-(tetrahydro-pyran-4-yl)-ammonium formate | Rt = 3.51 min, m/z = 611.3 [M]⁺ | ¹H NMR (400 MHz, DMSO) δ 11.54 (1H, bs), 8.41 (1.1H, s formate), 8.14 (1H, bs), 7.92 (3H, m), 7.83 (1H, t, J = 7.9 Hz), 7.76 (1H, dd, J = 1.6, 8.1 Hz), 7.70 (1H, d, J = 8.1 Hz), 6.25 (1H, s), 4.04 (3H, m), 3.80-3.59 (2H, m, obscured), 3.54 (3H, s), 3.43-3.28 (4H, m), 3.16 (3H, s), 3.15 (3H, s), 2.16 (3H, s), 2.11 (2H, m), 1.82 (2H, m). |
| 69 | 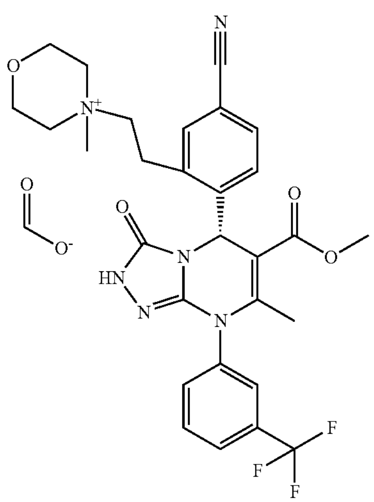 | 4-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-methyl-morpholin-4-ium formate | Rt = 3.47 min, m/z = 583.2 [M]⁺ | ¹H NMR (400 MHz, DMSO) δ 11.54 (1H, bs), 8.43 (1.5H, s, formate), 8.14 (1H, bs), 7.96-7.88 (3H, m), 7.87-7.80 (1H, m), 7.79-7.74 (1H, m), 7.74-7.68 (1H, m), 6.27 (1H, s), 4.34-4.21 (1H, m), 4.11-3.90 (4H, m), 3.83-3.27 (7H, m, obscured), 3.53 (3H, s), 3.35 (3H, s), 2.16 (3H, s). |

Intermediate 26

Dimethyl-(tetrahydro-pyran-4-ylmethyl)-amine

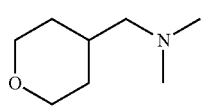

4-(Bromomethyl)tetrahydro-2H-pyran (0.50 g, 2.8 mmol) was dissolved in dimethylamine (40% in water, 5 mL) and the reaction mixture was stirred at RT for 18 hours. The mixture was saturated with NaCl and extracted into Et₂O (2×). The combined organic extract was dried (K₂CO₃), filtered and concentrated in vacuo to give the title compound as a colourless oil (0.40 g).

¹H NMR (400 MHz, CDCl₃) δ 3.97 (2H, dd, J=11.6, 4.4 Hz), 3.39 (2H, td, J=11.6, 1.6 Hz), 2.20 (6H, s), 2.12 (2H, d, J=6.5 Hz), 1.75-1.62 (3H, m), 1.33-1.21 (2H, m).

The following examples were prepared from Intermediate 21 and the appropriately substituted tertiary amines or basic heterocycles using an analogous method to that used in Example 50 (all tertiary amines were known or commercially available unless otherwise stated). Following purification by MDAP and lyophilisation, the title compounds were obtained as white electrostatic solids.

| Example | Structure | Name | LC-MS (Method 3) | NMR |
|---|---|---|---|---|
| 70 | 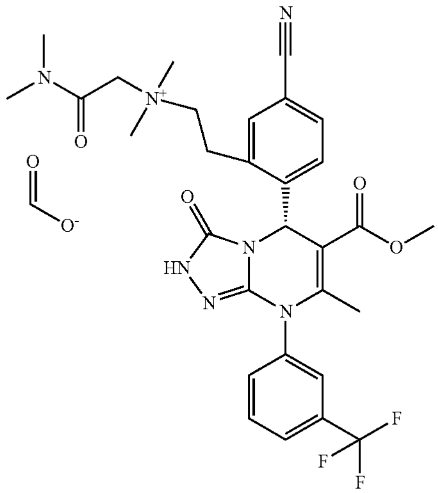 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethylcarbamoyl-methyl-dimethyl-ammonium formate | Rt = 3.52 min, m/z = 612.4 [M]+ | $^1$H NMR (400 MHz, DMSO) δ 11.46 (1H, bs), 8.40 (1.7H, s, formate), 8.14 (1H, bs), 7.93 (2H, m), 7.82 (2H, m), 7.77 (1H, m), 7.71 (1H, m), 6.24 (1H, s), 4.58 (2H, m), 4.17 (1H, m), 4.03 (1H, m), 3.67 (2H, m, obscured), 3.37 (9H, s), 2.99 (3H, s), 2.90 (3H, s), 2.17 (3H, s). |
| 71 | 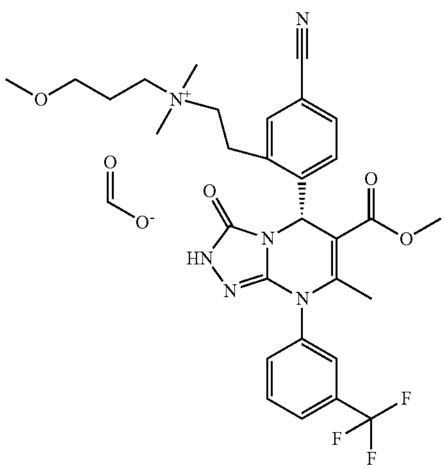 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(3-methoxy-propyl)-dimethyl-ammonium formate | Rt = 3.58 min, m/z = 599.4 [M]+ | $^1$H NMR (400 MHz, DMSO) δ 11.52 (1H, bs), 8.45 (1.5H, s, formate), 8.14 (1H, bs), 7.93 (2H, m), 7.88-7.79 (2H, m), 7.76 (1H, m), 7.70 (1H, m), 6.24 (1H, s), 4.03 (1H, m), 3.66 (2H, m), 3.53 (3H, s), 3.60-3.23 (5H, m, obscured) 3.27 (3H, s), 3.19 (6H, s), 2.16 (3H, s), 2.06 (2H, m). |
| 72 | 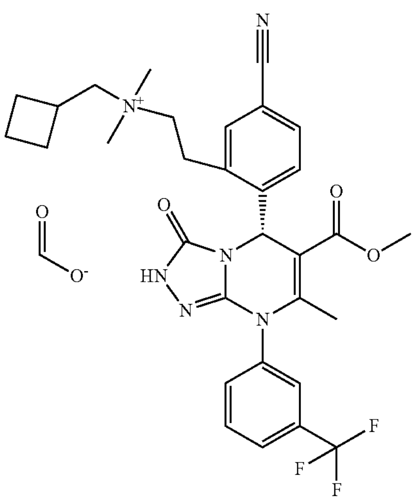 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclobutylmethyl-dimethyl-ammonium formate | Rt = 3.75 min, m/z = 595.3 [M]+ | $^1$H NMR (400 MHz, DMSO) δ 11.54 (1H, bs), 8.42 (1.5H, bs, formate), 8.14 (1H, bs), 7.97-7.87 (2H, m), 7.87-7.79 (2H, m), 7.79-7.74 (1H, m), 7.74-7.67 (1H, m), 6.25 (1H, s), 4.00-3.91 (1H, m), 3.71-3.60 (2H, m, obscured), 3.51-3.42 (2H, m, obscured), 3.53 (3H, s, obscured), 3.38-3.27 (1H, m), 3.13 (3H, s), 3.12 (3H, s), 3.02-2.90 (1H, m), 2.17 (3H, s), 2.08-2.19 (2H, m), 1.98-1.74 (4H, m). |

| Example | Structure | Name | LC-MS (Method 3) | NMR |
|---|---|---|---|---|
| 73* | 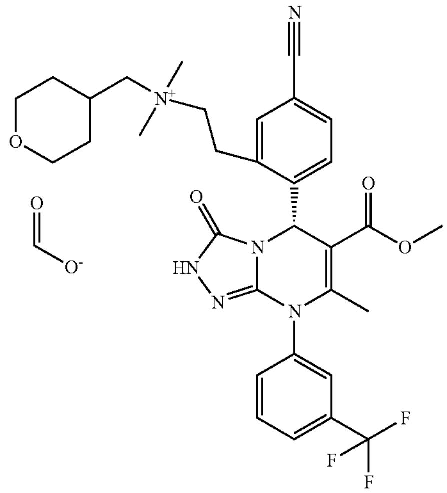 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-(tetrahydro-pyran-4-ylmethyl)-ammonium formate | Rt = 3.55 min, m/z = 625.4 [M]⁺ | ¹H NMR (400 MHz, DMSO) δ 11.58 (1H, bs), 8.46 (1.4H, s, formate), 8.13 (1H, bs), 7.93 (2H, m), 7.83 (2H, m), 7.76 (1H, dd, J = 8.1, 1.6 Hz), 7.70 (1H, d, J = 8.1 Hz), 6.24 (1H, s), 4.08 (1H, m), 3.83 (2H, m), 3.72-3.32 (10H, m, obscured), 3.22 (6H, s), 2.32 (1H, m), 2.16 (3H, s), 1.75 (2H, m), 1.38 (2H, m). |
| 74 | 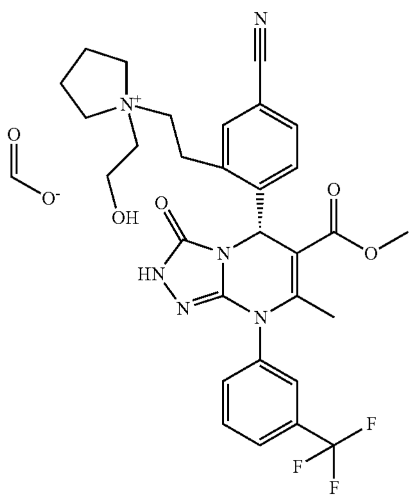 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-(2-hydroxy-ethyl)-pyrrolidinium formate | Rt = 3.48 min, m/z = 597.3 [M]⁺ | ¹H NMR (400 MHz, DMSO) δ 11.56 (1H, bs), 8.46 (1.4H, s, formate), 8.13 (1H, bs), 7.92 (2H, m), 7.86 (1H, d, J = 1.5 Hz), 7.83 (1H, t, J = 7.9 Hz), 7.75 (1H, dd, J = 8.1, 1.5 Hz), 7.69 (1H, d, J = 8.1 Hz), 6.27 (1H, s), 4.08-3.92 (4H, m), 3.80-3.35 (11H, m, obscured) 2.16 (3H, s), 2.13 (4H, m). |
| 75 | 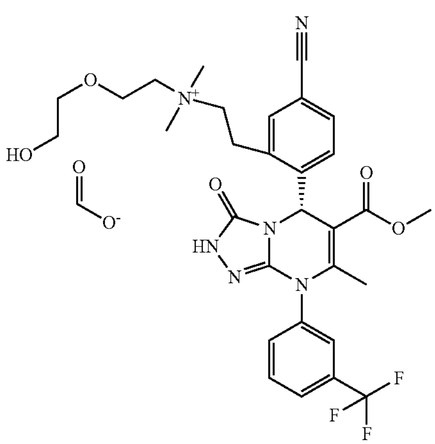 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-[2-(2-hydroxy-ethoxy)-ethyl]-dimethyl-ammonium formate | Rt = 3.39 min, m/z = 615.3 [M]⁺ | ¹H NMR (400 MHz, DMSO) δ 11.55 (1H, bs), 8.49 (1H, s, formate), 8.14 (1H, s), 7.97-7.87 (2H, m), 7.88-7.79 (2H, m), 7.79-7.73 (1H, m), 7.73-7.66 (1H, m), 6.26 (1H, s), 4.11-3.99 (1H, m), 3.94 (2H, s), 3.82-3.61 (4H, m), 3.59-3.30, (9H, m, obscured), 3.34 (6H, s), 2.17 (3H, s). |

| Example | Structure | Name | LC-MS (Method 3) | NMR |
|---|---|---|---|---|
| 76 | 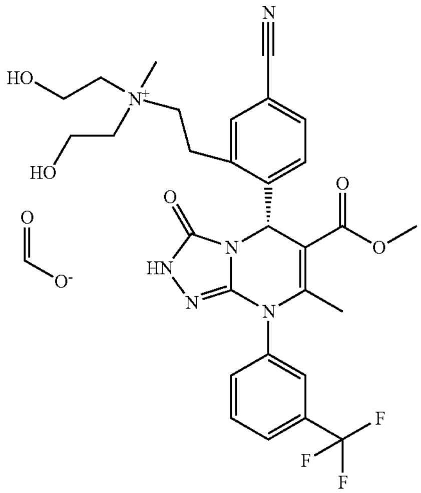 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-bis-(2-hydroxy-ethyl)-methyl-ammonium formate | Rt = 3.37 min, m/z = 601.3 [M]+ | ¹H NMR (400 MHz, DMSO) δ 11.45 (1H, bs), 8.50 (1H, s, formate), 8.15 (1H, s), 7.98-7.89 (2H, m), 7.89-7.80 (2H, m), 7.79-7.74 (1H, m), 7.74-7.68 (1H, m), 6.28 (1H, s), 4.18-4.06 (1H, m), 3.96 (4H, s), 3.84-3.73 (1H, m), 3.73-3.58 (4H, m), 3.54 (3H, s), 3.28 (3H, s), 2.17 (3H, s). 2 xOH's not observed. |
| 77 | 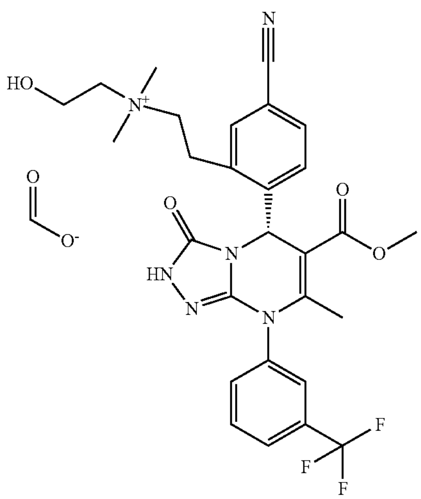 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(2-hydroxy-ethyl)-dimethyl-ammonium forma | Rt = 3.42 min, m/z = 571.3 [M]+ | NMR (400 MHz, DMSO) δ 11.54 (1H, bs), 8.52 (1.1H, s, formate), 8.14 (1H, bs), 7.97-7.87 (2H, m), 7.87-7.79 (2H, m), 7.79-7.73 (1H, m), 7.73-7.67 (1H, m), 6.27 (1H, s), 4.09-3.99 (1H, m), 3.94 (2H, bs), 3.81-3.62 (2H, m), 3.61-3.51 (2H, m), 3.53 (3H, s), 3.44-3.34 (assumed 2H, m, obscured) 3.24 (6H, s), 2.16 (3H, s). |
| 78 | 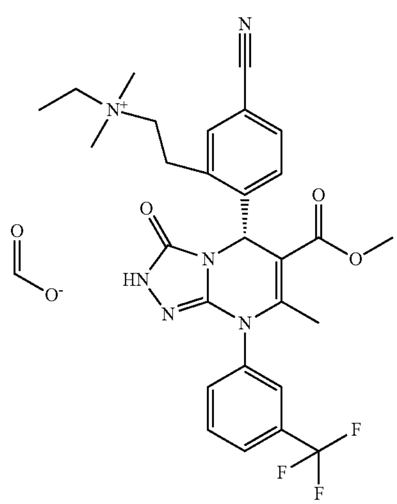 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-ethyl-dimethyl-ammonium format | Rt = 3.49 min, m/z = 555.3 [M]+ | ¹H NMR (400 MHz, DMSO) δ 11.51 (1H, bs), 8.43 (1.3H, s, formate), 8.13 (1H, bs), 7.96-7.88 (2H, m), 7.88-7.79 (2H, m), 7.79-7.73 (1H, m), 7.73-7.67 (1H, m), 6.25 (1H, s), 4.04-3.94 (1H, m), 3.73-3.27 (5H, m, obscured), 3.53 (3H, s), 3.16 (6H, s), 2.16 (3H, s), 1.34 (3H, t, J = 7 Hz). |

-continued

| Example | Structure | Name | LC-MS (Method 3) | NMR |
|---|---|---|---|---|
| 79 | 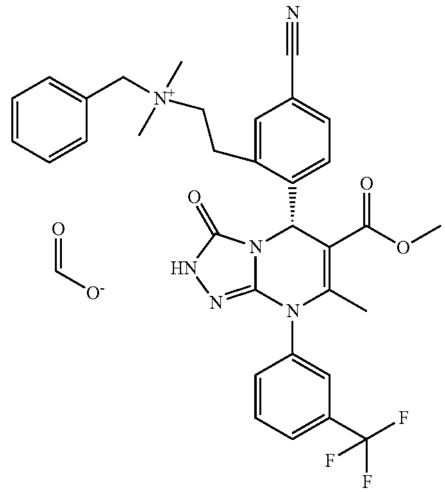 | Benzyl-(2-{5-cyano-2-[(R)-6-methoxy-carbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-ammonium forma | Rt = 3.477 min, m/z = 617.3 [M]+ | $^1$H NMR (400 MHz, DMSO) δ 11.53 (1H, bs), 8.40 (1.8H, s, formate), 8.13 (1H, bs), 7.93 (2H, m), 7.86 (1H, d, J = 1.5 Hz), 7.83 (1H, t, J = 8.0 Hz), 7.77 (1H, dd, J = 1.6, 8.1 Hz), 7.65 (2H, m), 7.54 (3H, m), 6.28 (1H, s), 4.66 (2H, J = 12.8 Hz), 4.04 (2H, m, obscured), 3.51 (3H, s), 3.48 (2H, m), 3.13 (6H, s), 2.16 (3H, s). |
| 80 | 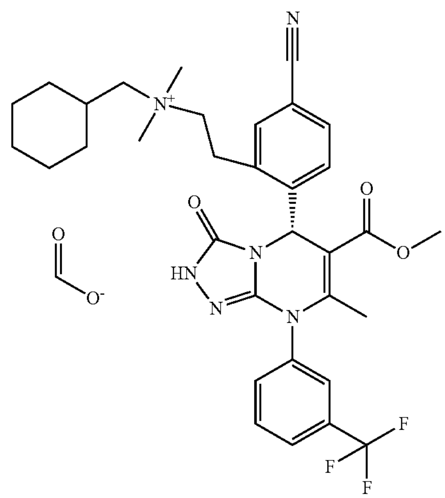 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclohexylmethyl-dimethyl-ammonium formate | Rt = 3.96 min, m/z = 623.4 [M]+ | $^1$H NMR (400 MHz, DMSO) δ 11.53 (1H, bs), 8.40 (1.7H, s, formate), 8.13 (1H, bs), 7.93 (2H, m), 7.83 (2H, m), 7.76 (1H, dd, J = 1.6, 8.0 Hz), 7.71 (1H, d, J = 8.1 Hz), 6.23 (1H, s), 4.05 (2H, m), 3.54 (3H, s, obscured), 3.36 (2H, m, obscured), 3.27 (2H, m), 3.19 (6H, s), 2.16 (3H, s), 2.04 (1H, m), 1.84 (2H, m), 1.66 (2H, m), 1.58 (1H, m), 1.39-1.25 (2H, m), 1.20-1.07 (3H, m). |
| 81 | 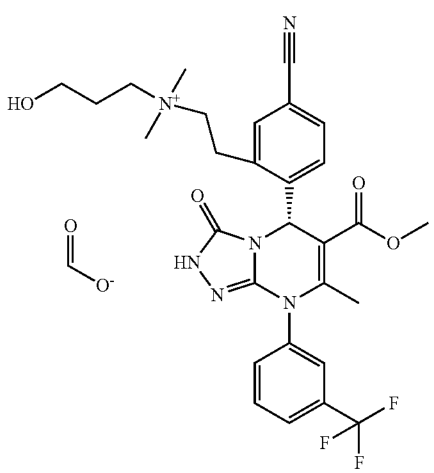 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(3-hydroxy-propyl)-dimethyl-ammonium formate | Rt = 3.40 min, m/z = 585.3 [M]+ | $^1$H NMR (400 MHz, DMSO) δ 11.50 (1H, bs), 8.44 (1.5H, s, formate), 8.13 (1H, bs), 7.93 (2H, m), 7.86 (1H, d, J = 1.2 Hz), 7.83 (1H, t, J = 7.9 Hz), 7.76 (1H, dd, J = 8.1, 1.7 Hz), 7.70 (1H, d, J = 8.1 Hz), 6.25 (1H, s), 4.02 (1H, m), 3.66-3.30 (10H, m, obscured), 3.19 (3H, s), 3.18 (3H, s), 2.16 (3H, s), 1.95 (2H, m). |

-continued

| Example | Structure | Name | LC-MS (Method 3) | NMR |
|---|---|---|---|---|
| 82 | 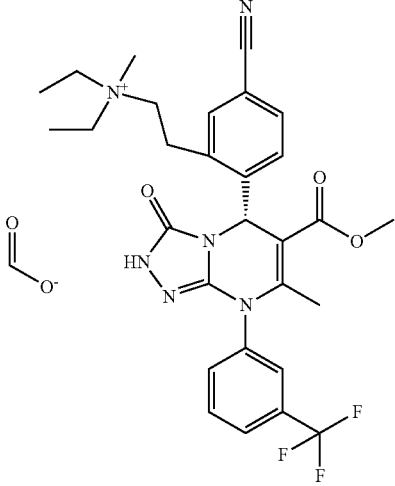 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-diethyl-methyl-ammonium forma | Rt = 3.55 min, m/z = 569.3 [M]$^+$ | $^1$H NMR (400 MHz, DMSO) δ 11.52 (1H, bs), 8.42 (1.6H, s, formate), 8.13 (1H, bs), 7.93 (2H, m), 7.87 (1H, d, J = 1.2 Hz), 7.83 (1H, t, J = 7.8 Hz), 7.76 (1H, dd, J = 8.0, 1.6 Hz), 7.70 (1H, d, J = 8.2 Hz), 6.22 (1H, s), 4.00 (1H, m), 3.67-3.28 (10H, m, obscured), 3.11 (3H, s), 2.16 (3H, s), 1.32 (6H, m). |
| 83 | 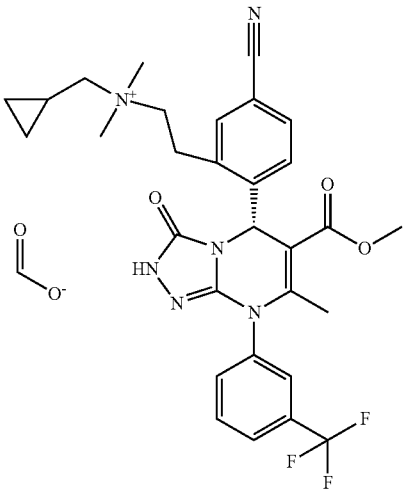 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclopropylmethyl-dimethyl-ammonium formate | Rt = 3.62 min, m/z = 581.2 [M]$^+$ | $^1$H NMR (400 MHz, DMSO) δ 11.51 (1H, bs), 8.41 (1.6H, s, formate), 8.13 (1H, bs), 7.92 (2H, m), 7.86 (1H, d, J= 1.3 Hz), 7.82 (1H, t, J = 7.9 Hz), 7.76 (1H, dd, J = 8.1, 1.7 Hz), 7.70 (1H, d, J = 8.1 Hz), 6.25 (1H, s), 4.08 (2H, m), 3.53 (3H, s), 3.41-3.31 (4H, m), 3.21 (6H, s), 2.16 (3H, s), 1.28 (1H, m), 0.73 (2H, m), 0.46 (2H, m). |
| 84 | 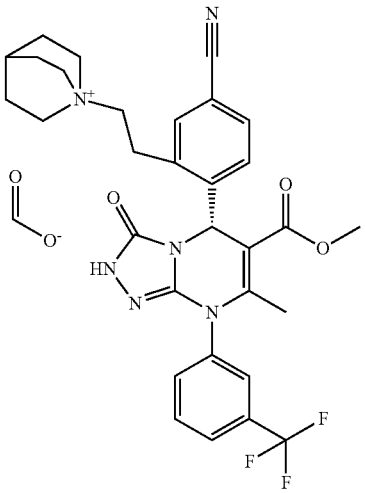 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-azonia-bicyclo[2.2.2]octane formate | Rt = 3.56 min, m/z = 593.3 [M]$^+$ | $^1$H NMR (400 MHz, DMSO) δ 11.53 (1H, bs), 8.41 (1.7H, s, formate), 8.13 (1H, bs), 7.93 (2H, m), 7.83 (2H, m), 7.75 (1H, dd, J = 8.1, 1.8 Hz), 7.70 (1H, d, J = 8.2 Hz), 6.25 (1H, s), 3.88-3.47 (11H, m, obscured), 3.32 (2H, m), 2.16 (3H, s), 2.12 (1H, m), 1.94 (6H, m). |

-continued

| Example | Structure | Name | LC-MS (Method 3) | NMR |
|---|---|---|---|---|
| 85 | 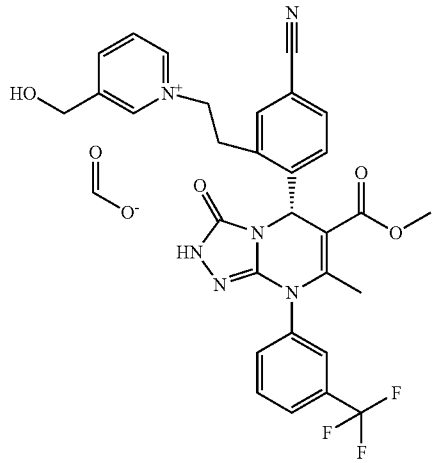 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-hydroxymethyl-pyridinium formate | Rt = 3.45 min, m/z = 591.2 [M]⁺ | ¹H NMR (400 MHz, DMSO) δ 11.57 (1H, bs), 9.17 (1H, s), 9.00 (1H, d, J = 8 Hz), 8.57 (1H, d, J = 8 Hz), 8.47 (1.3H, s, formate), 8.22-8.10 (2H, m), 7.99-7.89 (2H, m), 7.88-7.72 (4H, m), 6.45 (1H, s), 5.27-5.06 (2H, m), 4.78 (2H, s), 3.69-3.52 (2H, m, obscured), 3.94-3.82 (1H, m), 3.50 (3H, s), 2.17 (3H, s). |
| 86 | 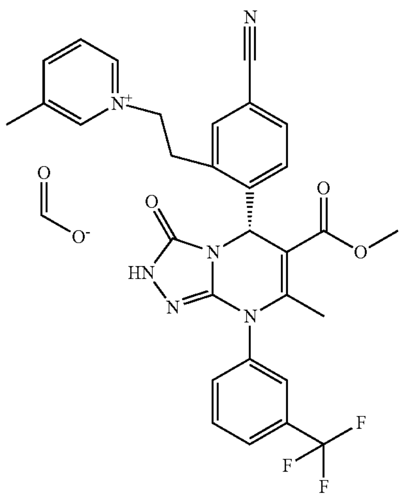 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-methyl-pyridinium formate | Rt = 3.58 min, m/z = 575.2 [M]⁺ | ¹H NMR (400 MHz, DMSO) δ 11.58 (1H, bs), 9.06 (1H, s), 8.90 (1H, d, J = 6 Hz), 8.51 (1H, d, J = 8 Hz), 8.43 (1.5H, s, formate), 8.19-8.08 (2H, m), 7.97-7.88 (2H, m), 7.86-7.71 (3H, m), 7.68 (1H, m), 6.43 (1H, s), 5.22-5.00 (2H, m), 3.94-3.50 (2H, m, obscured), 3.47 (3H, s), 2.54 (3H, s), 2.16 (3H, s). |

\*= for tertiary amine preparation see Intermediate 26.

Intermediate 27

(1,1-Dioxo-hexahydro-1lambda\*6\*-thiopyran-4-ylmethyl)-dimethylamine

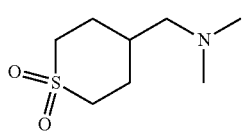

[(1,1-Dioxotetrahydro-2H-thiopyran-4-yl)methyl]amine (500 mg, 3.07 mmol) was dissolved in formic acid (1 mL) and formaldehyde (37% in water, 1 mL) and the reaction mixture was heated to 65° C. for 4 hours. The mixture was cooled and carefully poured onto aqueous NaHCO₃ and washed with EtOAc. The aqueous layer was basified to pH 13 with NaOH and extracted into 2-MethylTHF (3×). The combined organic extract was dried (MgSO₄), filtered and concentrated in vacuo and resultant residue was purified by chromatography eluting from 0-10% (2M NH₃ in MeOH) in DCM to give the title compound as a clear oil (80 mg).

¹H NMR (400 MHz, CDCl₃) δ 3.11 (4H, m), 2.20 (6H, s), 2.24-2.12 (4H, m), 1.88-1.57 (3H, m).

Intermediate 28

Dimethyl-oxetan-3-ylmethyl-amine

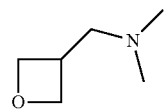

Oxetan-3-yl-methylamine (0.25 g, 2.87 mmol) was dissolved in a mixture of formaldehyde (37% solution in water; 1 mL) and formic acid (1 mL) then heated at 65° C. for 4 hours The reaction mixture was poured into aqueous sodium hydroxide/brine and extracted with Et₂O. The organic layer was dried over MgSO$_4$, filtered and carefully concentrated in vacuo to afford the title compound as a residue still containing traces of Et$_2$O (0.11 g).

$^1$H NMR (300 MHz, CDCl$_3$): δ 4.80 (2H, m), 4.38-4.45 (2H, m), 3.09-3.28 (1H, m), 2.62 (2H, d, J=7.4 Hz), 2.20 (6H, s).

Intermediate 29

4-Dimethylamino-N-methyl-butyramide

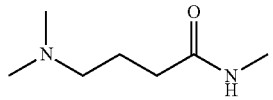

A stirred solution of 4-dimethylamino-butyric acid hydrochloride salt (0.50 g, 2.98 mmol; for reference procedure from 4-aminobutyric acid see *JACS*, 1963, 85, 1-8) and DIPEA (3.22 mL, 18.50 mmol) in DMF (5 mL) was treated with a methylamine solution (2 M in THF; 5.96 mL, 11.93 mmol) and then HATU (1.42 g, 3.73 mmol). The mixture was stirred at RT for 4 hours before being diluted with MeOH (15 mL). This resultant solution was purified via a SCX-2 cartridge and the relevant fractions were concentrated in vacuo to afford the title compound as a colourless oil (0.31 g).

$^1$H NMR (300 MHz, DMSO): δ 7.66 (1H, bs), 2.54 (3H, d, J=4.6 Hz), 2.15 (2H, t, J=7.2 Hz), 2.09 (6H, s), 2.04 (2H, t, J=7.5 Hz), 1.53-1.65 (2H, m).

Intermediate 30

3-Dimethylamino-propane-1-sulfonic acid dimethylamide

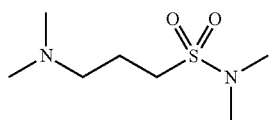

a) 3-Chloro-propane-1-sulfonic acid dimethylamide.

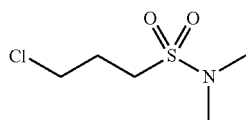

A stirred solution of 3-chloropropylsulfonylchloride (6.00 g, 33.90 mmol) in THF (35 mL) was cooled in an ice bath to 0-5° C. Dimethylamine (2 M in THF; 36 mL, 72 mmol) was added drop-wise, maintaining the temperature below 10° C., and the resultant suspension stirred at 5° C. for 30 minutes then allowed to warm to RT. After 1 hour, the mixture was diluted with water and extracted into EtOAc and the extract washed with water, brine and then dried (Na$_2$SO$_4$), filtered and concentrated in vacuo to afford the title compound as a pale yellow oil (5.19 g).

$^1$H NMR (400 MHz, CDCl$_3$): δ 3.70 (2H, t, J 6.2 Hz), 3.06-3.12 (2H, m), 2.90 (6H, s), 2.25 (2H, m).

b) 3-Dimethylamino-propane-1-sulfonic acid dimethylamide.

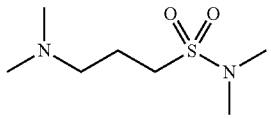

A solution of 3-chloro-propane-1-sulfonic acid dimethylamide (0.55 g, 3.00 mmol) in MeCN (5 mL) was treated with dimethylamine (2 M in THF; 10 mL, 20 mmol), potassium carbonate (455 mg, 3.30 mmol) and a catalytic amount of potassium iodide (50 mg, 0.03 mmol). This mixture was heated in a sealed tube at 65° C. for 18 hours, then cooled and diluted with water and extracted into EtOAc. The organic extract was washed with brine then dried (Na$_2$SO$_4$), filtered and concentrated in vacuo to afford the title compound as a pale brown oil (0.40 g).

$^1$H NMR (400 MHz, CDCl$_3$): δ 3.01-2.95 (2H, m), 2.88 (6H, s), 2.38 (2H, t, J=6.8 Hz), 2.22 (6H, s), 2.02-1.92 (2H, m).

Intermediate 31

4-Methyl-[1,4]oxazepane

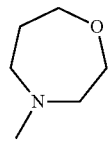

[1,4]Oxazepane hydrochloride (730 mg, 5.3 mmol), and NaHCO$_3$ (450 mg, 5.3 mmol) were suspended in formic acid (2 mL) and a formaldehyde solution (37 wt % in water; 1 mL) and heated to reflux for 5.5 hours. The reaction was cooled, and a solution of NaOH (2 g in 5 mL water) was added cautiously. The product was then extracted with Et$_2$O (50 mL), dried (Na$_2$SO$_4$) and the solvent removed by distillation at atmospheric pressure to afford of a light brown liquid that contained some residual Et$_2$O (680 mg).

$^1$H NMR (300 MHz, CDCl$_3$) δ 3.85-3.78 (2H, m), 3.76-3.70 (2H, m), 2.68-2.59 (4H, m), 2.41-2.37 (3H, m), 1.98-1.88 (2H, m).

Intermediate 32

(3-Methanesulfonylpropyl)dimethylamine

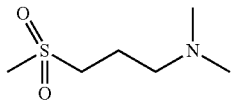

1-Bromo-3-methanesulfonylpropane (500 mg, 2.5 mmol) was suspended in a dimethylamine solution (2 M in THF; 10 mL, 20 mmol) and stirred at RT, resulting in a crystalline solid. The reaction was left to stand overnight and the reaction mixture was then diluted with Et$_2$O (10 mL) and filtered. The filtrate was concentrated in vacuo resulting in an orange oily solid which was redissolved in Et$_2$O (10 mL), filtered and concentrated in vacuo to give the title compound as an orange oil (420 mg).

$^1$H NMR (300 MHz, CDCl$_3$) δ 3.07-2.99 (2H, m), 2.84 (3H, m), 2.34 (2H, t, J=6.7 Hz), 2.16 (6H, s), 2.00-1.88 (2H, m).

The following examples were prepared from Intermediate 14 and the appropriately substituted tertiary amines or basic heterocycles using an analogous method to that used in Example 24 (all tertiary amines/basic heterocycles were known or commercially available unless otherwise stated). Where the tertiary amine used was limiting, the reaction mixture was diluted further with MeCN. Following purification by MDAP and lyophilisation, the title compounds were obtained as white electrostatic solids:

| Example | Structure | Name | LC-MS (Method 3) | NMR |
|---|---|---|---|---|
| 87 | 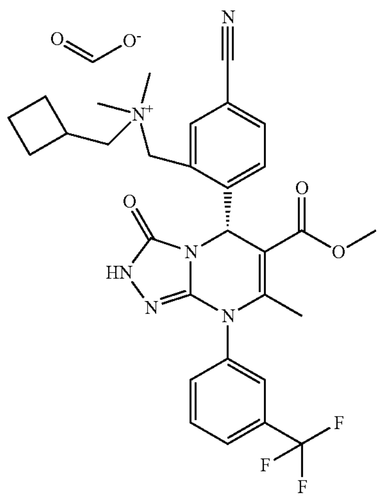 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-cyclobutylmethyl-dimethyl-ammonium formate | Rt = 3.66 min, m/z = 581.2 [M]$^+$ | $^1$H NMR (400 MHz, DMSO) δ 11.63 (1H, bs), 8.46 (1.5H, s, formate), 8.10 (2H, m), 8.02 (1H, dd, J = 8.3, 1.5 Hz), 7.95-7.79 (4H, m), 6.45 (1H, s), 5.06 (1H, d, J = 14.3 Hz), 4.91 (1H, d, J = 14.3 Hz), 3.67-3.56 (2H, m, obscured), 3.53 (3H, s), 3.16 (3H, s), 3.12 (3H, s), 3.07-2.94 (1H, m), 2.23-2.12 (2H, m), 2.07 (3H, s), 2.02-1.88 (3H, m), 1.86-1.75 (1H, m). |
| 88* | 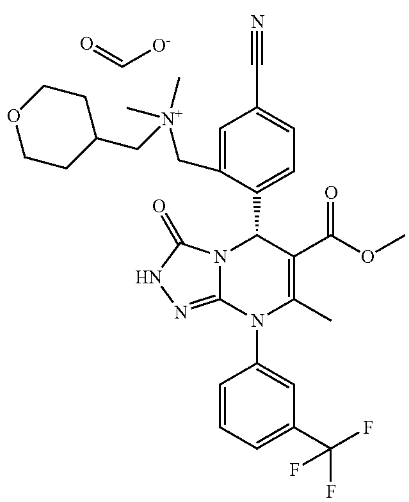 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(tetrahydro-pyran-4-ylmethyl)-ammonium formate | Rt = 3.45 min, m/z = 611.3 [M]$^+$ | $^1$H NMR (400 MHz, DMSO) δ 11.54 (1H, bs), 8.46 (1.4H, s, formate), 8.13 (1H, d, J = 1.7 Hz), 8.12-8.08 (1H, m), 8.03 (1H, dd, J = 8.2, 1.7 Hz), 7.95-7.79 (4H, m), 6.49 (1H, s), 5.15 (1H, d, J = 14.2 Hz), 4.97 (1H, d, J = 14.2 Hz), 3.90-3.82 (2H, m, obscured), 3.53 (3H, s, obscured), 3.57-3.35 (4H, m, obscured), 3.25 (3H, s), 3.18 (3H, s), 2.45-2.35 (1H, m), 2.07 (3H, s), 1.82-1.73 (2H, m), 1.51-1.38 (2H, m). |

| Example | Structure | Name | LC-MS (Method 3) | NMR |
|---|---|---|---|---|
| 89 | 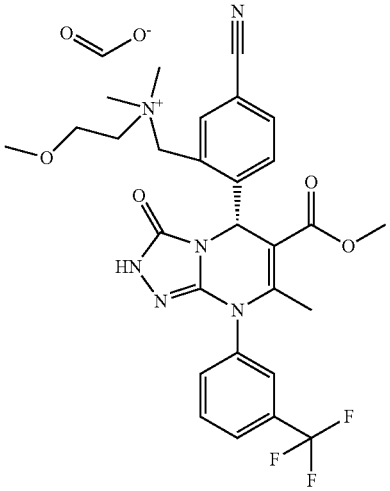 | {{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(2-methoxy-ethyl)-dimethyl-ammonium formate | Rt = 3.45 min, m/z = 571.2 [M]⁺ | ¹H NMR (400 MHz, DMSO) δ 11.58 (1H, bs), 8.41 (1.7H, s, formate), 8.14 (1H, d, J = 1.6 Hz), 8.11 (1H, bs), 8.02 (1H, dd, J = 8.3, 1.6 Hz), 7.95-7.79 (4H, m), 6.48 (1H, s), 5.15-5.05 (2H, m), 3.91-3.77 (4H, m), 3.53 (3H, s), 3.36 (3H, s), 3.25 (3H, s), 3.23 (3H, s), 2.06 (3H, s). |
| 90 | 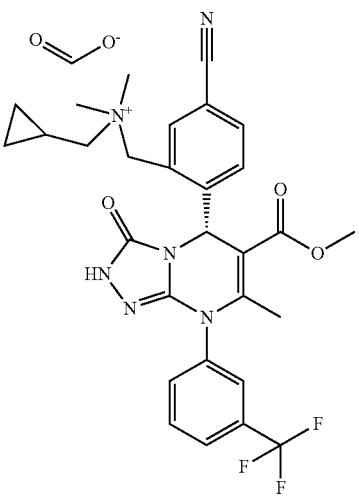 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-cyclopropyl-methyl-dimethyl-ammonium formate | Rt = 3.52 min, m/z = 567.3 [M]⁺ | ¹H NMR (400 MHz, DMSO) δ 11.60 (1H, bs), 8.43 (1.6H, s, formate), 8.13 (1H, d, J = 1.6 Hz), 8.10 (1H, bs), 8.02 (1H, dd, J = 8.3, 1.6 Hz), 7.95-7.79 (4H, m), 6.45 (1H, s), 5.15 (1H, d, J = 14.2 Hz), 5.01 (1H, d, J = 14.2 Hz), 3.54 (3H, s), 3.52-3.46 (2H, m), 3.27 (3H, s), 3.22 (3H, s), 2.07 (3H, s), 1.33-1.21 (1H, m), 0.79-0.72 (2H, m), 0.54-0.45 (2H, m). |
| 91 | 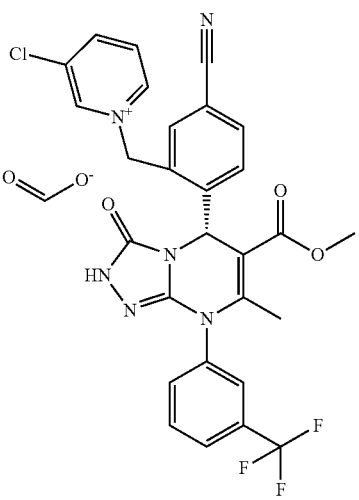 | 3-Chloro-1-{5-cyano-2-[(R)-6-methoxy-carbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium formate | Rt = 3.50 min, m/z = 581.1 [M]⁺ | ¹H NMR (400 MHz, DMSO) δ 11.63 (1H, bs), 9.74 (1H, s), 9.33 (1H, d, J = 5.9 Hz), 8.86 (1H, dd, J = 8.5, 1.3 Hz), 8.44 (1.5H, s, formate), 8.31-8.24 (1H, m), 8.23-8.10 (1H, bm), 7.98-7.89 (4H, m), 7.87-7.79 (2H, m), 6.56 (1H, d, J = 15.4 Hz), 6.42 (1H, s), 6.11 (1H, d, J = 15.4 Hz), 3.57 (3H, s), 2.18 (3H, s). |

-continued

| Example | Structure | Name | LC-MS (Method 3) | NMR |
|---|---|---|---|---|
| 92 | 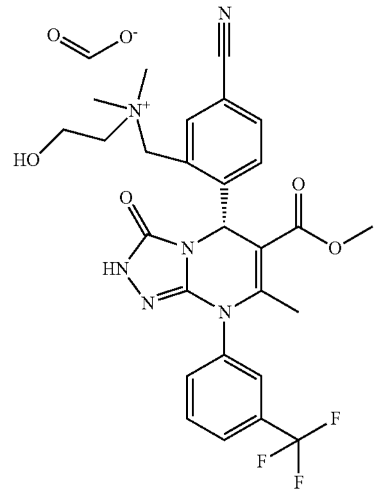 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(2-hydroxy-ethyl)-dimethyl-ammonium formate | Rt = 3.28 min, m/z = 557.2 [M]+ | $^1$H NMR (400 MHz, DMSO) δ 11.55 (1H, bs), 8.46 (1.3H, s, formate), 8.16 (1H, d, J = 1.63 Hz), 8.11 (1H, bs), 8.02 (1H, dd, J = 8.3, 1.6 Hz), 7.96-7.79 (4H, m), 6.50 (1H, s), 5.19-5.07 (2H, m), 3.99 (2H, t, J = 4.7 Hz), 3.72-3.65 (2H, m, obscured), 3.53 (3H, s, obscured), 3.27 (3H, s), 3.25 (3H, s), 2.06 (3H, s). |
| 93 | 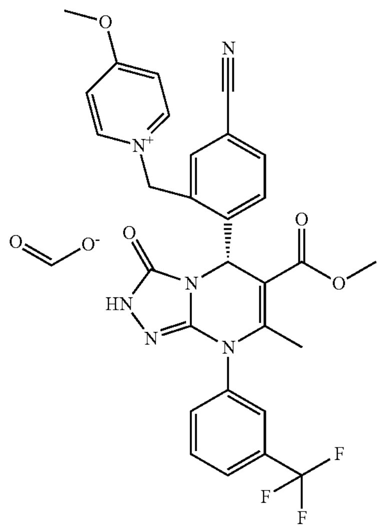 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methoxy-pyridinium formate | Rt = 3.49 min, m/z = 577.2 [M]+ | $^1$H NMR (400 MHz, DMSO) δ 11.72 (1H, bs), 9.16-9.11 (2H, m), 8.46 (1.3H, s, formate), 8.17 (1H, bs), 7.98-7.79 (5H, m), 7.76-7.71 (2H, m), 7.60 (1H, d, J = 1.1 Hz), 6.47-6.40 (2H, m), 5.92 (1H, d, J = 15.4 Hz), 4.14 (3H, s), 3.57 (3H, s), 2.19 (3H, s). |
| 94 | 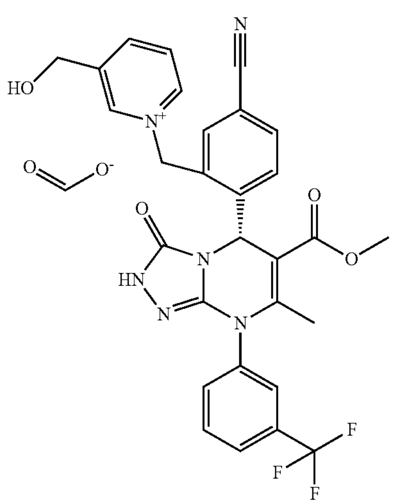 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-3-hydroxymethyl-pyridinium formate | Rt = 3.34 min, m/z = 577.2 [M]+ | $^1$H NMR (400 MHz, DMSO) δ 11.62 (1H, bs), 9.35 (1H, s), 9.24 (1H, d, J = 6.0 Hz), 8.60 (1H, d, J = 7.8 Hz), 8.44 (1.4H, s, formate), 8.23-8.16 (2H, m), 7.98-7.79 (5H, m), 7.70 (1H, d, J = 1.2 Hz), 6.59 (1H, d, J = 15.2 Hz), 6.43 (1H, s), 6.14 (1H, d, J = 15.2 Hz), 4.76 (2H, s), 3.55 (3H, s, obscured 2.19 (3H, s). |

-continued

| Example | Structure | Name | LC-MS (Method 3) | NMR |
|---|---|---|---|---|
| 95 | 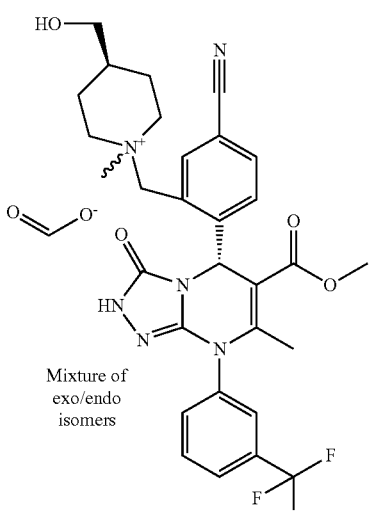 Mixture of exo/endo isomers | {1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-hydroxymethyl-1-methyl-piperidinium formate | Rt = 3.30 min, m/z = 597.2 [M]+ | $^1$H NMR (400 MHz, DMSO) δ 11.44 (1H, bs), 8.37 (1.4H, s, formate), 8.15-8.08 (1.6H, m), 8.05-7.99 (1.4H, m), 7.96-7.99 (4H, m), 6.52, 6.38 (1H, 2 × s), 5.17-4.96 (2H, m), 4.01-3.81 (2H, m), 3.73-3.23 (4H, m), 3.56, 3.53 (3H, 2 × s), 3.14, 3.06 (3H, 2 × s), 2.08, 2.06 (3H, 2 × s), 2.03-1.57 (5H, m). |
| 96 | 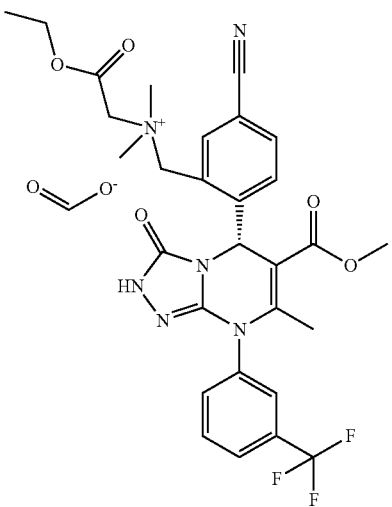 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-ethoxycarbonyl-methyl-dimethyl-ammonium formate | Rt = 3.61 min, m/z = 599.4 [M]+ | $^1$H NMR (400 MHz, DMSO) δ 11.56 (1H, bs), 8.41 (1.5H, s, formate), 8.14 (1H, d, J = 1.6 Hz), 8.12 (1H, bs), 8.04 (1H, dd, J = 8.4, 1.6 Hz), 7.96-7.79 (4H, m), 6.42 (1H, s), 5.33-5.24 (2H, m), 4.64-4.56 (2H, m), 4.29 (2H, q, J = 7.1 Hz), 3.54 (3H, s, obscured 3.41 (3H, s), 3.36 (3H, s), 2.08 (3H, s), 1.28 (3H, t, J = 7.2 Hz). |
| 97* | 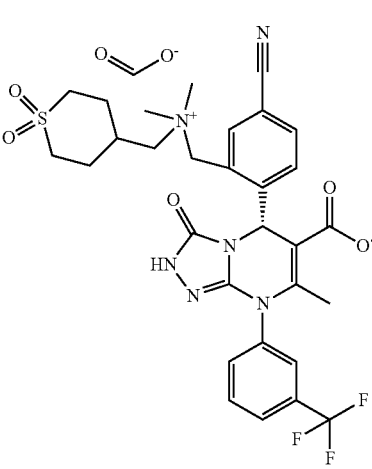 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(1,1-dioxo-hexahydro-1lambda*6*-thiopyran-4-ylmethyl)-dimethyl-ammonium formate | Rt = 3.38 min, m/z = 659.3 [M]+ | $^1$H NMR (400 MHz, DMSO TFA-D added) δ 8.14 (1.2H, s), 8.12 (1H, d, J = 1.6 Hz), 8.10 (1H, bs), 8.04 (1H, dd, J = 8.3, 1.6 Hz), 7.95-7.80 (4H, m), 6.51 (1H, s), 5.18 (1H, d, J = 14.0 Hz), 5.02 (1H, d, J = 14.0 Hz), 3.64-3.52 (2H, m), 3.56 (3H, s), 3.27 (3H, s), 3.23 (3H, s), 3.21-3.10 (4H, m), 2.56-2.51 (1H, m, obscured), 2.24-2.14 (2H, m), 2.10 (3H, s), 2.05-1.91 (2H, m). |

-continued

| Example | Structure | Name | LC-MS (Method 3) | NMR |
|---|---|---|---|---|
| 98 | 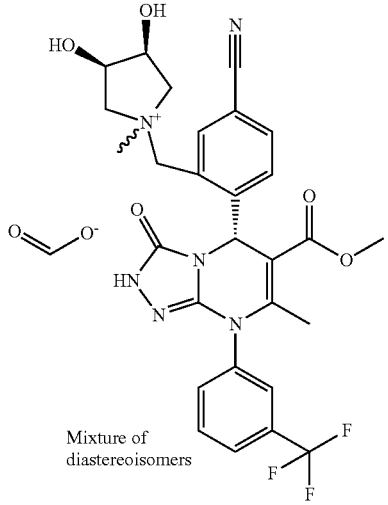 Mixture of diastereoisomers | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-3,4-dihydroxy-1-methyl-pyrrolidinium formate | Rt = 3.28 min, m/z = 585.3 [M]+ | $^1$H NMR (400 MHz, DMSO) δ 11.38 (1H, bs), 8.47 (1.1H, s, formate), 8.19-8.06 (2H, m), 8.02-7.78 (5H, m), 6.49-6.45 (1H, 2 × s), 5.95 (1H, bs), 5.25, 5.10 (2H, 2 × d, J = 14.5 Hz, 1 × s), 4.49-4.37 (2H, m), 4.19-4.06 (2H, m), 3.90 (1H, d, J = 5.7 Hz), 3.81-3.64 (2H, m), 3.53 (3H, s), 3.37, 3.17 (3H, 2 × s), 2.09, 2.08 (3H, 2 × s). |
| 99 | 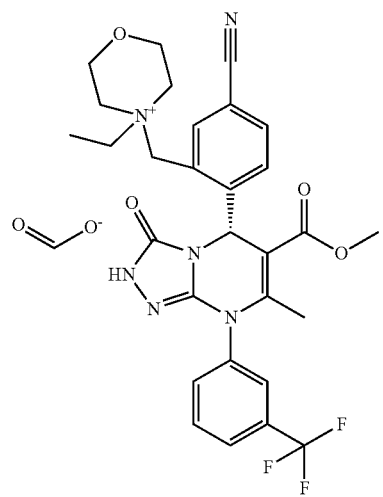 | 4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-ethyl-morpholin-4-ium formate | Rt = 3.42 min, m/z = 583.3 [M]+ | $^1$H NMR (400 MHz, DMSO) δ 11.59 (1H, bs), 8.49 (1.2H, s, formate), 8.14-7.99 (3H, m), 7.97-7.76 (4H, m), 6.40 (1H, s), 5.23-4.97 (2H, m), 4.12-3.75 (7H, m), 3.69-3.57 (3H, m), 3.56 (3H, s), 2.07 (3H, s), 1.45-1.34 (3H, m). |
| 100 | 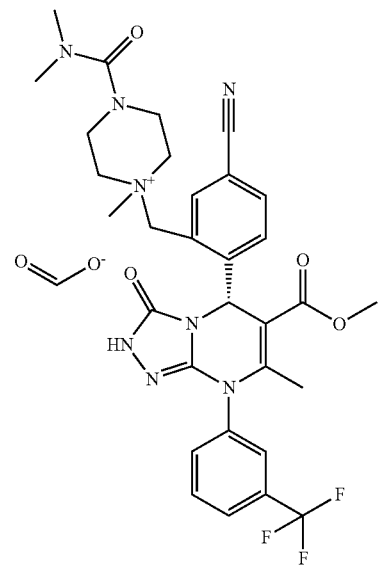 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-dimethyl-carbamoyl-1-methyl-piperazin-1-ium formate | Rt = 3.38 min, m/z = 639.3 [M]+ | $^1$H NMR (400 MHz, DMSO) δ 11.69 (1H, bs), 8.48 (1.3H, s, formate), 8.16-8.06 (2H, m), 8.04-7.99 (1H, m), 7.95-7.79 (4H, m), 6.48 (1H, s), 5.24-4.95 (2H, m), 3.80-3.60 (7H, m), 3.44-3.18 (10H, m), 2.67 (3H, s), 2.07 (3H, s). |

-continued

| Example | Structure | Name | LC-MS (Method 3) | NMR |
|---|---|---|---|---|
| 101 | 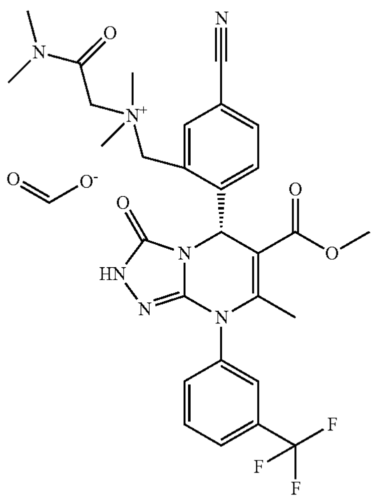 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-carbamoyl-methyl-dimethyl-ammonium formate | Rt = 3.44 min, m/z = 598.2 [M]+ | ¹H NMR (400 MHz, DMSO) δ 11.57 (1H, bs), 8.39 (1.8H, s, formate), 8.16-8.08 (2H, m), 8.04-7.99 (1H, m), 7.96-7.78 (4H, m), 6.42 (1H, s), 5.51-5.23 (2H, m), 4.79-4.56 (2H, m), 3.53 (3H, s), 3.41 (3H, s), 3.34 (3H, s), 3.00 (3H, s), 2.94 (3H, s), 2.06 (3H, s). |
| 102 | 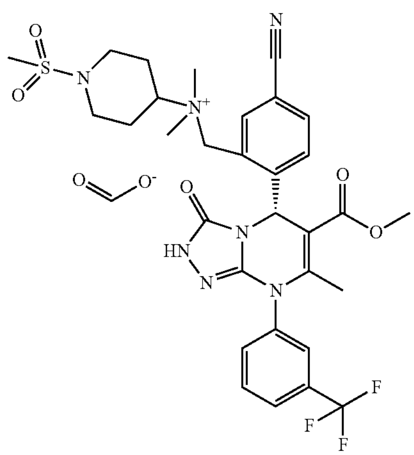 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(1-methanesulfonyl-piperidin-4-yl)-dimethyl-ammonium formate | Rt = 3.46 min, m/z = 674.3 [M]+ | ¹H NMR (400 MHz, DMSO) δ 11.58 (1H, bs), 8.45 (1.5H, s, formate), 8.15-8.06 (2H, m), 8.05-7.99 (1H, m), 7.96-7.79 (4H, m), 6.37 (1H, s), 5.27-4.81 (2H, m), 3.98-3.79 (3H, m), 3.54 (3H, s, obscured), 3.22 (3H, s), 3.09 (3H, s), 2.91 (3H, s), 2.92-2.80 (2H, m), 2.48-2.39 (2H, m), 2.09 (3H, s), 2.07-1.91 (2H, m). |
| 103* | 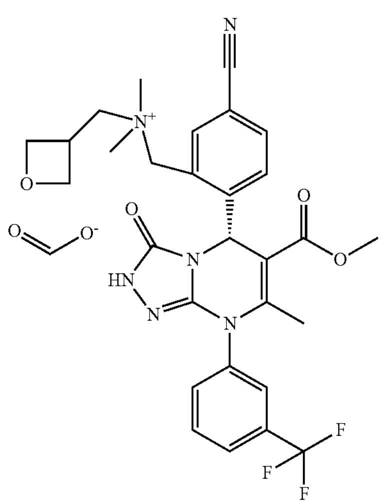 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-oxetan-3-ylmethyl-ammonium formate | Rt = 3.32 min, m/z = 583.3 [M]+ | ¹H NMR (400 MHz, DMSO) δ 11.60 (1H, bs), 8.50 (1.2H, s, formate), 8.14-8.06 (2H, m), 8.04-7.99 (1H, m), 7.95-7.78 (4H, m), 6.50 (1H, s), 5.13-4.87 (2H, m), 4.77-4.66 (2H, m), 4.59-4.50 (2H, m), 3.98-3.74 (3H, m), 3.54 (3H, s), 3.15 (3H, s), 3.11 (3H, s), 2.07 (3H, s). |

-continued

| Example | Structure | Name | LC-MS (Method 3) | NMR |
|---|---|---|---|---|
| 104* | 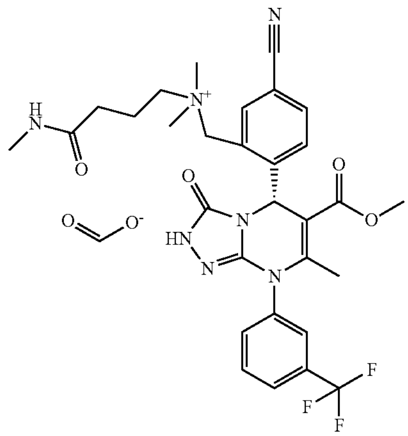 | (5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(3-methylcarbamoyl-propyl)-ammonium formate | Rt = 3.28 min, m/z = 612.3 [M]+ | $^1$H NMR (400 MHz, DMSO) δ 11.42 (1H, bs), 8.38 (1.5H, s, formate), 8.09-8.07 (1H, m), 8.05 (1H, bs), 7.99-7.94 (1H, m), 7.90-7.74 (5H, m), 6.42 (1H, s), 5.08-4.88 (2H, m), 3.52-3.46 (5H, m, obscured), 3.16 (3H, s), 3.11 (3H, s), 2.55 (3H, d, J 4.5 Hz), 2.20-2.14 (2H, m), 2.08-1.99 (5H, m). |
| 105* | 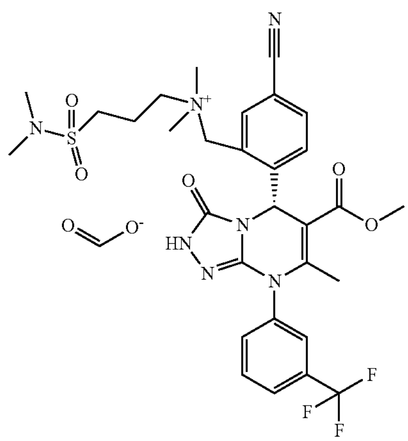 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-dimethyl-sulfamoyl-propyl)-dimethyl-ammonium formate | Rt = 3.52 min, m/z = 662.2 [M]+ | $^1$H NMR (400 MHz, DMSO) δ 11.50 (1H, bs), 8.44 (1.5H, s, formate), 8.13-8.08 (2H, m), 8.05-8.00 (1H, m), 7.95-7.79 (4H, m), 6.48 (1H, s), 5.18-4.98 (2H, m), 3.68-3.60 (2H, m), 3.54 (3H, s), 3.25 (3H, s), 3.22 (3H, s), 3.15 (2H, t, J = 7.5 Hz), 2.81 (6H, s), 2.28-2.17 (2H, m), 2.07 (3H, s). |
| 106 | 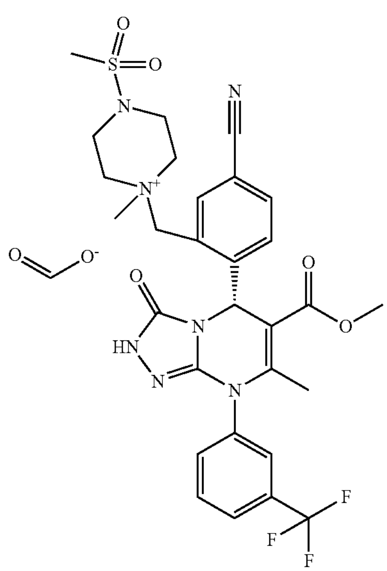 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methanesulfonyl-1-methyl-piperazin-1-ium formate | Rt = 3.40 min, m/z = 646.2 [M]+ | $^1$H NMR (400 MHz, DMSO) δ 11.62 (1H, bs), 8.45 (1.4H, s, formate), 8.14-8.07 (2H, m), 8.06-8.01 (1H, m), 7.95-7.79 (4H, m), 6.55 (1H, s), 5.28-5.09 (2H, m), 3.96-3.84 (2H, m), 3.80-3.66 (4H, m, obscured), 3.57-3.43 (2H, m, obscured), 3.54 (3H, s), 3.27 (3H, s), 3.05 (3H, s), 2.07 (3H, s). |

| Example | Structure | Name | LC-MS (Method 3) | NMR |
|---|---|---|---|---|
| 107 | 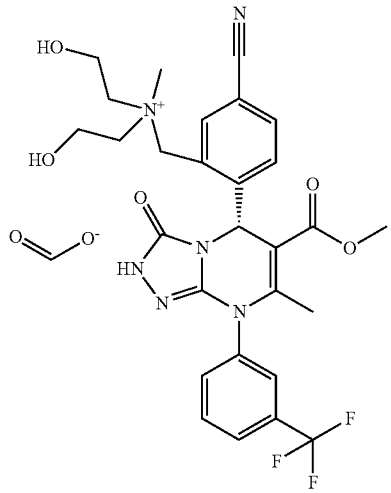 | (5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-bis-(2-hydroxy-ethyl)-methyl-ammonium formate | Rt = 3.26 min, m/z = 587.3 [M]+ | $^1$H NMR (400 MHz, DMSO) δ 11.52 (1H, bs), 8.49 (1.2H, s, formate), 8.24-8.18 (1H, m), 8.11 (1H, bs), 8.03-7.98 (1H, m), 7.95-7.78 (4H, m), 6.50 (1H, s), 5.31-5.16 (2H, m), 4.06-3.79 (6H, m), 3.72-3.62 (2H, m), 3.53 (3H, s), 3.23 (3H, s), 2.05 (3H, s). |
| 108 | 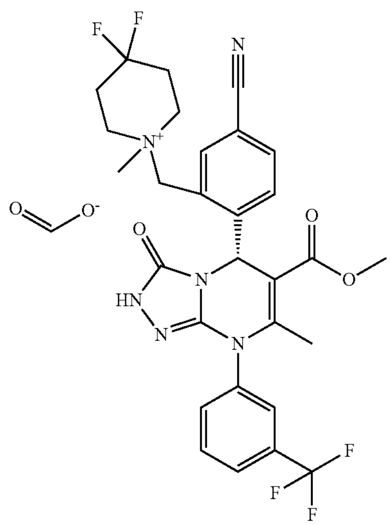 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4,4-difluoro-1-methyl-piperidinium formate | Rt = 3.52 min, m/z = 603.2 [M]+ | $^1$H NMR (400 MHz, DMSO) δ 11.59 (1H, bs), 8.41 (1.7H, s, formate), 8.14-8.08 (2H, m), 8.06-8.01 (1H, m), 7.95-7.79 (4H, m), 6.55 (1H, s), 5.28-5.11 (2H, m), 3.94-3.73 (5H, m, obscured), 3.54 (3H, s), 3.27 (3H, s), 2.67-2.54 (1H, m), 2.46-2.35 (2H, m), 2.06 (3H, s). (98007) |
| 109* | 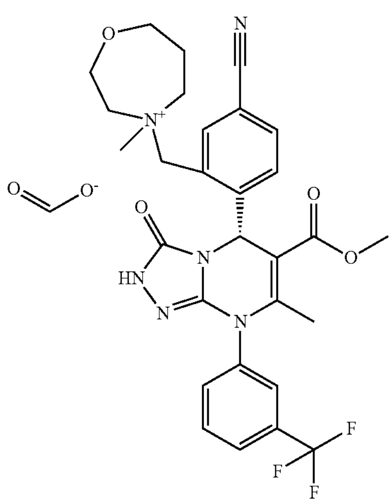 | 4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-[1,4]oxazepan-4-ium formate | Rt = 3.37 min, m/z = 583.4 [M]+ | $^1$H NMR (400 MHz, DMSO) δ 11.25 (1H, very bs), 8.43 (1.4H, s, formate), 8.14 (1H, d, J = 1.3 Hz), 8.11 (1H, bs), 8.05-8.01 (1H, m), 7.95-7.79 (4H, m), 6.46 (1H, s), 5.22-5.05 (2H, m), 4.09-3.87 (4H, m), 3.82-3.63 (4H, m), 3.54 (3H, d, J = 2.8 Hz), 3.25 (3H, m), 2.31-2.19 (1H, m), 2.15-2.10 (1H, m), 2.06 (3H, d, J 1.9). |

-continued

| Example | Structure | Name | LC-MS (Method 3) | NMR |
|---|---|---|---|---|
| 110 | 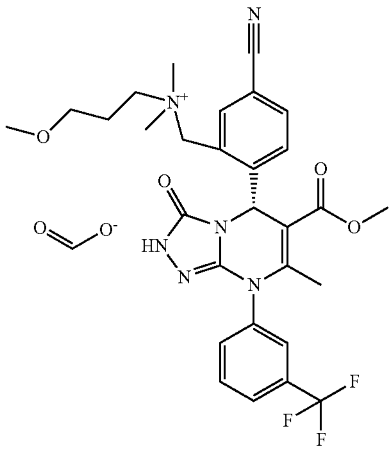 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-methoxy-propyl)-dimethyl-ammonium formate | Rt = 3.49 min, m/z = 585.3 [M]+ | ¹H NMR (400 MHz, DMSO) δ 11.61 (1H, bs), 8.44 (1.4H, s, formate), 8.12 (1H, d, J = 1.6 Hz), 8.11 (1H, bs), 8.02 (1H, dd, J = 8.3, 1.8 Hz), 7.95-7.78 (4H, m), 6.47 (1H, s), 5.13 (1H, d, J = 14.2 Hz), 4.96 (1H, d, J = 14.2 Hz), 3.66-3.59 (2H, m), 3.53 (3H, s), 3.47 (2H, t, J = 5.7 Hz), 3.30 (3H, s), 3.21 (3H, s), 3.16 (3H, s), 2.19-2.09 (2H, m), 2.07 (3H, s). |
| 111* | 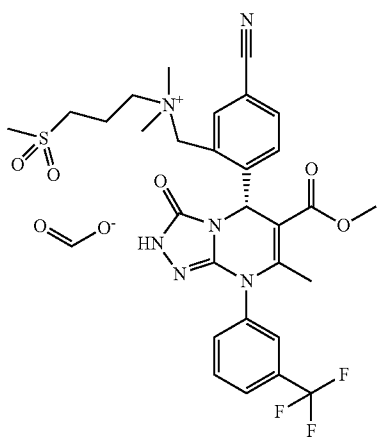 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-methanesulfonyl-propyl)-dimethyl-ammonium formate | Rt = 3.36 min, m/z = 633.2 [M]+ | ¹H NMR (400 MHz, DMSO) δ 11.63 (1H, bs), 8.53 (1H, s, formate), 8.12 (1H, d, J = 1.6 Hz), 8.11 (1H, bs), 8.03 (1H, dd, J = 8.2, 1.6 Hz), 7.95-7.79 (4H, m), 6.49 (1H, s), 5.15 (1H, d, J = 14 Hz), 5.04 (1H, d, J = 14 Hz), 3.69-3.61 (2H, m), 3.55 (3H, s), 3.28-3.19 (8H, m), 3.06 (3H, s), 2.35-2.22 (2H, m), 2.07 (3H, s). |
| 112 | 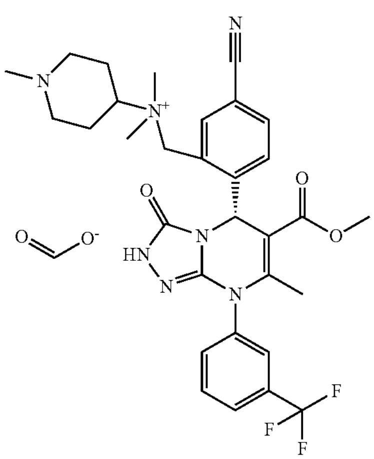 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(1-methyl-piperidin-4-yl)-ammonium formate | Rt = 2.76 min, m/z = 610.2 [M]+ | ¹H NMR (400 MHz, DMSO) δ 11.47 (1H, bs), 8.37 (2H, s, formate), 8.11 (1H, d, J = 1.7 Hz), 8.09 (1H, bs), 8.02 (1H, dd, J = 8.2, 1.7 Hz), 7.95-7.91 (1H, m), 7.90-7.74 (3H, m), 6.36 (1H, s), 5.18 (1H, d, J = 14.2 Hz), 4.86 (1H, d, J = 14.2 Hz), 3.76-3.66 (2H, m), 3.53 (3H, s), 3.18 (3H, s), 3.09-2.99 (2H, m), 3.05 (3H, s), 2.31-2.24 (2H, m), 2.22 (3H, s), 2.09 (3H, s), 2.04-1.87 (3H, m). |

| Example | Structure | Name | LC-MS (Method 3) | NMR |
|---|---|---|---|---|
| 113 | 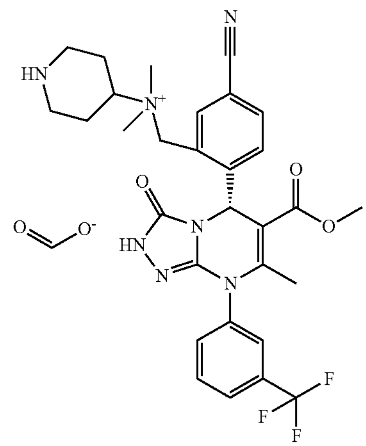 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-piperidin-4-yl-ammonium formate | Rt = 2.79 min, m/z = 596.2 [M]+ | $^1$H NMR (400 MHz, DMSO) δ 11.48 (1H, bs), 8.35 (2H, s, formate), 8.12 (1H, d, J = 1.6 Hz), 8.09 (1H, bs), 8.02 (1H, dd, J = 8.2, 1.7 Hz), 7.95-7.91 (1H, m), 7.90-7.79 (3H, m), 6.36 (1H, s), 5.13 (1H, d, J = 14.3 Hz), 4.85 (1H, d, J = 14.3 Hz), 3.85-3.75 (3H, m, obscured), 3.53 (2H, s, obscured), 3.24-3.17 (2H, m), 3.15 (3H, s), 3.03 (3H, s), 2.60-2.53 (2H, m, obscured), 2.29-2.20 (2H, m), 2.09 (3H, s), 1.82-1.65 (2H, m). |
| 114 | 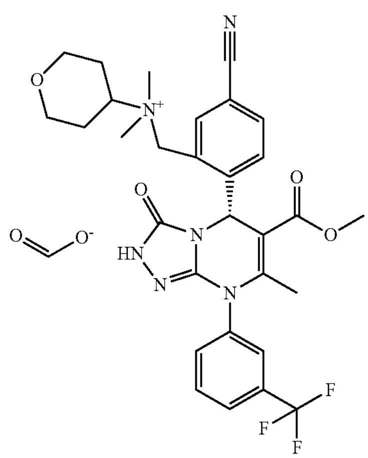 | {5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(tetrahydro-pyran-4-yl)-ammonium formate | Rt = 3.41 min, m/z = 597.2 [M]+ | $^1$H NMR (400 MHz, DMSO) δ 11.56 (1H, bs), 8.42 (1.5H, s, formate), 8.13 (1H, d, J = 1.8 Hz), 8.09 (1H, bs), 8.03 (1H, dd, J = 8.4, 1.8 Hz), 7.95-7.91 (1H, m), 7.90-7.79 (3H, m), 6.37 (1H, s), 5.18 (1H, d, J = 14.2 Hz), 4.87 (1H, d, J = 14.0 Hz), 4.17-4.09 (2H, m), 4.06-3.97 (1H, m), 3.54 (3H, s), 3.42 (2H, t, J = 11.6 Hz), 3.19 (3H, s), 3.05 (3H, s), 2.25 (2H, t, J = 11 Hz), 2.09 (3H, s), 2.05-1.89 (2H, m). |
| 115 | 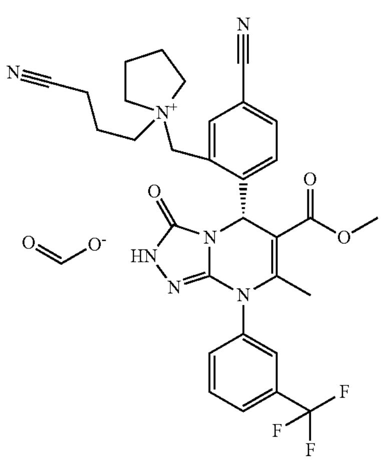 | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-(3-cyano-propyl)-pyrrolidinium formate | Rt = 3.52 min, m/z = 606.3 [M]+ | $^1$H NMR (400 MHz, DMSO) δ 11.50 (1H, bs), 8.44 (1.4H, s, formate), 8.14-8.06 (2H, m), 8.02-7.97 (1H, m), 7.95-7.79 (4H, m), 6.35 (1H, s), 5.21-5.07 (2H, m), 3.93-3.75 (4H, m), 3.62-3.53 (5H, m, obscured), 2.66 (2H, t, J 7.3 Hz), 2.29-2.14 (2H, m), 2.12-2.02 (7H, s). |

\*= for tertiary amine preparations see Intermediates 27-32.

Example 116

1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium bromide

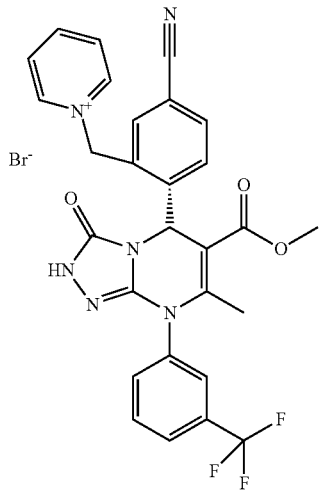

A solution of Intermediate 14 (1.30 g, 2.37 mmol) in MeCN (10 mL) was treated with pyridine (1.91 mL, 23.72 mmol) and warmed to 50° C. for 3 hours. The resultant mixture was concentrated in vacuo and the crude product partitioned between water (30 mL) and EtOAc (25 mL) and the aqueous layer separated and lypholised to give the desired product as a white electrostatic solid.

LC-MS (Method 3): Rt=3.42 min, m/z=547.2 [M]$^+$ $^1$H NMR (400 MHz, DMSO) δ 11.39 (1H, bs), 9.35 (2H, d, J=6.4 Hz), 8.69 (1H, t, J=7.8 Hz), 8.24 (2H, m), 8.18 (1H, bs), 8.04-7.89 (3H, m), 7.88-7.79 (2H, m), 7.79-7.75 (1H, m), 6.56 (1H, d, J=15.3 Hz), 6.42 (1H, s), 6.14 (1H, d, J=15.1 Hz), 3.55 (3H, s) and 2.18 (3H, s).

The following compounds were prepared from Intermediate 14 using an analogous method to that used for Example 116, utilising an appropriate acid to prepare the desired IRA-458 resin (see Example 42 for the quat exchange method), and gave the desired compounds as a white electrostatic solids.

| Example | Structure | Name | LC-MS (Method 3) | NMR |
|---|---|---|---|---|
| 117 | 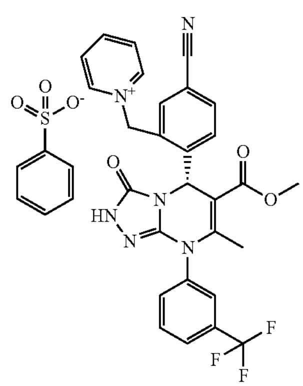 [SMILES: O=S(=O)([O-])c1ccccc1 ; COC(=O)C1=C(C)N(c2cccc(C(F)(F)F)c2)c2n[nH]c(=O)n2[C@@H]1c1ccc(C#N)cc1C[n+]1ccccc1] | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium benzenesulphonate | Rt = 3.40 min, m/z = 547.2 [M]$^+$ | $^1$H NMR (400 MHz, DMSO) δ 11.40 (1H, bs), 9.35 (2H, d, J = 6.6 Hz), 8.69 (1H, t, J = 7.8 Hz), 8.26-8.21 (2H, m), 8.17 (1H, bs), 8.00-7.89 (3H, m), 7.88-7.79 (2H, m), 7.78-7.74 (1H, m), 7.62-7.57 (2H, m, besylate), 7.34-7.27 (3H, m, besylate), 6.56 (1H, d, J = 15.1 Hz), 6.42 (1H, s), 6.13 (1H, d, J = 15.1 Hz), 3.54 (3H, s) and 2.18 (3H, s). |
| 118 | 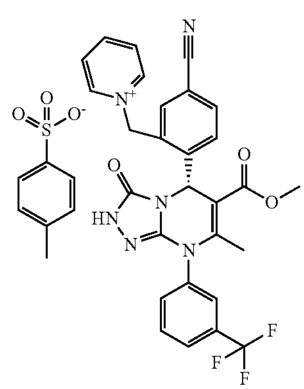 [SMILES: Cc1ccc(S(=O)(=O)[O-])cc1 ; COC(=O)C1=C(C)N(c2cccc(C(F)(F)F)c2)c2n[nH]c(=O)n2[C@@H]1c1ccc(C#N)cc1C[n+]1ccccc1] | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium tosylate | Rt = 3.43 min, m/z = 547.2 [M]$^+$ | $^1$H NMR (400 MHz, DMSO) δ 11.39 (1H, bs), 9.34 (2H, d, J = 6.7 Hz), 8.69 (1H, t, J = 7.8 Hz), 8.26-8.20 (2H, m), 8.17 (1H, bs), 8.00-7.89 (3H, m), 7.88-7.79 (2H, m), 7.78-7.74 (1H, m), 7.47 (2H, d, J = 8.1 Hz, tosylate), 7.11 (2H, d, J = 8.1 Hz, tosylate), 6.56 (1H, d, J = 15.2 Hz), 6.42 (1H, s), 6.13 (1H, d, J = 15.2 Hz), 3.54 (3H, s), 2.29 (3H, s) and 2.18 (3H, s). |

| Example | Structure | Name | LC-MS (Method 3) | NMR |
|---|---|---|---|---|
| 119 | 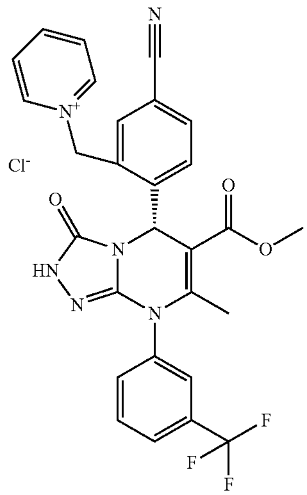 [SMILES: COC(=O)C1=C(C)N(c2cccc(C(F)(F)F)c2)c2n[nH]c(=O)n2[C@@H]1c1ccc(C#N)cc1C[n+]1ccccc1 ; [Cl-]] | 1-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium chloride | Rt = 3.42 min, m/z = 547.2 [M]⁺ | ¹H NMR (400 MHz, DMSO) δ 11.41 (1H, bs), 9.36 (2H, d, J = 6.3 Hz), 8.68 (1H, tt, J = 7.8, 1.3 Hz), 8.24 (2H, dd, J = 7.6, 6.7 Hz), 8.16 (1H, bs), 7.96-7.90 (3H, m), 7.83 (2H, t, J = 7.8 Hz), 7.70 (1H, d, J = 1.5 Hz), 6.56 (1H, d, AB-system, J = 15.2 Hz), 6.42 (1H, s), 6.15 (1H, d, AB-system, J = 15.1 Hz), 3.54 (3H, s), 2.18 (3H, s). |

Example 120

Benzyl-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-ammonium bromide

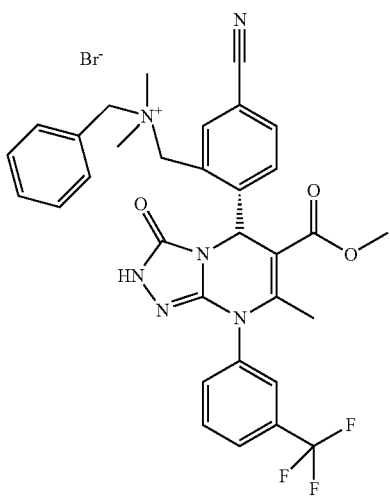

N-benzyl dimethylamine (1.80 mL, 12.0 mmol) was added to a solution of Intermediate 14 (1.26 g, 2.36 mmol) in MeCN (8 mL) and toluene (4 mL) contained in a large microwave vial. This was sealed and heated at 50° C. with stirring for 21 hours. Solvents were removed in vacuo and the resultant green residue triturated with Et₂O. The organics were decanted off and the residue slurried in EtOAc (50 mL) for 1 hour then filtered and dried in vacuo to afford an off-white solid. The resultant solid was partitioned between water and a [1:1] mixture of EtOAc/Et₂O and the hazy aqueous phase was separated, purged with a stream of air to remove volatile solvent residues. MeCN (25 mL) was added and the resulting solution was lyophilised to afford the title compound as a cream coloured electrostatic solid (0.66 g).

LC-MS (Method 3): Rt=3.72 min, m/z=603.4 [M]⁺

¹H NMR (400 MHz, DMSO) δ 11.36 (1H, bs), 8.17 (1H, d, J=1.6 Hz), 8.11 (1H, bs), 8.04 (1H, dd, J=1.6, 8.3 Hz), 7.95-7.85 (3H, m), 7.84-7.78 (1H, m), 7.66-7.60 (2H, m), 7.58-7.51 (3H, m), 6.50 (1H, s), 5.27 (1H, d, J=14.5 Hz), 5.03 (1H, d, J=14.1 Hz), 4.87 (1H, d, J=12.4 Hz), 4.75 (1H, d, J=12.4 Hz), 3.50 (3H, s) 3.14 (3H, s), 3.12 (3H, s) and 2.08 (3H, s).

Example 121

Benzyl-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-ammonium benzenesulfonate

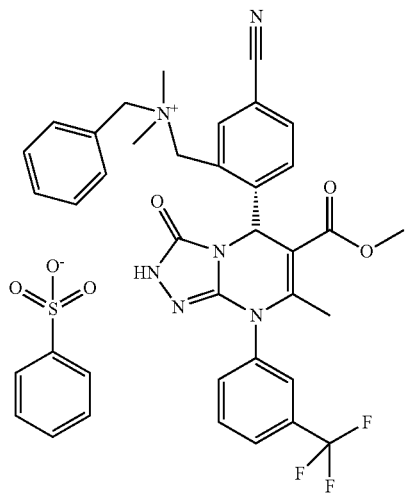

The title compound was prepared from Example 120 (0.53 g, 0.77 mmol) using an analogous method to that used for Example 42 and gave the desired compound as a white electrostatic solid. This was suspended in water (5.0 mL) with warming at 45° C., then cooled to RT, filtered and dried in vacuo to afford the title compound as a white solid (0.32 g).

LC-MS (Method 3): Rt=3.69 min, m/z=603.2 [M]+

$^1$H NMR (400 MHz, DMSO) δ 11.36 (1H, bs), 8.17 (1H, d, J=1.6 Hz), 8.10 (1H, bs), 8.04 (1H, dd, J=1.6, 8.3 Hz), 7.95-7.85 (3H, m), 7.84-7.78 (1H, m), 7.66-7.51 (7H, m), 7.34-7.26 (3H, m), 6.49 (1H, s), 5.26 (1H, d, J=14.5 Hz), 5.02 (1H, d, J=14.1 Hz), 4.86 (1H, d, J=12.4 Hz), 4.74 (1H, d, J=12.4 Hz), 3.50 (3H, s) 3.14 (3H, s), 3.11 (3H, s) and 2.08 (3H, s).

Example 122

4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-morpholin-4-ium bromide

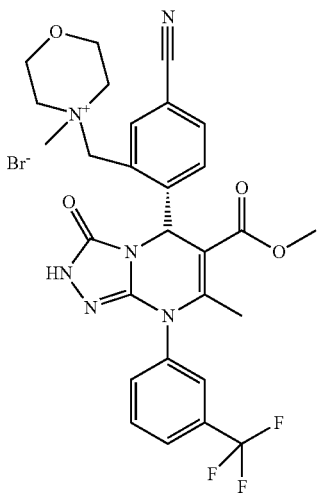

The title compound was prepared from Intermediate 14 (1.20 g, 2.19 mmol) using an analogous method to that used for Example 120. The semi-pure solid product was further stirred in EtOAc (30 mL) at 40° C. for 2 hours and sonicated for 5 minutes. The resultant solid was filtered to give a beige cake, which was dissolved in MeCN/H$_2$O (10 mL) and lyophilised to give the title compound as an off-white electrostatic solid (0.43 g).

LC-MS (Method 3): Rt=3.33 min, m/z=569.2 [M]+

$^1$H NMR (400 MHz, DMSO-D$_6$) δ 11.36 (1H, s), 8.15-8.08 (2H, m), 8.04 (1H, dd, J=8.2, 1.7 Hz), 7.95-7.79 (4H, m), 6.55 (1H, s), 5.24 (1H, d J=14.1 Hz), 5.11 (1H, d, J=14.1 Hz), 4.10-3.92 (4H, m), 3.91-3.79 (2H, m), 3.64-3.54 (2H, m, obscured), 3.54 (3H, s), 3.28 (3H, s) and 2.07 (3H, s).

Example 123

4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-morpholin-4-ium bromide

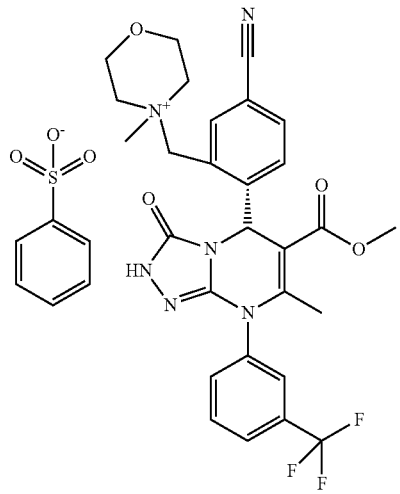

The title compound was prepared from Example 122 (0.47 g, 0.72 mmol) using an analogous method to that used for Example 42. The semi-pure solid product was further purified by HPLC (System 1) and was then lyophilised to give the title compound as a white electrostatic solid (0.23 g).

LC-MS (Method 3): Rt=3.33 min, m/z=569.2 [M]+

$^1$H NMR (400 MHz, DMSO-D$_6$) δ 11.36 (1H, s), 8.14-8.08 (2H, m), 8.03 (1H, dd, J=8.2, 1.8 Hz), 7.95-7.78 (4H, m), 7.62-7.57 (2H, m, besylate), 7.34-7.27 (3H, m, besylate), 6.54 (1H, s), 5.22 (1H, d J=14.2 Hz), 5.10 (1H, d, J=14.2 Hz), 4.09-3.91 (4H, m), 3.91-3.79 (2H, m), 3.64-3.54 (2H, m, obscured), 3.54 (3H, s), 3.27 (3H, s) and 2.07 (3H, s).

Example 124

4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-morpholin-4-ium bromide

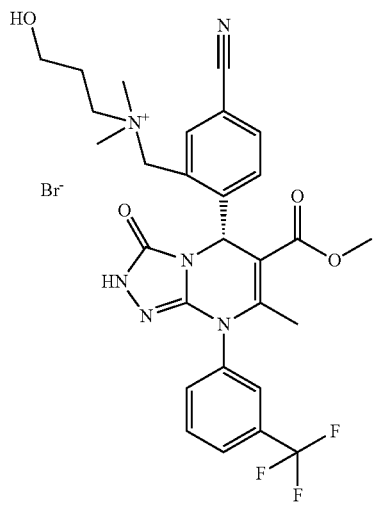 [SMILES: COC(=O)C1=C(C)N(c2cccc(C(F)(F)F)c2)c2n[nH]c(=O)n2[C@@H]1c1ccc(C#N)cc1C[N+](C)(C)CCCO ; [Br-]]

The title compound was prepared from Intermediate 14 (0.76 g, 1.38 mmol) using an analogous method to that used for Example 120. A C$_{18}$ Isolute cartridge (50 g) was preconditioned by elution with MeCN (150 mL) followed by 75%-0.5% MeCN in 0.01M aqueous HBr (100 mL). The crude product (650 mg) was dissolved in 0.5% MeCN: 0.01M HBr (10 mL), loaded onto the cartridge and eluted from 0.5%-40% MeCN in 0.01M aqueous HBr. The title compound was obtained as an electrostatic solid following lyophilisation (0.42 g).

LC-MS (Method 3): Rt=3.26 min, m/z=571.2 [M]+

$^1$H NMR (400 MHz, DMSO-D$_6$) δ 11.36 (1H, bs), 8.14 (1H, d, J=1.6 Hz), 8.11 (1H, bs), 8.02 (1H, dd, J=8.1, 1.5 Hz). 7.95-7.78 (4H, m), 6.49 (1H, s), 5.12 (1H, d, J=14.0 Hz), 4.97 (1H, d, J=14.0 Hz), 3.68-3.60 (2H, m), 3.59-3.53 (2H, m, obscured), 3.53 (3H, s), 3.22 (3H, s), 3.17 (3H, s), 2.07 (3H, s) and 2.07-1.97 (2H, m), OH not observed.

Example 125

4-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-morpholin-4-ium bromide

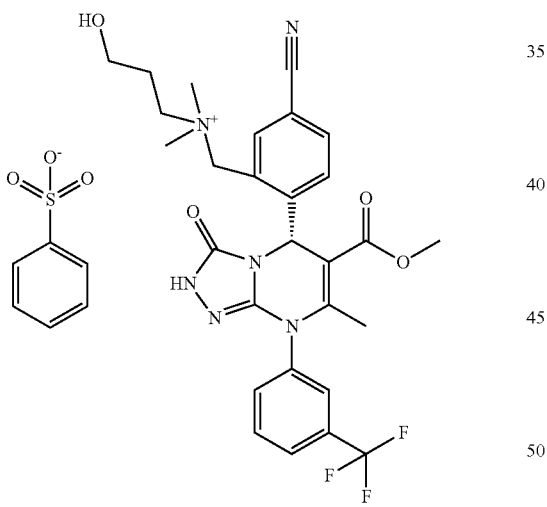

The title compound was prepared from Example 124 (0.72 g, 1.31 mmol) using an analogous method to that used for Example 42. The semi-pure solid product was further purified by HPLC (System 1) and was then lyophilised to give the title compound as a white electrostatic solid (0.23 g).

LC-MS (Method 3): Rt=3.27 min, m/z=571.3 [M]+

$^1$H NMR (400 MHz, DMSO-D$_6$) δ 11.36 (1H, bs), 8.12 (1H, d, J=1.6 Hz), 8.10 (1H, bs), 8.02 (1H, dd, J=8.2, 1.6 Hz). 7.95-7.78 (4H, m), 7.62-7.57 (2H, m, besylate), 7.34-7.27 (3H, m, besylate), 6.48 (1H, s), 5.11 (1H, d, J=14.0 Hz), 4.96 (1H, d, J=14.0 Hz), 4.85 (1H, bs), 3.68-3.60 (2H, m), 3.59-3.53 (2H, m, obscured), 3.53 (3H, s), 3.21 (3H, s), 3.16 (3H, s), 2.07 (3H, s) and 2.07-1.97 (2H, m).

Example 126

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium benzenesulfonate

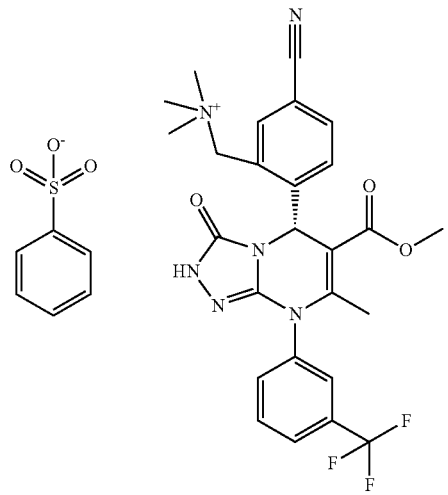

The title compound was prepared from Example 9 (0.85 g, 1.37 mmol) using an analogous method to that used for Example 42. The semi-pure solid product was further purified by HPLC (System 1) and was then lyophilised to give the title compound as a white electrostatic solid (0.90 g).

LC-MS (Method 3): Rt=3.27 min, m/z=571.3 [M]+

$^1$H NMR (400 MHz, DMSO-D$_6$) δ 11.36 (1H, bs), 8.12 (1H, d, J=1.6 Hz), 8.10 (1H, bs), 8.02 (1H, dd, J=8.2, 1.6 Hz). 7.95-7.78 (4H, m), 7.62-7.57 (2H, m, besylate), 7.34-7.27 (3H, m, besylate), 6.48 (1H, s), 5.11 (1H, d, J=14.0 Hz), 4.96 (1H, d, J=14.0 Hz), 4.85 (1H, bs), 3.68-3.60 (2H, m), 3.59-3.53 (2H, m, obscured), 3.53 (3H, s), 3.21 (3H, s), 3.16 (3H, s), 2.07 (3H, s) and 2.07-1.97 (2H, m).

Example 127

{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-bis-(2-hydroxy-ethyl)-methyl-ammonium benzenesulfonate

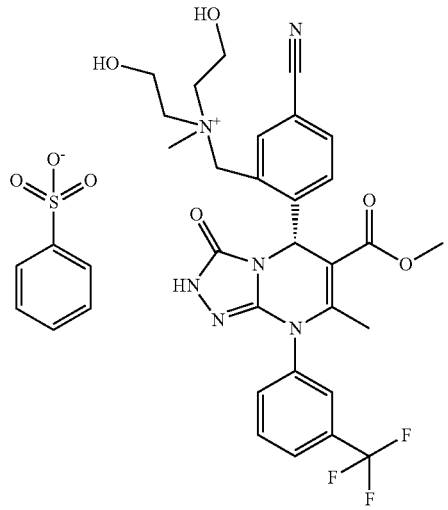 [SMILES: O=S(=O)([O-])c1ccccc1 ; COC(=O)C1=C(C)N(c2cccc(C(F)(F)F)c2)c2n[nH]c(=O)n2[C@@H]1c1ccc(C#N)cc1C[N+](C)(CCO)CCO]

The title compound was prepared from Example 107 (0.60 g, 0.95 mmol) using an analogous method to that used for Example 42 and gave the title compound as a white electrostatic solid (0.54 g).

LC-MS (Method 3): Rt=3.28 min, m/z=587.2 [M]$^+$ $^1$H NMR (400 MHz, DMSO-D$_6$) δ 1H NMR (400 MHz, DMSO) δ 11.36 (1H, bs), 8.23-8.18 (1H, m), 8.11 (1H, bs), 8.03-7.98 (1H, m), 7.95-7.78 (4H, m), 7.61-7.56 (2H, m, besylate), 7.34-7.27 (3H, m, besylate), 6.50 (1H, s), 5.47-5.39 (2H, m, 2×OH), 5.30-5.13 (2H, m), 4.06-3.79 (6H, m), 3.72-3.62 (2H, m), 3.53 (3H, s), 3.23 (3H, s), 2.05 (3H, s).

Route B to Intermediate 4b (S)-5-(2-Bromo-4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester

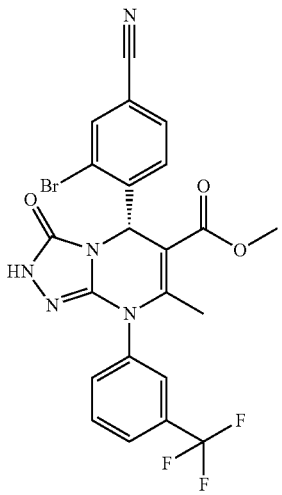

(4b)

Intermediate 33

3-Bromo-4-dibromomethylbenzoic acid

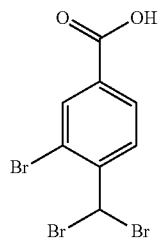

3-Bromo-4-methylbenzoic acid (910 g, 4.23 mol, 1.0 eq.) and NBS (2010 g, 11.29 mol, 2.67 eq.) were dissolved in DCM (8.5 L) in a 20 L flange flask fitted with a mechanical stirrer. A slurry of AIBN (50 g, 0.3 mol, 0.07 eq.) in DCM (1 L) was then added, and the mixture irradiated under strong light (500 W) under a reflux condenser under an N$_2$ atmosphere. The internal temperature of the reaction rose from 17° C. to 41° C. and the initial white suspension became a pale orange suspension as it reached gentle reflux. After a total of 72 hours, the reaction was complete and water (5 L) was added to the cloudy orange solution, which was stirred at RT for 1 hour. The orange biphasic mixture was then left to stand overnight and was then concentrated in vacuo to give an orange distillate and a tan suspended solid. The solid was then collected by filtration, washed with water (2 L) and suction dried for 2 h to give the title compound as a tan coloured damp solid (1860 g).

LCMS (Method 1): Rt=3.39 min, m/z 369, 371, 373, 375 [M−H]

$^1$H NMR (300 MHz, DMSO): δ 8.14-8.03 (3H, m), 7.36 (1H, s).

Intermediate 34

3-Bromo-4-formylbenzoic acid

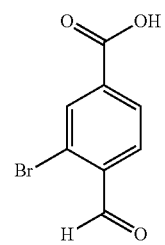

Intermediate 33 (1860 g, 4.23 mol, 1.0 eq.) was suspended in water (5 L) and the slurry was heated to an internal temperature of 40° C. Solid Na$_2$CO$_3$ (1460 g, 13.77 mol, 3.25 eq.) was then added in small portions over a period of 20 minutes. Foaming resulted on initial addition, so EtOAc (0.2 L) was added to collapse the foam and suppress any further foaming. Once addition was complete, the brown suspension was heated to 90° C. over 40 minutes, then stirred at 90° C. for 90 minutes, then cooled to 40° C. over 90 minutes. EtOAc (1.5 L) was added, followed by addition of aqueous concentrated HCl via dropping funnel (0.7 L), resulting in vigorous evolution of CO$_2$ gas and evaporation of most of the EtOAc. Further EtOAc (1 L) was added to wash the foaming product from the condenser and the walls of the reactor, then additional EtOAc (0.3 L) was added and the thick slurry was stirred at RT overnight. The slurry was then heated to 40° C. and further aqueous concentrated HCl was added via dropping funnel with vigorous stirring over 45 minutes, resulting in CO$_2$ gas evolution, evaporation of most of the EtOAc and formation of a solid. Stirring was ceased, and the solid floated to the top of the aqueous mixture (pH 1). The majority of the aqueous layer was separated (ca. 5 L) and then 2-MeTHF (5 L) was added. The clear aqueous layer was then removed, and the organic layer diluted to 10 L with additional 2-MeTHF, and warmed to 50° C. to give a dark orange solution. The organic layer was then washed with 1 M HCl (0.5 L), evaporated, and azeotroped with toluene to afford the title compound as a tan coloured solid (960.3 g).

LCMS (Method 4): Rt 2.73 min, m/z 227, 229 [M−H]

$^1$H NMR (300 MHz, DMSO): δ 10.26 (1H, d, J=0.8 Hz), 8.20 (1H, d, J=1.5 Hz), 8.08-8.04 (1H, m), 7.95 (1H, d, J=8.0 Hz).

Intermediate 35

4-(2-Bromo-4-carboxyphenyl)-6-methyl-2-thioxo-1-(3-trifluoromethylphenyl)-1,2,3,4-tetrahydropyrimidine-5-carboxylic acid methyl ester

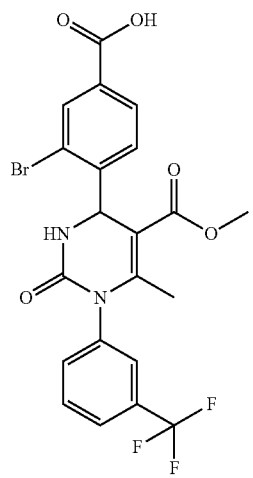 [SMILES: COC(=O)C1=C(C)N(c2cccc(C(F)(F)F)c2)C(=S)N[C@@H]1c1ccc(C(=O)O)cc1Br]

Intermediate 34 (458 g, 2 mol, 1.0 eq.), methyl acetoacetate (274.4 g, 255 mL, 2.36 mol, 1.18 eq.) and 3-trifluoromethylphenyl thiourea (519 g, 2.36 mol, 1.18 eq.), were charged to a 10 L jacketed reactor under a $N_2$ atmosphere, and suspended in THF (4.6 L) and while stirring, was cooled to −10° C. (internal temperature −3° C.). Polyphosphoric acid (1650 g, 3.6 wt eq.), was prewarmed in a water bath at 50° C., then added in one portion, resulting in an immediate exotherm, and the internal temperature rose to 19° C. The resulting orange mixture was then warmed to 75° C. in 10° C. increments to a gentle reflux, and the reaction stirred at this temperature for 20 hours. The reaction was then cooled to 20° C. and the bulk of THF removed in vacuo to give a dark orange viscous oil, which was then diluted with water (5 L) and $Et_2O$ (5 L). The aqueous layer was separated and extracted again with $Et_2O$ (2×2 L) and the combined organics were subsequently washed with water (1 L), brine (1 L) and dried ($Na_2SO_4$) and filtered through Celite to remove any fine particulates. The filtered solution was then concentrated in vacuo to give a viscous orange gum which was resuspended in $Et_2O$ (ca. 1.5 L) and left to stand overnight. The resulting suspension was filtered and the solid collected was rinsed with $Et_2O$ (0.5 L) and dried in a vacuum oven at 50° C. (8 mbar) for 4 days to afford the title compound (754 g).

LCMS (Method 1): Rt 3.52 min, m/z 529, 531 [M+H]$^+$ $^1$H NMR (300 MHz, DMSO): δ 10.15 (1H, d, J=3.5 Hz), 8.11 (1H, d, J=1.6 Hz), 8.05 (1H, dd, J=8.1, 1.7 Hz), 7.92-7.64 (5H, m), 5.80 (1H, d, J=2.9 Hz), 3.53 (3H, s), 2.07 (3H, s).

Intermediate 36

(S)-4-(2-Bromo-4-carboxy-phenyl)-6-methyl-2-thioxo-1-(3-trifluoromethyl-phenyl)-1,2,3,4-tetrahydro-pyrimidine-5-carboxylic acid methyl ester

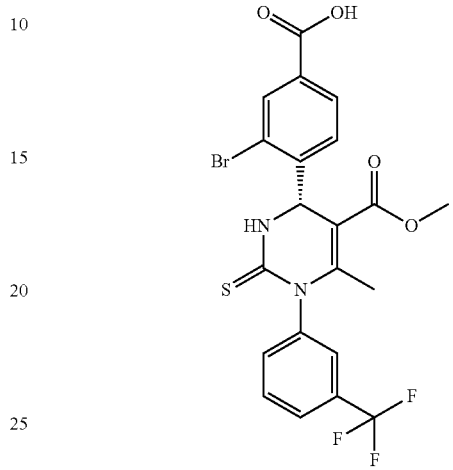

Intermediate 35 (151.7 g, 0.29 mol, 1.0 eq.) was dissolved in dioxane (2 L) and heated to 80° C. The resulting suspension was filtered to remove any inorganic residues and the clear solution was again heated to 80° C. and (+)-Cinchonine (88 g, 0.29 mol, 1.0 eq,) was added, resulting in a clear solution. The resultant mixture was allowed to cool slowly and crystallise. After 3 hours, the resulting solid was filtered and washed with cold dioxane. The solid was resuspended in hot dioxane (85° C.) and allowed to cool and crystallise overnight. The resulting crystals were filtered off, washed with cold dioxane, and the solid recrystallized again from hot dioxane. The final recrystallization solids were filtered off and air-dried to give the intermediate (+)-Cinchonine salt as a white solid 83.2 g (68%).

The optical purity of the resolved (+)-Cinchonine salt was determined by partitioning between 1 M HCl and EtOAc; the organic layer was separated, concentrated in vacuo and then redissolved in 20% IPA/n-heptane with 0.1% TFA and subjected to chiral analytical HPLC (ChiralPak IA, 5 μM 4.6× 250 mm), eluting with 20% IPA/n-heptane (+0.1% TFA) at 1 mL/min and a wavelength of 254 nm. The racemic product was also checked by chiral HPLC; Retention times of 14.8 and 42.5 mins were observed for a racemic sample and the desired enantiomer was eluted at 42.5 mins and was found to be greater than 99.5 ee %.

The intermediate (+)-Cinchonine salt (83.2 g, 101.75 mmol) was liberated by partitioning between EtOAc (1 L) and 1 M HCl (1 L). The aqueous layer was extracted again with EtOAc (2×0.5 L) and the combined organic layers washed with 1 M HCl (0.5 L), then brine (0.25 L), dried ($Na_2SO_4$) and concentrated in vacuo to give the title compound as a white solid (45.45 g).

Intermediate 37

(S)-4-(2-Bromo-4-carbamoyl-phenyl)-6-methyl-2-thioxo-1-(3-trifluoromethyl-phenyl)-1,2,3,4-tetrahydro-pyrimidine-5-carboxylic acid methyl ester

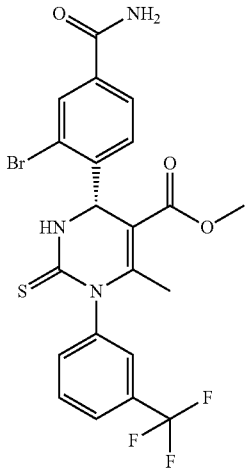 [SMILES: COC(=O)C1=C(C)N(c2cccc(C(F)(F)F)c2)C(=S)N[C@@H]1c1ccc(C(N)=O)cc1Br]

Intermediate 36 (93.8 g, 0.18 mol) was dissolved in THF (1 L) and 1,1'-carbonyldiimidazole (57.5 g, 0.35 mol, 2.0 eq.) was added portion-wise and left to stir at RT until gas evolution had ceased. Aqueous ammonia solution (33%, 330 mL) was then added drop-wise, ensuring the internal temperature did not exceed 10° C. (exotherm observed on initial addition). The reaction was left to stir at RT for 2 hours, then brine was added and the layers were separated. The organic phase was washed with aqueous 1 M HCl (2×) and the acidic layer further extracted with EtOAc. The combined organic layers were washed with brine, dried ($Na_2SO_4$), filtered and concentrated in vacuo to afford the title compound as a colorless foam (87.3 g).

LCMS (Method 2): Rt 3.44 min, m/z 528, 530 $[M+H]^+$ $^1$H NMR (300 MHz, DMSO): δ 10.12 (1H, d, J=2.6 Hz), 8.12 (1H, s), 8.11 (1H, d, J=1.7 Hz), 7.96 (1H, dd, J=8.1, 1.7 Hz), 7.88-7.77 (2H, m), 7.75-7.63 (3H, m), 7.54 (1H, s), 5.78 (1H, s), 3.54 (3H, s), 2.07 (3H, s).

Intermediate 38

(S)-4-(2-Bromo-4-cyanophenyl)-6-methyl-2-thioxo-1-(3-trifluoromethylphenyl)-1,2,3,4-tetrahydropyrimidine-5-carboxylic acid methyl ester

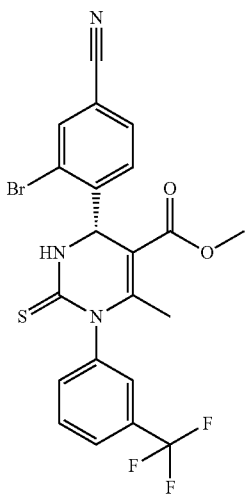 [SMILES: COC(=O)C1=C(C)N(c2cccc(C(F)(F)F)c2)C(=S)N[C@@H]1c1ccc(C#N)cc1Br]

Intermediate 37 (87.3 g, 0.165 mol) was dissolved in DMF (400 mL) and cooled to 0-5° C. in an ice bath. Phosphorous oxychloride (62.0 g, 37.0 mL, 2.5 eq.) was then added dropwise, ensuring the internal temperature did not exceed 10° C. Once addition was complete, the yellow solution was stirred at 0-5° C. for 15 minutes, then poured into a mixture of solid 2 M $Na_2CO_3$ and ice. A yellow precipitate formed and the slurry was aged for 1 hour, then the solid was filtered, washed with water and dried in a vacuum oven over $P_2O_5$ at 40-45° C. NMR analysis of the resultant product still showed starting material remaining so the reaction was repeated again using a further 20 mL phosphorous oxychloride. NMR of the resulting solid showed the product to be an adduct with $POCl_3$.

Therefore, the solid was dissolved in absolute EtOH (1000 mL) and the suspension warmed to aid dissolution. Saturated aqueous $NaHCO_3$ solution (250 mL) was then added and the mixture was heated to 40° C. and stirred for 2 hours. The resultant mixture was then poured into water (500 mL) and the resulting white solid filtered off, washed with water and air dried to afford the title compound (77.5 g).

LCMS (Method 2): Rt 3.94 min, m/z 510, 512 $[M+H]^+$ $^1$H NMR (300 MHz, DMSO): δ 10.18 (1H, d, J=2.7 Hz), 8.24 (1H, d, J=1.5 Hz), 7.96 (1H, dd, J=8.0, 1.6 Hz), 7.89-7.76 (3H, m), 7.74-7.64 (2H, m), 5.8 (1H, s), 3.53 (3H, s), 2.06 (3H, s).

(S)-5-(2-Bromo-4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester (Intermediate 4b)

Intermediate 38 (49.8 g, 98 mmol) was dissolved in DCM (830 mL), 2,6-lutidine (32.4 mL, 278 mmol, 2.85 eq.) was added and the solution was cooled to 2° C. While stirring, triphosgene (9.17 g, 30.9 mmol, 0.32 eq) was then added slowly over a period of 3 minutes. After 5 minutes, the reaction was warmed to RT and stirred for 25 minutes. The reaction was cooled to 8° C. and the solution was then transferred via cannula to a cooled (7° C.) mixture of hydrazine solution (1 M in THF, 278 mL) and MeCN (250 mL). The reaction was stirred at 7° C. for a further 10 minutes and then allowed to warm to RT. After 2.25 hours, the reaction mixture was washed with water, then with 50% saturated brine and the organic phase was dried ($Na_2SO_4$), filtered and concentrated in vacuo. The resulting gum was azeotroped with toluene and triturated with $Et_2O$ (200 mL) to afford a solid which was filtered off, washed with $Et_2O$ and dried to afford the title compound as a cream coloured solid (31.75 g).

LCMS (Method 5): Rt 3.51 min, m/z 534, 536 $[M+H]^+$ $^1$H NMR (300 MHz, $CDCl_3$): δ 8.36 (1H, s), 7.88 (1H, d, J=1.5 Hz), 7.83-7.79 (1H, m), 7.73 (1H, t, J=8.0 Hz), 7.65-7.60 (2H, m), 7.59-7.50 (2H, m), 6.39 (1H, d, J=1.0 Hz), 3.62 (3H, s), 2.25 (3H, d, J=1.0 Hz).

The chiral purity was analysed by Chiralpak IC chiral HPLC column (5 μm particle size, 5% MeOH/DCM, flow rate 5 mL/min) and gave Rt=5.83 minutes. (100% ee). A racemic sample (Intermediate 4) gave Rt for first and second eluting enantiomers of 3.58 and 5.85 minutes, respectively.

The following compounds were prepared from Example 49 using an analogous method to that used for Example 42, utilising an appropriate acid to prepare the desired IRA-458 resin, and gave the desired compounds as white electrostatic solids.

| Example | Structure | Name | LC-MS (Method 3) | NMR |
|---|---|---|---|---|
| 128 | 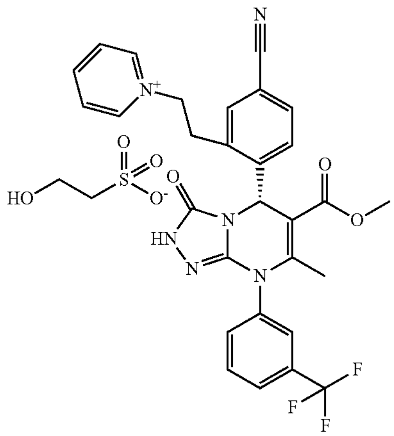 [SMILES: O=S(=O)([O-])CCO ; COC(=O)C1=C(C)N(c2cccc(C(F)(F)F)c2)c2n[nH]c(=O)n2[C@@H]1c1ccc(C#N)cc1CC[n+]1ccccc1] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium-2-hydroxy-ethanesulfonate | Rt = 3.48 min, m/z = 561.2 [M]$^+$ | $^1$HNMR (400 MHz, DMSO) δ 11.38 (1H, bs), 9.10 (2H, d, J = 5.6 Hz), 8.67 (1H, t, J = 7.7 Hz), 8.23 (2H, t, J = 7.2 Hz), 8.15 (1H, bs), 7.97-7.87 (2H, m), 7.86-7.80 (1H, m), 7.79-7.70 (2H, m), 7.61 (1H, m), 6.43 (1H, s), 5.26-5.07 (2H, m), 4.45 (1H, t, J = 5.7 Hz), 3.97-3.84 (1H, m), 3.62 (2H, q, J = 6.6 Hz), 3.65-3.52 (1H, m, obscured), 3.49 (3H, s), 2.60 (2H, t, J = 6.8 Hz), 2.16 (3H, s). |
| 129 | 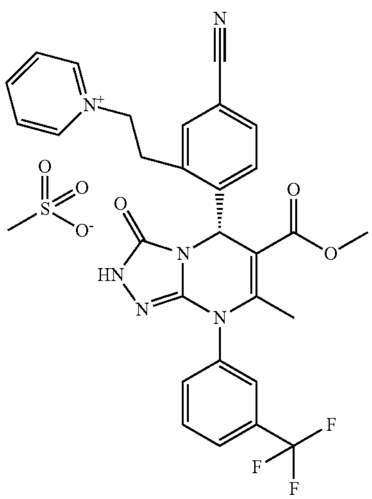 | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium methanesulfonate | Rt = 3.48 min, m/z = 561.2 [M]$^+$ | $^1$H NMR (400 MHz, DMSO) δ 11.39 (1H, bs), 9.10 (2H, d, J = 5.5 Hz), 8.67 (1H, t, J = 7.9 Hz), 8.23 (2H, t, J = 7.2 Hz), 8.15 (1H, bs), 7.97-7.87 (2H, m), 7.86-7.80 (1H, m), 7.79-7.70 (2H, m), 7.62 (1H, m), 6.43 (1H, s), 5.25-5.09 (2H, m), 3.97-3.84 (1H, m), 3.65-3.52 (1H, m), 3.49 (3H, s), 2.30 (3H, s), 2.16 (3H, s). |
| 130 | 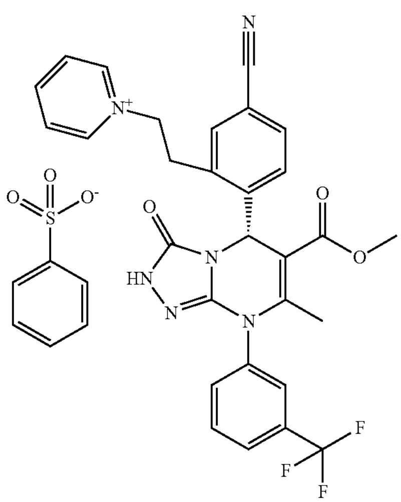 [SMILES: O=S(=O)([O-])c1ccccc1 ; COC(=O)C1=C(C)N(c2cccc(C(F)(F)F)c2)c2n[nH]c(=O)n2[C@@H]1c1ccc(C#N)cc1CC[n+]1ccccc1] | 1-(2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium benzenesulfonate | Rt = 3.50 min, m/z = 561.3 [M]$^+$ | $^1$H NMR (400 MHz, DMSO) δ 11.39 (1H, bs), 9.10 (2H, d, J = 5.5 Hz), 8.67 (1H, t, J = 7.9 Hz), 8.23 (2H, t, J = 7.2 Hz), 8.15 (1H, bs), 7.97-7.87 (2H, m), 7.86-7.80 (1H, m), 7.79-7.70 (2H, m), 7.62 (1H, m), 7.60-7.55 (2H, m, besylate), 7.35-7.27 (3H, m, besylate), 6.43 (1H, s), 5.25-5.09 (2H, m), 3.97-3.84 (1H, m), 3.65-3.52 (1H, m), 3.49 (3H, s), 2.30 (3H, s), 2.16 (3H, s). |

The following compounds (Examples 131 and 132) were prepared from Example 47 and Example 133 was prepared from Example 48, using an analogous method to that used for Example 42, utilising an appropriate acid to prepare the desired IRA-458 resin, and gave the desired compounds as white electrostatic solids.

| Example | Structure | Name | LC-MS (Method 3) | NMR |
|---|---|---|---|---|
| 131 | 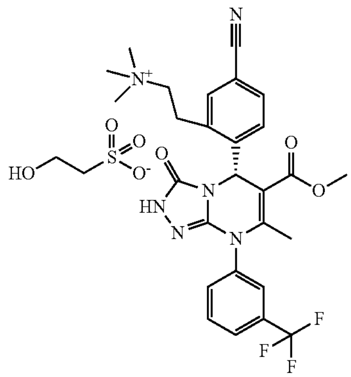 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium 2-hydroxy-ethanesulfonate | Rt = 3.45 min, m/z = 541.2 [M]+ | ¹H NMR (400 MHz, DMSO) δ 11.30 (1H, bs), 8.13 (1H, bs), 7.95-7.88 (2H, m), 7.85-7.80 (2H, m), 7.76 (1H, dd, J = 8.1, 1.7 Hz), 7.71 (1H, d, J = 8.1 Hz), 6.26 (1H, s), 4.44 (1H, t, J = 5.7 Hz, isoethionate), 4.01-3.93 (1H, m), 3.78-3.64 (2H, m), 3.62 (2H, dt, J = 6.7, 5.7 Hz, isoethionate), 3.53 (3H, s), 3.45-3.34 (1H, m), 3.21 (9H, s), 2.59 (2H, t, J = 6.7 Hz, isoethionate), 2.16 (3H, s). |
| 132 | 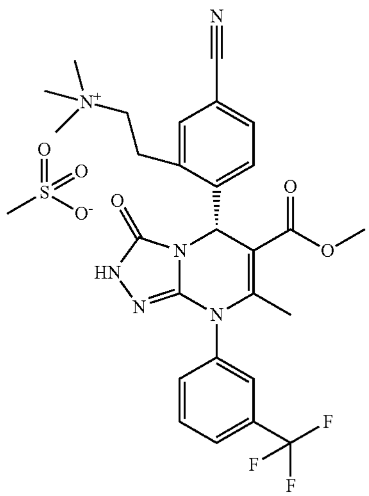 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium methanesulfonate | Rt = 3.42 min, m/z = 541.1 [M]+ | ¹H NMR (400 MHz, DMSO) δ 11.30 (1H, bs), 8.13 (1H, bs), 7.95-7.88 (2H, m), 7.85-7.80 (2H, m), 7.76 (1H, dd, J = 8.1, 1.7 Hz), 7.71 (1H, d, J = 8.1 Hz), 6.26 (1H, s), 4.01-3.93 (1H, m), 3.78-3.63 (2H, m), 3.53 (3H, s), 3.43-3.34 (1H, m), 3.21 (9H, s), 2.29, (3H, s, mesylate), 2.16 (3H, s). |
| 133 | 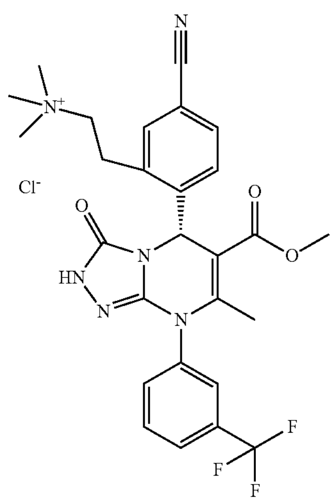 | (2-{5-Cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium chloride | Rt = 3.46 min, m/z = 541.2 [M]+ | ¹H NMR (400 MHz, DMSO) δ 11.32 (1H, bs), 8.13 (1H, bs), 7.95-7.88 (2H, m), 7.85-7.80 (2H, m), 7.76 (1H, dd, J = 8.1, 1.7 Hz), 7.71 (1H, d, J = 8.1 Hz), 6.26 (1H, s), 4.02-3.94 (1H, m), 3.79-3.63 (2H, m), 3.53 (3H, s), 3.43-3.36 (1H, m), 3.21 (9H, s), 2.16 (3H, s). |

Biological Assay.

Compounds of this invention were tested for potency in a human neutrophil elastase (HNE) enzyme activity assay.

HNE Enzyme Assay.

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 M. The final concentration of DMSO was 1% in the assay buffer (0.05M Tris.HCl, 0.1M NaCl, 0.1M CaCl$_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A dose response to each compound was performed and the effect of compound in each experiment was expressed as a percentage inhibition of the control enzyme fluorescence. Dose response curves were plotted and compound potency ($IC_{50}$) was determined. Compounds were tested in at least two separate experiments. $IC_{50}$s for tested Examples, representative of the invention, are shown in the following table:

| Example | HNE inhibition |
|---|---|
| 1-15, 17-20, 22, 24-40, 42-133 | ++++ |

In the table above, HNE enzyme inhibition ($IC_{50}$ values) are indicated as follows: >500 nM '+'; 100-500 nM '++'; 20-100 nM '+++'; <20 nM '++++'.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

(I)

wherein
A is CH;
B is CH;
D is CH;
$R_1$ is:
hydrogen;
$(C_1-C_6)$alkyl;
$NR_7R_8(C_1-C_6)$alkyl;
$(C_1-C_4)$alkenyl;
phenyl$(C_1-C_6)$alkyl wherein said phenyl ring is optionally substituted by a $NR_{15}R_{16}(C_1-C_6)$alkyl or by $N^+R_{15}R_{16}R_{17}(C_1-C_6)$alkyl;
a group —$CH_2(CH_2)_n$OH;
a group —$(CH_2)_n CONR_5R_6$;
a group —$(CH_2)_n SO_2NR_5R_6$;
a group —$CH_2$—$(CH_2)_n NR_5SO_2R_6$;
a group —$(CH_2)_t$—$(C_6H_4)$—$SO_2(C_1-C_4)$alkyl;
group —$(CH_2)_r SO_2(C_1-C_4)$alkyl wherein the $(C_1-C_4)$alkyl is optionally substituted by —$NR_{15}R_{16}$ or —$N^+R_{15}R_{16}R_{17}$;
a group —$SO_2$-phenyl wherein the phenyl ring is optionally substituted by $NR_7R_8(C_1-C_6)$alkyl; or
a group —$(CH_2)_n$—W wherein W is a 5-6-membered heteroaryl ring which is optionally substituted by —$SO_2(C_1-C_4)$alkyl;
n is 1, 2 or 3;
t is zero, 1, 2 or 3;
r is zero, 1, 2, 3 or 4;
$R_5$ is: hydrogen, $(C_1-C_6)$alkyl, $NR_{16}R_{15}(C_1-C_6)$alkyl or $N^+R_{17}R_{15}R_{16}(C_1-C_6)$alkyl;
$R_6$ is hydrogen or $(C_1-C_6)$alkyl;
$R_7$ is: hydrogen, $(C_1-C_6)$alkyl, $(C_1-C_6)$alkylcarbonyl, —$SO_2(C_1-C_4)$alkyl, or $NR_{16}R_{15}(C_1-C_6)$alkyl;
$R_8$ is hydrogen or $(C_1-C_6)$alkyl; alternatively, $R_7$ and $R_8$ may form, together with the nitrogen atom to which they are attached, a $(C_5-C_7)$heterocycloalkyl ring system which is optionally substituted by one or more $(C_1-C_6)$ alkyl groups or oxo;
$R_{16}$ is hydrogen or $(C_1-C_6)$alkyl;
$R_{15}$ is hydrogen or $(C_1-C_6)$alkyl;
$R_{17}$ is hydrogen or $(C_1-C_6)$alkyl;
$R_3$ is —C(O)—$XR_4$;
X is: —O—;
$R_4$ is:
hydrogen; or
$(C_1-C_6)$alkyl;
$R_2$ is:
$NR_{18}R_{19}(C_1-C_6)$alkyl;
—$CONR_{21}R_{20}$;
$C_2-C_6$-alkenyl which is substituted by —OH or —$NR_{18}R_{19}$;
$C_2-C_6$-alkynyl which is substituted by —OH or —$NR_{18}R_{19}$; or
a group —$[CH_2]_y$-G-$[CH_2]_j$—$CH_2$—$N^+R_{22}R_{23}R_{24}$
or $R_2$ is a group:

or $R_2$ is a group:

$R_{14}$ is hydrogen or $(C_1-C_6)$alkyl which may be optionally substituted by a $(C_1-C_4)$alkoxyl group;

$R_{18}$ is hydrogen or $(C_1-C_6)$alkyl;

$R_{19}$ is hydrogen or $(C_1-C_6)$alkyl;

$R_{20}$ is: hydrogen, $(C_1-C_6)$alkyl, or $(C_1-C_6)$alkyl$NR_{18}R_{19}$;

$R_{21}$ is hydrogen or $(C_1-C_6)$alkyl;

j is an integer ranging from zero to 4;

y is an integer ranging from zero to 4;

G is a divalent linker selected from the group consisting of: —O—, —$(SO_2)$—, $NR_{25}$, a bond, $C_2$-$C_6$-alkenylene, $C_2$-$C_6$-alkynylene, $(C_3$-$C_6)$cycloalkylene, monocyclic heterocycloalkylene, bicyclic heterocycloalkylene, —[$CONR_{25}$]— and —[$NR_{25}CO$]—;

$R_{25}$ is hydrogen or $(C_1-C_6)$alkyl;

$R_{22}$ is: $(C_1-C_6)$alkyl, which is optionally substituted by one or more of $(C_3-C_6)$cycloalkyl, phenyl, benzyl, CN, —$OR_{26}$, —$SO_2R_{26}$, —$CO_2R_{26}$, —$CONR_{26}R_{27}$ or —$SO_2NR_{26}R_{27}$; $(C_3-C_{10})$cycloalkyl which is optionally substituted by one or more of —$OR_{26}$, —$SO_2R_{26}$, —$CO_2R_{26}$, —$CONR_{26}R_{27}$ or —$SO_2NR_{26}R_{27}$; or $(C_4-C_7)$heterocycloalkyl which is optionally substituted by one or more of —$OR_{26}$, —$SO_2R_{26}$, —$CO_2R_{26}$, —$CONR_{26}R_{27}$ or —$SO_2NR_{26}R_{27}$;

$R_{26}$ is hydrogen or $(C_1-C_6)$alkyl;

$R_{27}$ is hydrogen or $(C_1-C_6)$alkyl;

$R_{23}$ is hydrogen or $(C_1-C_6)$alkyl, which $(C_1-C_6)$alkyl is optionally substituted by one or more of —$OR_{29}$, —$SO_2R_{29}$, —$CO_2R_{29}$, —$CONR_{29}R_{30}$ or —$SO_2NR_{29}R_{30}$;

$R_{24}$ is hydrogen or $(C_1-C_6)$alkyl, which $(C_1-C_6)$alkyl is optionally substituted by one or more of —$OR_{31}$, —$SO_2R_{31}$, —$CO_2R_{31}$, —$CONR_{31}R_{32}$ or —$SO_2NR_{31}R_{32}$;

alternatively, $R_{23}$ and $R_{24}$ may form, together with the nitrogen atom to which they are attached, a 5-11-membered saturated monocyclic or bicyclic heterocyclic ring system which is optionally substituted by one or more of —$OR_{28}$, halo, $C_1$-$C_6$ alkyl, —$SO_2R_{33}$, —$CO_2R_{33}$, —$CONR_{33}R_{34}$ or —$SO_2NR_{33}R_{34}$; and which 5-11-membered saturated monocyclic or bicyclic ring optionally contains a further heteroatom which is oxygen or nitrogen or a —$SO_2$— group;

or $R_{22}$ together with $R_{23}$, $R_{24}$ and the nitrogen atom to which they are attached, may form a bridged bicyclic heterocyclic ring;

$R_{28}$ is hydrogen or $(C_1-C_6)$alkyl;

$R_{29}$ is hydrogen or $(C_1-C_6)$alkyl;

$R_{30}$ is hydrogen or $(C_1-C_6)$alkyl;

$R_{31}$ is hydrogen or $(C_1-C_6)$alkyl;

$R_{32}$ is hydrogen or $(C_1-C_6)$alkyl;

$R_{33}$ is hydrogen or $(C_1-C_6)$alkyl;

$R_{34}$ is hydrogen or $(C_1-C_6)$alkyl;

$R_{38}$ represents one or two optional substituents at each occurrence independently selected from the group consisting of: $(C_1-C_6)$alkyl, $(C_1-C_6)$alkoxyl, hydroxyl, hydroxyl-$C_1$-$C_6$-alkyl, halo, trifluoromethyl, and trifluoromethoxy;

wherein if one or more groups $N^+R_{11}R_{12}R_{13}$— or $N^+R_{15}R_{16}R_{17}$— are present, they form a quaternary salt with a pharmaceutically acceptable counter ion;

and wherein groups $R_5$ to $R_{38}$, and n may have the same or different meanings at each occurrence, if present in more than one group, or a pharmaceutically acceptable salt thereof.

2. The compound or pharmaceutically acceptable salt according to claim 1, wherein $R_2$ is —[$CH_2$]$_y$-G-[$CH_2$]$_j$—$CH_2$—$N^+R_{22}R_{23}R_{24}$.

3. The compound or pharmaceutically acceptable salt according to claim 1, wherein $R_4$ is $(C_1-C_6)$alkyl.

4. The compound or pharmaceutically acceptable salt according to claim 1, wherein $R_1$ is hydrogen or —$(CH_2)$,$SO_2$$(C_1-C_4)$alkyl.

5. A compound which is selected from the group consisting of:

5-[4-cyano-2-(4-hydroxy-but-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-cyano-2-(3-dimethylamino-prop-1-ynyl)-phenyl]-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-cyano-2-[2-(3-methanesulfonyl-propyl)-6-methoxycarbonyl-7-methyl-3-oxo-8-m-tolyl-2,3,5,8-tetrahydro-[1,2,4]triazolo[4,3-a]pyrimidin-5-yl]-phenyl}-prop-2-ynyl)-trimethyl-ammonium formate;

5-[4-cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-cyano-2-dimethylaminomethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

{5-cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium bromide;

(2-{5-cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzoylamino}-ethyl)-trimethyl-ammonium chloride;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium formate;

(R)-5-[4-cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-prop-2-ynyl)-trimethyl-ammonium iodide;

(R)-5-[4-cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium iodide;

5-[4-cyano-2-(4-hydroxy-but-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-[4-cyano-2-(3-dimethylamino-prop-1-ynyl)-phenyl]-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-cyano-2-[2-(3-methanesulfonyl-propyl)-6-methoxycarbonyl-7-methyl-3-oxo-8-m-tolyl-2,3,5,8-tetrahydro-[1,2,4]triazolo[4,3-a]pyrimidin-5-yl]-phenyl}-prop-2-ynyl)-trimethyl-ammonium formate;

5-[4-cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-cyano-2-dimethylaminomethyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

{5-cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium bromide;

(2-{5-cyano-2-[6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzoylamino}-ethyl)-trimethyl-ammonium chloride;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-trimethyl-ammonium formate;

(R)-5-[4-cyano-2-(3-dimethylamino-propyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-prop-2-ynyl)-trimethyl-ammonium iodide;

(R)-5-[4-cyano-2-(3-dimethylamino-prop-1-ynyl)-phenyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium iodide;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium iodide;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(3-methanesulfonyl-propyl)-dimethyl-ammonium formate;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-cyclopropylmethyl-dimethyl-ammonium formate;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(3-hydroxy-propyl)-dimethyl-ammonium formate;

(3-{5-cyano-2-[(R)-6-methoxycarbonyl-7-methyl-3-oxo-8-(3-trifluoromethyl-phenyl)-2,3,5,8-tetrahydro[1,2,4]triazolo[4,3-a]pyrimidin-5-yl]-phenyl}-propyl)-(3-methoxy-propyl)-dimethyl-ammonium formate;

(3-{5-cyano-2-[(R)-6-methoxycarbonyl-7-methyl-3-oxo-8-(3-trifluoromethyl-phenyl)-2,3,5,8-tetrahydro[1,2,4]triazolo[4,3-a]pyrimidin-5-yl]-phenyl}-propyl)-dimethylcarbamoylmethyl-dimethyl-ammonium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-1-azonia-bicyclo[2.2.2]octane formate;

1-(3-{5-cyano-2-[(R)-6-methoxycarbonyl-7-methyl-3-oxo-8-(3-trifluoromethyl-phenyl)-2,3,5,8-tetrahydro[1,2,4]triazolo[4,3-a]pyrimidin-5-yl]-phenyl}-propyl)-4-aza-1-azonia-bicyclo[2.2.2]octane formate;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-(4-hydroxy-cyclohexyl)-dimethyl-ammonium formate;

4-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-4-methyl-morpholin-4-ium formate;

adamantan-1-yl-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-ammonium formate;

4-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methyl-morpholin-4-ium formate;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-hydroxy-propyl)-dimethyl-ammonium formate;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-ethyl-dimethyl-ammonium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-azonia-bicyclo[2.2.2]octane formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1,4-dimethyl-piperazin-1-ium formate;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(4-hydroxy-cyclohexyl)-dimethyl-ammonium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-aza-1-azonia-bicyclo[2.2.2]octane formate;

1-{2-[(R)-6-carboxy-7-methyl-3-oxo-8-(3-trifluoromethyl-phenyl)-2,3,5,8-tetrahydro-[1,2,4]triazolo[4,3-a]pyrimidin-5-yl]-5-cyano-benzyl}-4-aza-1-azonia-bicyclo[2.2.2]octane formate;

butyl-{5-cyano-2-[(R)-6-methoxy carbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-ammonium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-hydroxy-1-methyl-piperidinium formate;

1-{5-cano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-methyl-pyrrolidinium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-methyl-piperidinium formate;

1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-1-(2-hydroxy-ethyl)-pyrrolidinium formate;

{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(3-dimethylcarbamoyl-propyl)-dimethyl-ammonium formate;

benzyl-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-ammonium formate;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium bromide;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-trimethyl-ammonium benzenesulfonate;

(5-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-pentyl)-trimethyl-ammonium formate;

(4-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-trimethyl-ammonium formate;

1-(4-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-1-azonia-bicyclo[2.2.2]octane formate;

1-(4-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-butyl)-1-azonia-bicyclo[2.2.2]octane formate;

(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium bromide;

(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-trimethyl-ammonium bromide;

1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridinium bromide;

1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-pyridininium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium bromide;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium benzenesulfonate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium chloride;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium 2-hydroxy-ethanesulfonate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium methanesulfonate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-hydroxymethyl-pyridinium tosylate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-methyl-pyridinium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-2-methyl-pyridinium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-3-hydroxymethyl-pyridinium formate;

3-chloro-1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-propyl)-pyridinium formate;

butyl-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-ammonium formate;

(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclohexyl-dimethyl-ammonium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-methyl-pyrrolidinium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-methyl-piperidinium formate;

1-(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-hydroxy-1-methyl-piperidinium formate;

(3-{5-cyano-2-[(R)-6-methoxycarbonyl-7-methyl-3-oxo-8-(3-trifluoromethyl-phenyl)-2,3,5,8-tetrahydro-[1,2,4]

triazolo[4,3-a]pyrimidin-5-yl]-phenyl}-ethyl)-dimethyl-oxetan-3-yl-ammonium formate;
(3-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-(tetrahydro-pyran-4-yl)-ammonium formate;
4-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-4-methyl-morpholin-4-ium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethylcarbamoylmethyl-dimethyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(3-methoxy-propyl)-dimethyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclobutylmethyl-dimethyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-(tetrahydro-pyran-4-ylmethyl)-ammonium formate;
1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-(2-hydroxy-ethyl)-pyrrolidinium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-[2-(2-hydroxy-ethoxy)-ethyl]-dimethyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-bis-(2-hydroxy-ethyl)-methyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(2-hydroxy-ethyl)-dimethyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-ethyl-dimethyl-ammonium formate;
benzyl-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-dimethyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclohexylmethyl-dimethyl-ammonium formate;
(2-{5-cano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-(3-hydroxy-propyl)-dimethyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-diethyl-methyl-ammonium formate;
(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-cyclopropylmethyl-dimethyl-ammonium formate;
1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-1-azonia-bicyclo[2.2.2]octane formate;
1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-hydroxymethyl-pyridinium formate;
1-(2-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-phenyl}-ethyl)-3-methyl-pyridinium formate;
{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-cyclobutylmethyl-dimethyl-ammonium formate;
{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-dimethyl-(tetrahydro-pyran-4-ylmethyl)-ammonium formate;
{{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(2-methoxy-ethyl)-dimethyl-ammonium formate;
{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-cyclopropylmethyl-dimethyl-ammonium formate;
3-chloro-1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-pyridinium formate;
{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-(2-hydroxy-ethyl)-dimethyl-ammonium formate;
1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-methoxy-pyridinium formate;
1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-3-hydroxymethyl-pyridinium formate;
{1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-hydroxymethyl-1-methyl-piperidinium formate;
{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-ethoxycarbonylmethyl-dimethyl-ammonium formate;
{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzy}-(1,1-dioxo-hexahydro-1lambda*6*-thiopyran-4-ylmethyl)-dimethyl-ammonium formate;
1-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-3,4-dihydroxy-1-methyl-pyrrolidinium formate;
4-{5-cyano-2-[(R)-6-methoxycarbonyl-7-methyl-3-oxo-8-(3-trifluoromethyl-phenyl)-2,3,5,8-tetrahydro-[1,2,4]triazolo[4,3-a]pyrimidin-5-yl]-benzyl}-4-ethyl-morpholin-4-ium formate;
1-{5-cyano-2-[(R)-6-methoxycarbonyl-7-methyl-3-oxo-8-(3-trifluoromethyl-phenyl)-2,3,5,8-tetrahydro-[1,2,4]

triazolo[4,3-a]pyrimidin-5-yl]-benzyl}-4-dimethylcar-
bamoyl-1-methyl-piperazin-1-ium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-dimethylcar-
bamoylmethyl-dimethyl-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-(1-methane-
sulfonyl-piperidin-4-yl)-dimethyl-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-dimethyl-ox-
etan-3-ylmethyl-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-dimethyl-(3-
methylcarbamoyl-propyl)-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-(3-dimethylsul-
famoyl-propyl)-dimethyl-ammonium formate;
1-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-4-methane-
sulfonyl-1-methyl-piperazin-1-ium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-bis-(2-hy-
droxy-ethyl)-methyl-ammonium formate;
1-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-4,4-difluoro-1-
methyl-piperidinium formate;
4-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-4-methyl-[1,4]
oxazepan-4-ium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-(3-methoxy-
propyl)-dimethyl-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-(3-methane-
sulfonyl-propyl)-dimethyl-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-dimethyl-(1-
methyl-piperidin-4-yl)-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-dimethyl-pip-
eridin-4-yl-ammonium formate;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-dimethyl-(tet-
rahydro-pyran-4-yl)-ammonium formate;
1-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-pyridinium
bromide;
1-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-pyridinium
benzenesulphonate;
1-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-pyridinium
tosylate;
benzyl-{5-cyano-2-[(R)-6-methoxycarbonyl-7-methyl-3-
oxo-8-(3-trifluoromethyl-phenyl)-2,3,5,8-tetrahydro-
[1,2,4]triazolo[4,3-a]pyrimidin-5-yl]-benzyl}-dim-
ethyl-ammonium bromide;
benzyl-{5-cyano-2-[(R)-6-methoxycarbonyl-7-methyl-3-
oxo-8-(3-trifluoromethyl-phenyl)-2,3,5,8-tetrahydro-
[1,2,4]triazolo[4,3-a]pyrimidin-5-yl]-benzyl}-dim-
ethyl-ammonium benzenesulfonate;
4-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-4-methyl-mor-
pholin-4-ium bromide;
4-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-4-methyl-mor-
pholin-4-ium bromide;
4-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-4-methyl-mor-
pholin-4-ium bromide;
4-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-4-methyl-mor-
pholin-4-ium bromide;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-trimethyl-am-
monium benzenesulfonate;
1-(2-{5-cyano-2-[(R)-6-methoxycarbonyl-7-methyl-3-
oxo-8-(3-trifluoromethyl-phenyl)-2,3,5,8-tetrahydro-
[1,2,4]triazolo[4,3-a]pyrimidin-5-yl]-phenyl}-ethyl)-
pyridinium 2-hydroxy-ethanesulfonate;
1-(2-{5-cyano-2-[(R)-6-methoxycarbonyl-7-methyl-3-
oxo-8-(3-trifluoromethyl-phenyl)-2,3,5,8-tetrahydro-
[1,2,4]triazolo[4,3-a]pyrimidin-5-yl]-phenyl}-ethyl)-
pyridinium methanesulfonate;
1-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-benzyl}-pyridinium
chloride;
{5-cyano-2-[(R)-6-methoxycarbonyl-7-methyl-3-oxo-8-
(3-trifluoromethyl-phenyl)-2,3,5,8-tetrahydro-[1,2,4]
triazolo[4,3-a]pyrimidin-5-yl]-benzyl}-bis-(2-hy-
droxy-ethyl)-methyl-ammonium benzenesulfonate;
1-(2-{5-cyano-2-[(R)-6-methoxycarbonyl-7-methyl-3-
oxo-8-(3-trifluoromethyl-phenyl)-2,3,5,8-tetrahydro-
[1,2,4]triazolo[4,3-a]pyrimidin-5-yl]-phenyl}-ethyl)-
pyridinium benzenesulfonate;
(2-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-phenyl}-ethyl)-trim-
ethyl-ammonium2-hydroxy-ethanesulfonate;
(2-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-phenyl}-ethyl)-trim-
ethyl-ammonium methanesulfonate; and
(2-{5-cyano-2-[(R)-6-methoxycarbonyl-7-methyl-3-oxo-
8-(3-trifluoromethyl-phenyl)-2,3,5,8-tetrahydro-[1,2,4]
triazolo[4,3-a]pyrimidin-5-yl]-phenyl}-ethyl)-trim-
ethyl-ammonium chloride;
or a pharmaceutically acceptable salt of said compound.

6. The compound or pharmaceutically acceptable salt according to claim 1, which has the absolute configuration at carbon (1) shown in formula (I)':

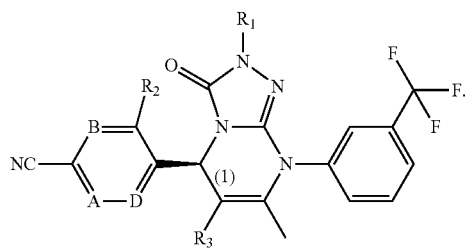

(I)'

7. The compound or pharmaceutically acceptable salt according to claim 1, which is in the form of a pharmaceutically acceptable salt.

8. A pharmaceutical composition, comprising a compound or pharmaceutically acceptable salt according to claim 1 and at least one pharmaceutically acceptable carrier or excipient.

9. The pharmaceutical composition according to claim 8, which is in a form suitable for oral administration or administration by the pulmonary route.

10. The pharmaceutical composition, comprising a compound or pharmaceutically acceptable salt according to claim 3 and at least one pharmaceutically acceptable carrier or excipient.

11. The pharmaceutical composition, comprising a compound or pharmaceutically acceptable salt according to claim 5 and at least one pharmaceutically acceptable carrier or excipient.

12. The compound or pharmaceutically acceptable salt according to claim 1, wherein $R_2$ is $NR_{18}R_{19}(C_1$-$C_6)$alkyl.

13. The compound or pharmaceutically acceptable salt according to claim 1, wherein $R_2$ is —$CONR_{21}R_{20}$.

14. The compound or pharmaceutically acceptable salt according to claim 1, wherein $R_2$ is $C_2$-$C_6$-alkenyl which is substituted by —OH or —$NR_{18}R_{19}$.

15. The compound or pharmaceutically acceptable salt according to claim 1, wherein $R_2$ is $C_2$-$C_6$-alkynyl which is substituted by —OH or —$NR_{18}R_{19}$.

16. The compound or pharmaceutically acceptable salt according to claim 1, wherein $R_2$ is a group:

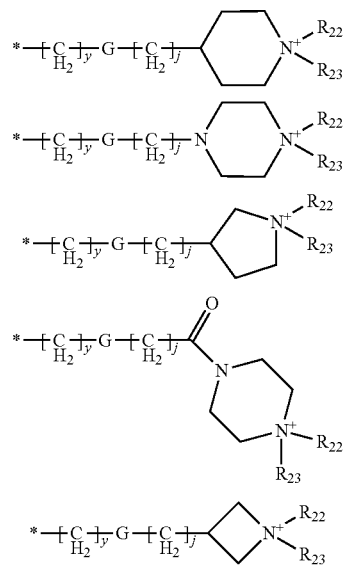

or $R_2$ is a group:

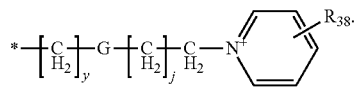

* * * * *